US008895544B2

(12) United States Patent
Coe et al.

(10) Patent No.: US 8,895,544 B2
(45) Date of Patent: Nov. 25, 2014

(54) INDAZOLES

(71) Applicant: Pfizer Limited, Sandwich (GB)

(72) Inventors: Jotham Wadsworth Coe, Niantic, CT (US); Christoph Martin Dehnhardt, Cambridge, MA (US); Peter Jones, Arlington, MA (US); Steven Wade Korturn, Groton, CT (US); Yogesh Anil Sabnis, Sandwich (GB); Florian Michel Wakenhut, Sandwich (GB); Gavin Alistair Whitlock, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 14/041,387

(22) Filed: Sep. 30, 2013

(65) Prior Publication Data

US 2014/0024634 A1 Jan. 23, 2014

Related U.S. Application Data

(62) Division of application No. 13/542,153, filed on Jul. 5, 2012, now Pat. No. 8,575,336.

(60) Provisional application No. 61/512,144, filed on Jul. 27, 2011.

(51) Int. Cl.
  *C07D 471/04* (2006.01)
  *C07D 487/04* (2006.01)
(52) U.S. Cl.
  CPC ............ *C07D 471/04* (2013.01); *C07D 487/04* (2013.01)
  USPC .................. 514/210.21; 514/215; 514/234.2; 514/252.11; 514/255.05; 514/303
(58) Field of Classification Search
  None
  See application file for complete search history.

(56) References Cited

U.S. PATENT DOCUMENTS

| 6,106,864 | A | 8/2000 | Dolan et al. |
| 7,884,109 | B2 | 2/2011 | Ohlmeyer et al. |
| 2013/0029968 | A1 | 1/2013 | Coe et al. |

FOREIGN PATENT DOCUMENTS

| WO | 91/11172 A1 | 8/1991 |
| WO | 94/02518 A1 | 2/1994 |
| WO | 98/55148 A1 | 12/1998 |
| WO | 00/35298 A1 | 6/2000 |
| WO | 2013/014567 A1 | 1/2013 |

OTHER PUBLICATIONS

Almarsson et al, "Crystal engineering of the composition of pharmaceutical phases. Do pharmaceutical co-crystals represent a new path to improved medicines?", Chem. Commun. 17:1889-1896 (2004).
Haleblian, "Characterization of Habits and Crystalline Modification of Solids and Their Pharmaceutical Applications", Journal of Pharmaceutical Sciences 64(8):1269-1288 (1975).
Liang et al, "Fast-dissolving intraoral drug delivery systems", Expert Opinion in Therapeutic Patents 11(6):981-986 (2001).

*Primary Examiner* — Janet L Andres
*Assistant Examiner* — Timothy R Rozof
(74) *Attorney, Agent, or Firm* — A. David Joran

(57) ABSTRACT

A method of treating a disease or condition for which a JAK inhibitor is indicated in a subject in need of such treatment, comprising administering to the subject a therapeutically effective amount of a compound of formula (I)

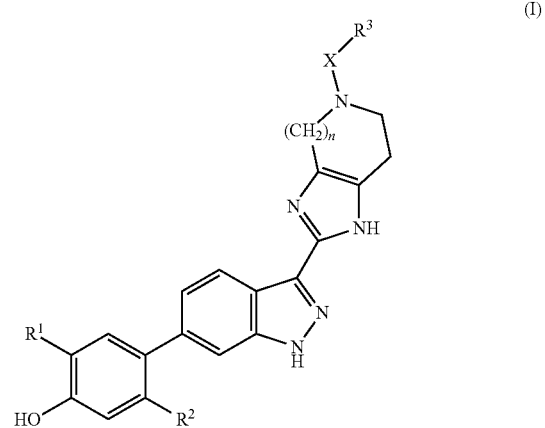

or a pharmaceutically acceptable salt thereof, or a pharmaceutically acceptable solvate of said compound or pharmaceutically acceptable salt, and particularly, a method for the treatment of various inflammatory diseases, particularly psoriasis, asthma and COPD.

18 Claims, No Drawings

INDAZOLES

The present invention is a divisional of U.S. Ser. No. 13/542,153, filed Jul. 5, 2012, now U.S. Pat. No. 8,575,336, which claims the benefit of U.S. Provisional Application No. 61/512,144, filed Jul. 27, 2011.

The present invention relates to indazoles, pharmaceutical compositions comprising such compounds and their use as medicaments. More particularly, the present invention provides 6-phenyl-1H-indazole derivatives which are Janus Kinase (JAK) inhibitors and useful for the treatment of allergic and respiratory conditions, particularly chronic obstructive pulmonary disease.

Chronic obstructive pulmonary disease (COPD) is the fourth leading cause of death in the US and is characterized by airflow obstruction that is not fully reversible with bronchodilators. The airflow limitation is usually progressive and is associated with an abnormal inflammatory response of the lungs to noxious particles or gases, primarily cigarette smoke. Symptoms are typically breathing-related (e.g. chronic cough, exertional dyspnea, expectoration and wheeze). Patients experience periods of stable disease interspersed with inflammatory exacerbations resulting in acute decline in lung function and often hospitalization.

Current treatment guidelines recommend bronchodilators as the mainstay of COPD drug treatment. However, anti-inflammatory inhaled corticosteroids (ICS) and bronchodilator/inhaled corticosteroid combination products are extensively used. Whilst inhaled corticosteroids do provide some benefits with respect to short term lung function improvements and exacerbation frequency, they do not address the corticosteroid-refractory inflammation which is characteristic of this disease and thought to play a key role in disease progression. There is a clear medical need for anti-inflammatory therapies in COPD that will address the chronic inflammatory component of the disease and ultimately provide symptomatic relief, a reduction in exacerbation frequency and an amelioration of exacerbation severity.

The Janus kinase (JAK) family of receptor associated tyrosine kinases, JAK 1, JAK 2, JAK 3 and tyrosine kinase 2 (TYK2), are involved in signal transduction associated with a variety of inflammatory cytokines. JAK kinases can function as either hetero or homo-dimers, phosphorylating STAT transcription factors which regulate inflammatory gene transcription. Oral JAK 1/JAK 3 inhibitors such as CP-690550 have shown impressive anti-inflammatory activity in inflammatory diseases such as rheumatoid arthritis and psoriasis.

Many JAK dependent cytokines are thought to play key roles in the pathology of COPD which involves the interplay of multiple inflammatory cells such as T lymphocytes, neutrophils, macrophages and lung epithelium. For example the JAK 1/JAK 3 heterodimer plays a key role in T lymphocyte survival and activation whereas JAK 2 is thought to be critical for regulation of neutrophil activation and apoptosis. JAK 1 and JAK 2 play an important role in IL-13 mediated inflammatory signaling in macrophages, which is thought to link acute inflammatory events to chronic progressive disease. Importantly JAK 1, JAK 2 and TYK 2 also play an important role in signaling mediated by IFNγ, a cytokine associated with the chronic inflammation observed in COPD, which modulates the activity of T cells, epithelium and macrophages whilst not being modulated by corticosteroids.

Macrophage phagocytosis of bacteria is impaired in the lungs of COPD patients, potentially in part due to high local IFNγ levels. In vitro studies with isolated patient cells have shown that JAK inhibitors increase phagocytic rate in the presence of IFNγ. Consequently, as well as exerting a direct anti-inflammatory effect, JAK inhibitors may also increase the ability of the lung to maintain a sterile environment.

JAK inhibitors are therefore likely to have utility in the treatment of a range of inflammatory diseases, including lung diseases such as COPD, asthma and pulmonary vascular disease. Compounds which have a broad inhibitory activity across the range of Janus kinases, in particular, are likely to have a potent anti-inflammatory effect. However, such a selectivity profile can also lead to undesirable side-effects in systemically circulating compounds, particularly anemia and neutropenia associated with JAK 2 inhibition. For the treatment of lung diseases, it is therefore particularly favourable to provide JAK inhibitors which can be administered by inhalation and which inhibit Janus kinases locally in the lung without having a significant systemic exposure.

There is thus a need to provide new JAK inhibitors that are potent, selective inhibitors of Janus kinases with appropriate metabolic stability and pharmacokinetic properties, particularly compounds which can be administered by inhalation and are active in lung tissue whilst having poor systemic penetration or high systemic lability.

The invention therefore provides, as embodiment E1, a compound of formula (I):

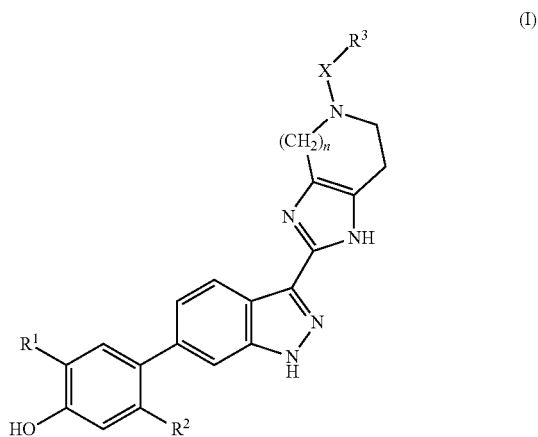

or a pharmaceutically acceptable salt thereof, or a pharmaceutically acceptable solvate of said compound or pharmaceutically acceptable salt, wherein:

$R^1$ is halo;

$R^2$ is $C_1$-$C_6$ alkyl optionally substituted by one or more fluorine atoms;

X is a bond, —CO—, —$SO_2$— or —$CH_2$—;

$R^3$ is Aryl$^1$, Het$^1$ or Het$^2$, each of which is optionally substituted by 1 substituent —Y—$R^4$ and/or 1-4 substituents each independently selected from $R^5$;

n is 1 or 2;

Aryl$^1$ is phenyl or naphthyl;

Het$^1$ is (i) a 6-membered aromatic heterocycle containing 1-3 N atoms or (ii) a 5-membered aromatic heterocycle containing either (a) 1-4 N atoms or (b) 1 O or S atom and 0-3 N atoms;

Het$^2$ is (i) a 10-membered bicyclic aromatic heterocycle containing 1-4 N atoms or (ii) a 9-membered bicyclic aromatic heterocycle containing either (a) 1-4 N atoms or (b) 1 O or S atom and 0-3 N atoms or (iii) an 8-membered bicyclic aromatic heterocycle containing (a) 1-4 N atoms or (b) 1 O or S atom and 1-3 N atoms or (c) 2 O or S atoms and 0-2 N atoms;

Y is a bond or —O—;

$R^4$ is Aryl$^2$ or Het$^3$;

$R^5$ is $C_1$-$C_6$ alkyl, $C_3$-$C_8$ cycloalkyl, halo, —CN, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ or —$NR^6SO_2NR^7R^8$;

$R^6$ is H, $C_1$-$C_8$ alkyl or $C_3$-$C_8$ cycloalkyl, said $C_1$-$C_6$ alkyl;

$R^7$ and $R^8$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl;

$Aryl^2$ is phenyl or naphthyl, said phenyl and naphthyl being optionally substituted with 1-5 substituents selected from $C_1$-$C_6$ alkyl, $C_3$-$C_8$ cycloalkyl, halo, —CN, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$; and $Het^3$ is a 3 to 8-membered saturated or partially unsaturated monocyclic heterocycle, containing 1 or 2 heteroatoms selected from O and N, said heterocycle being optionally substituted by 1-5 substituents selected from $C_1$-$C_8$ alkyl, $C_3$-$C_8$ cycloalkyl, halo, oxo, —$OR^6$, —$NR^7R^8$, —$SR^6$, —$SOR^9$, —$SO_2R^9$, —$COR^6$, —$OCOR^6$, —$COOR^6$, —$NR^6COR^6$, —$CONR^7R^8$, —$NR^6SO_2R^9$, —$SO_2NR^7R^8$, —$NR^6CONR^7R^8$, —$NR^6COOR^9$ and —$NR^6SO_2NR^7R^8$.

The invention also provides, as embodiment E2, a compound of formula (I), or a pharmaceutically acceptable salt thereof, or a pharmaceutically acceptable solvate of said compound or pharmaceutically acceptable salt, wherein $R^2$, n, X and $R^3$ are as defined in embodiment E1 and $R^1$ is fluoro.

The invention also provides, as embodiment E3, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, n, X and $R^3$ are as defined in embodiment $E^1$ and $R^2$ is $CH_2CH_3$ or $CH_2CF_3$.

The invention also provides, as embodiment E4, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, X and $R^3$ are as defined in embodiment E1 and n is 1.

The invention also provides, as embodiment E5, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, X and $R^3$ are as defined in embodiment E1 and n is 2.

The invention also provides, as embodiment E6, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is defined in any one of embodiments E1, E4 or E5, $R^3$ is as defined in embodiment E1 and X is a bond.

The invention also provides, as embodiment E7, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is defined in any one of embodiments E1, E4 or E5, $R^3$ is as defined in embodiment E1 and X is —CO—.

The invention also provides, as embodiment E8, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is defined in any one of embodiments E1, E4 or E5, $R^3$ is as defined in embodiment E1 and X is —$CH_2$—.

The invention also provides, as embodiment E9, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is defined in any one of embodiments E1, E4 or E5, $R^3$ is as defined in embodiment E1 and X is —$SO_2$—.

The invention also provides, as embodiment E10, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is as defined in any one of embodiments E1, E4 or E5, X is as defined in any one of embodiments E1, E6, E7, E8 or E9 and $R^3$ is phenyl, thiazolyl, quinolinyl, pyrimidinyl, [1,8]naphthyridinyl or pyridyl, each of which is optionally substituted by 1 substituent —Y—$R^4$ and 1-4 substituents each independently selected from $R^5$.

The invention also provides, as embodiment E11, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is as defined in any one of embodiments E1, E4 or E5, X is as defined in any one of embodiments E1, E6, E7, E8 or E9 and $R^3$ is phenyl, thiazolyl, quinolinyl, pyrimidinyl, [1,8]naphthyridinyl or pyridyl, each of which is optionally substituted by 1 substituent selected from piperidininyl, (fluorophenyl)oxy, phenyloxy and morpholinyl and 1-2 substituents each independently selected from fluoro, chloro, cyano, methoxy and hydroxy.

The invention also provides, as embodiment E12, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, X is as defined in any one of embodiments E1, E6, E7, E8 or E9 and $R^3$ is fluorophenyl, methoxyphenyl, thiazolyl, hydroxyphenyl, phenyl, quinolinyl, [1,8]naphthyridinyl, (piperidinyl)pyridyl, (piperidinyl)pyrimidinyl, ((fluorophenyl)oxy)pyrimidinyl, (phenyloxy)pyridyl, (morpholinyl)pyridyl, chloropyridyl or cyanopyridyl.

The invention also provides, as embodiment E13, a compound of formula (I), or a pharmaceutically acceptable salt thereof, or a pharmaceutically acceptable solvate of said compound or pharmaceutically acceptable salt, wherein $R^1$ is as defined in either of embodiments E1 or E2, $R^2$ is as defined in either of embodiments E1 or E3, n is defined in any one of embodiments E1, E4 or E5, and —X—$R^3$ is (fluorophenyl)carbonyl, (thiazolyl)carbonyl, benzyl, ((piperidinyl)pyrimidinyl)carbonyl, ((phenoxy)pyridyl)carbonyl, ((morpholinyl)pyridyl)sulphonyl, ((phenoxy)pyridyl)sulphonyl, (chloropyridyl)carbonyl, (cyanopyridyl)carbonyl, (fluorophenyl)carbonyl, (thiazolyl)carbonyl, (fluorophenyl)sulphonyl, ((fluorophenoxy)pyrimidinyl)carbonyl, (quinolinyl)methyl, (hydroxyphenyl)methyl, (cyanopyridyl)methyl, (methoxyphenyl)methyl, ((phenoxy)pyridyl)methyl, ((piperidinyl)pyridyl)methyl, ((cyanopyridyl)methyl, (fluorophenyl)methyl or ([1,8]naphthyridinyl)methyl.

The invention also provides, as embodiment E14, a compound of formula:

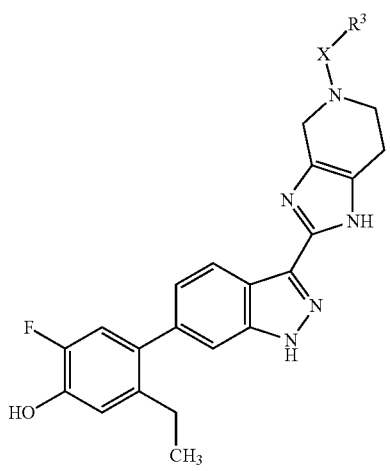

(Ia)

or a pharmaceutically acceptable salt thereof, or a pharmaceutically acceptable solvate of said compound or pharmaceutically acceptable salt, wherein X is as defined in any one of embodiments E1, E6, E7, E8 or E9 and $R^3$ is as defined in any one of embodiments E1, E10, E11 or E12 or X—$R^3$ is as defined in embodiment E13.

Particularly preferred compounds of formula (I) include:
{2-[6-(2-Ethyl-5-fluoro-4-hydroxy-phenyl)-1H-indazol-3-yl]-1,4,6,7-tetrahydro-imidazo[4,5-c]pyridin-5-yl}-(4-fluoro-phenyl)-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(5-piperidin-1-yl-pyrazin-2-yl)methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(6-phenoxy-pyridin-3-yl)-methanone;
5-Ethyl-2-fluoro-4-{3-[5-(6-morpholin-4-yl-pyridine-3-sulfonyl)-4,5,6,7-tetrahydro-1H-imidazo[4,5-c]pyridin-2-yl]-1H-indazol-6-yl}-phenol;
5-Ethyl-2-fluoro-4-{3-[5-(6-phenoxy-pyridine-3-sulfonyl)-4,5,6,7-tetrahydro-1H-imidazo[4,5-c]pyridin-2-yl]-1H-indazol-6-yl}-phenol;
(5-Chloro-pyridin-2-yl)-{2-[6-(2-ethyl-5-fluoro-4-hydroxy-phenyl)-1H-indazol-3-yl]-4,5,7,8-tetrahydro-1H-imidazo[4,5-d]azepin-6-yl}-methanone;
2-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}isonicotinonitrile;
{2-[6-(2-Ethyl-5-fluoro-4-hydroxy-phenyl)-1H-indazol-3-yl]-4,5,7,8-tetrahydro-1H-imidazo[4,5-d]azepin-6-yl}-(4-fluoro-phenyl)methanone;
{2-[6-(2-Ethyl-5-fluoro-4-hydroxy-phenyl)-1H-indazol-3-yl]-4,5,7,8-tetrahydro-1H-imidazo[4,5-d]azepin-6-yl}-isothiazol-3-yl-methanone;
5-Ethyl-2-fluoro-4-{3-[5-(4-fluoro-benzenesulfonyl)-4,5,6,7-tetrahydro-1H-imidazo[4,5-c]pyridin-2-yl]-1H-indazol-6-yl}-phenol;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-fluoro-phenoxy)-pyrazin-2-yl]-methanone;
4-[3-(6-Benzyl-1,4,5,6,7,8-hexahydro-imidazo[4,5-d]azepin-2-yl)-1H-indazol-6-yl]-5-ethyl-2-fluoro-phenol;
(5-Chloro-pyridin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
5-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-pyridine-2-carbonitrile;
5-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-pyridine-2-carbonitrile;
5-Ethyl-2-fluoro-4-[3-(5-quinolin-6-ylmethyl-4,5,6,7-tetrahydro-1H-imidazo[4,5-c]pyridin-2-yl)-1H-indazol-6-yl]-phenol;
5-Ethyl-2-fluoro-4-{3-[5-(4-hydroxy-benzyl)-4,5,6,7-tetrahydro-1H-imidazo[4,5-c]pyridin-2-yl]-1H-indazol-6-yl}-phenol;
5-Ethyl-2-fluoro-4-{3-[5-(3-hydroxy-benzyl)-4,5,6,7-tetrahydro-1H-imidazo[4,5-c]pyridin-2-yl]-1H-indazol-6-yl}-phenol;
4-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;
5-Ethyl-2-fluoro-4-{3-[5-(3-methoxy-benzyl)-4,5,6,7-tetrahydro-1H-imidazo[4,5-c]pyridin-2-yl]-1H-indazol-6-yl}-phenol;
5-Ethyl-2-fluoro-4-[3-(5-quinolin-3-ylmethyl-4,5,6,7-tetrahydro-1H-imidazo[4,5-c]pyridin-2-yl)-1H-indazol-6-yl]-phenol;
5-Ethyl-2-fluoro-4-{3-[5-(6-phenoxy-pyridin-3-ylmethyl)-4,5,6,7-tetrahydro-1H-imidazo[4,5-c]pyridin-2-yl]-1H-indazol-6-yl}-phenol;
5-Ethyl-2-fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-phenol;
3-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;
5-Ethyl-2-fluoro-4-{3-[5-(4-fluoro-benzyl)-4,5,6,7-tetrahydro-1H-imidazo[4,5-c]pyridin-2-yl]-1H-indazol-6-yl}-phenol;
5-Ethyl-2-fluoro-4-[3-(5-[1,8]naphthyridin-2-ylmethyl-4,5,6,7-tetrahydro-1H-imidazo[4,5-c]pyridin-2-yl)-1H-indazol-6-yl]-phenol;
(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(5-piperidin-1-yl-pyrazin-2-yl)-methanone;
(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(4-fluoro-phenyl)-methanone;
4-[3-(5-Benzyl-4,5,6,7-tetrahydro-1H-imidazo[4,5-c]pyridin-2-yl)-1H-indazol-6-yl]-2-fluoro-5-(2,2,2-trifluoro-ethyl)-phenol;

or a pharmaceutically acceptable salt thereof, or a pharmaceutically acceptable solvate of said compound or salt.

Other preferred compounds of formula (I) include:
{5-[(2-Dimethylamino-ethyl)-methyl-amino]-pyrazin-2-yl}-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-pyrrolidin-1-yl-ethylamino)-pyrazin-2-yl]-methanone;
[5-(2-Dimethylamino-ethylamino)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
[5-(4-Dimethylamino-piperidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-{5-[ethyl-(2-hydroxy-ethyl)-amino]-pyrazin-2-yl}-methanone;
[5-((R)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
[5-((S)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-etrahydroimidazo[4,5c]pyridin-5-yl}-[5-(2-piperidin-1-yl-ethylamino)-pyrazin-2-yl]-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-piperazin-1-yl-ethylamino)-pyrazin-2-yl]-methanone;
{2-[6-(2-Ethyl-5-fluoro-4-hydroxy-phenyl)-1H-indazol-3-yl]-1,4,6,7-tetrahydro-imidazo[4,5-]pyridin-5-yl}-(4-methyl-3,4,5,6-tetrahydro-2H-[1,2']bipyrazinyl-5'-yl)-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(5-morpholin-4-yl-pyrazin-2-yl)-methanone;
{2-[6-(2-Ethyl-5-fluoro-4-hydroxy-phenyl)-1H-indazol-3-yl]-1,4,6,7-tetrahydro-idazo[4,5c]pyridin-5-yl}-[5-(4-methyl-piperidin-1-yl)-pyrazin-2-yl]-methanone;
(5-Cyclopentylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-morpholin-4-yl-ethylamino)-pyrazin-2-yl]-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(4-isopropyl-3,4,5,6-tetrahydro-2H-[1,2']bipyrazinyl-5'-yl)-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(5-pyrrolidin-1-yl-pyrazin-2-yl)-methanone;
{2-[6-(2-Ethyl-5-fluoro-4-hydroxy-phenyl)-1H-indazol-3-yl]-1,4,6,7-tetrahydro-imidazo[4,5-]pyridin-5-yl}-[5-(ethyl-methyl-amino)-pyrazin-2-yl]-methanon;
(5-Cyclohexylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
(5-Dimethylamino-pyrazin-2-yl)-{2-[6-(2-ethyl-5-fluoro-4-hydroxy-phenyl)-1H-indazol-3-yl]-,4,6,7-tetrahydro-imidazo[4,5-c]pyridin-5-yl}-methanone;
(5-Azetidin-1-yl-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
2-Fluoro-4-{3-[5-(4-fluoro-benzyl)-4,5,6,7-tetrahydro-1H-imidazo[4,5-c]pyridin-2-yl]-1H-indazol-6-yl}-5-(2,2,2-trifluoro-ethyl)phenol;
2-Fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-5-(2,2,2-trifluoro-ethyl)-phenol;
2-Fluoro-4-{3-[5-(6-phenoxy-pyridin-3-ylmethyl)-4,5,6,7-tetrahydro-1H-imidazo[4,5-c]pyridin-2-yl]-H-indazol-6-yl}-5-(2,2,2-trifluoro-ethyl)-phenol;
2-Fluoro-4-{3-[5-(4-methoxy-benzyl)-4,5,6,7-tetrahydro-1H-imidazo[4,5-c]pyridin-2-yl]-1H indazol-6-yl}-5-(2,2,2-trifluoro-ethyl)phenol;
2-Fluoro-4-{3-[5-(4-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;
2-Fluoro-4-{3-[5-(3-methoxy-benzyl)-4,5,6,7-tetrahydro-1H-imidazo[4,5-c]pyridin-2-yl]-1H-indazol-6-yl}-5-(2,2,2-trifluoro-ethyl)-phenol;
2-Fluoro-4-{3-[5-(3-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;
2-Fluoro-4-[3-(5-quinolin-6-ylmethyl-4,5,6,7-tetrahydro-1H-imidazo[4,5-c]pyridin-2-yl)-1H-indazol-6-yl]-5-(2,2,2-trifluoro-ethyl)-phenol;
2-Fluoro-4-[3-(5-quinolin-3-ylmethyl-4,5,6,7-tetrahydro-1H-imidazo[4,5-c]pyridin-2-yl)-1H-indazol-6-yl]-5-(2,2,2-trifluoro-ethyl)-phenol;
2-Fluoro-4-[3-(5-[1,8]naphthyridin-3-ylmethyl-4,5,6,7-tetrahydro-1H-imidazo[4,5-c]pyridin-2-yl)-1H-indazol-6-yl]-5-(2,2,2-trifluoro-ethyl)-phenol;
((3R,5S)-3,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-((S)-3-methyl-3,4,5,6-tetrahydro-2H-[1,2']bipyrazinyl-5'-yl)-methanone;
((2S,5R)-2,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-]pyridin-5-yl}-(3,4,5,6-tetrahydro-2H-[1,2']bipyrazinyl-5'-yl)-methanone;
or a pharmaceutically acceptable salt thereof, or a pharmaceutically acceptable solvate of said compound or salt.

Most preferred is {2-[6-(2-ethyl-5-fluoro-4-hydroxy-phenyl)-1H-indazol-3-yl]-1,4,6,7-tetrahydro-imidazo[4,5-c]pyridin-5-yl}-(5-piperidin-1-yl-pyrazin-2-yl)-methanone or a pharmaceutically acceptable salt thereof, or a pharmaceutically acceptable solvate of said compound or salt.

The present invention also provides: a method of treating a disease for which a JAK inhibitor is indicated, in a subject in need of such treatment, comprising administering to the subject a therapeutically effective amount of a compound of formula (I), or a pharmaceutically acceptable salt thereof, or a pharmaceutically acceptable solvate of said compound or salt; the use of a compound of formula (I), or a pharmaceutically acceptable salt thereof, or a pharmaceutically acceptable solvate of said compound or salt, for the manufacture of a medicament for treating a disease or condition for which a JAK inhibitor is indicated; a compound of formula (I), or a pharmaceutically acceptable salt or solvate thereof, for use as a medicament; a compound of formula (I), or a pharmaceutically acceptable salt thereof, or a pharmaceutically acceptable solvate of said compound or salt, for use in the treatment of a disease or condition for which a JAK inhibitor is indicated; a pharmaceutical composition comprising a compound of formula (I), or a pharmaceutically acceptable salt thereof, or a pharmaceutically acceptable solvate of said compound or salt, and a pharmaceutically acceptable excipient; a pharmaceutical composition for the treatment of a disease or condition for which a JAK inhibitor is indicated, comprising a compound of formula (I), or a pharmaceutically acceptable salt thereof, or a pharmaceutically acceptable solvate of said compound or salt.

The disease or condition for which a JAK inhibitor is indicated is preferably an allergic or respiratory condition such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, pulmonary vasulcar disease (including pulmonary arterial hypertension), acute lung injury, bronchiectasis, sinusitis, allergic conjunctivitis, idiopathic pulmonary fibrosis or atopic dermatitis, particularly asthma or chronic obstructive pulmonary disease, most particularly chronic obstructive pulmonary disease.

Other diseases and conditions of interest are inflammation (including neuroinflammation), arthritis (including rheumatoid arthritis, spondyloarthropathies, systemic lupus erythematous arthritis, osteoarthritis and gouty arthritis), pain, fever, pulmonary sarcoisosis, silicosis, cardiovascular disease (including atherosclerosis, myocardial infarction, thrombosis, congestive heart failure and cardiac reperfusion injury), cardiomyopathy, stroke, ischaemia, reperfusion injury, brain edema, brain trauma, neurodegeneration, liver disease, inflammatory bowel disease (including Crohn's disease and ulcerative colitis), nephritis, retinitis, retinopathy, macular degeneration, glaucoma, diabetes (including type 1 and type 2 diabetes), diabetic neurorpathy, viral and bacterial infection, myalgia, endotoxic shock, toxic shock syndrome, autoimmune disease, osteoporosis, multiple sclerosis, endometriosis, menstrual cramps, vaginitis, candidiasis, cancer, fibrosis, obesity, muscular dystrophy, polymyositis, Alzheimer's disease, skin flushing, eczema, psoriasis, atopic dermatitis and sunburn.

Types of asthma include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

The treatment of asthma includes palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

The present invention also provides any of the uses, methods or compositions as defined above wherein the compound of formula (I), or pharmaceutically acceptable salt thereof, or pharmaceutically acceptable solvate of said compound or salt, is used in combination with another pharmacologically active compound, particularly one of the functionally-defined classes or specific compounds listed below. Generally, the compounds of the combination will be administered together as a formulation in association with one or more pharmaceutically acceptable excipients.

Suitable agents for use in combination therapy with a compound of formula (I), or pharmaceutically acceptable salt thereof, or pharmaceutically acceptable solvate of said compound or salt, particularly in the treatment of respiratory disease, include:

a 5-lipoxygenase activating protein (FLAP) antagonist;

a leukotriene antagonist (LTRA) such as an antagonist of $LTB_4$, $LTC_4$, $LTD_4$, $LTE_4$, $CysLT_1$ or $CysLT_2$, e.g. montelukast or zafirlukast;

a histamine receptor antagonist, such as a histamine type 1 receptor antagonist or a histamine type 2 receptor antagonist, e.g. loratidine, fexofenadine, desloratidine, levocetirizine, methapyrilene or cetirizine;

an α1-adrenoceptor agonist or an α2-adrenoceptor agonist, e.g. phenylephrine, methoxamine, oxymetazoline or methylnorephrine;

a muscarinic M3 receptor antagonist, e.g. tiotropium or ipratropium;

a dual muscarinic M3 receptor antagononist/β2 agonist;

a PDE inhibitor, such as a PDE3 inhibitor, a PDE4 inhibitor or a PDE5 inhibitor, e.g. theophylline, sildenafil, vardenafil, tadalafil, ibudilast, cilomilast or roflumilast; sodium cromoglycate or sodium nedocromil;

a cyclooxygenase (COX) inhibitor, such as a non-selective inhibitor (e.g. aspirin or ibuprofen) or a selective inhibitor (e.g. celecoxib or valdecoxib);

a glucocorticosteroid, e.g. fluticasone, mometasone, dexamethasone, prednisolone, budesonide, ciclesonide or beclamethasone;

an anti-inflammatory monoclonal antibody, e.g. infliximab, adalimumab, tanezumab, ranibizumab, bevacizumab or mepolizumab;

a β2 agonist, e.g. salmeterol, albuterol, salbutamol, fenoterol or formoterol, particularly a long-acting β2 agonist;

an intigrin antagonist, e.g. natalizumab;

an adhesion molecule inhibitor, such as a VLA-4 antagonist;

a kinin $B_1$ or $B_2$ receptor antagonist;

an immunosuppressive agent, such as an inhibitor of the IgE pathway (e.g. omalizumab) or cyclosporine;

a matrix metalloprotease (MMP) inhibitor, such as an inhibitor of MMP-9 or MMP-12;

a tachykinin $NK_1$, $NK_2$ or $NK_3$ receptor antagonist;

a protease inhibitor, such as an inhibitor of elastase, chymase or catheopsin G;

an adenosine $A_{2a}$ receptor agonist;

an adenosine $A_{1b}$ receptor antagonist;

a urokinase inhibitor;

a dopamine receptor agonist (e.g. ropinirole), particularly a dopamine D2 receptor agonist (e.g. bromocriptine);

a modulator of the NFκB pathway, such as an IKK inhibitor;

a further modulator of a cytokine signalling pathway such as an inhibitor of JAK kinase, syk kinase, p38 kinase, SPHK-1 kinase, Rho kinase, EGF-R or MK-2;

a mucolytic, mucokinetic or anti-tussive agent an antibiotic;

an antiviral agent;

a vaccine;

a chemokine;

an epithelial sodium channel (ENaC) blocker or Epithelial sodium channel (ENaC) inhibitor;
a nucleotide receptor agonist, such as a P2Y2 agonist;
a thromboxane inhibitor;
niacin;
a 5-lipoxygenase (5-LO) inhibitor, e.g. Zileuton;
an adhesion factor, such as VLAM, ICAM or ELAM;
a CRTH2 receptor ($DP_2$) antagonist;
a prostaglandin $D_2$ receptor ($DP_1$) antagonist;
a haematopoietic prostaglandin D2 synthase (HPGDS) inhibitor; interferon-β;
a soluble human TNF receptor, e.g. Etanercept;
a HDAC inhibitor;
a phosphoinositotide 3-kinase gamma (PI3Kγ) inhibitor;
a phosphoinositide 3-kinase delta (PI3Kδ) inhibitor;
a CXCR-1 or a CXCR-2 receptor antagonist;
an IRAK-4 inhibitor; and
a TLR-4 or TLR-9 inhibitor;
including the pharmaceutically acceptable salts of the specifically named compounds and the pharmaceutically acceptable solvates of said specifically named compounds and salts.

Besides being useful for human treatment, compounds of formula (I) are also useful for veterinary treatment of companion animals, exotic animals and farm animals.

When used in the present application, the following abbreviations have the meanings set out below:
AcOH is acetic acid;
APCI (in relation to mass spectrometry) is atmospheric pressure chemical ionization;
BOP is (benzotriazol-1-yloxy)tris(dimethylamino)phosphonium hexafluorophosphate;
Calc is calculated;
$CDCl_3$ is deuterochloroform;
$CO_2Et$ is ethyl carboxylate;
DCC is N,N'-dicyclohexylcarbodiimide;
DCM is dichloromethane;
DEA is diethylamine;
DIAD is diisopropyl azodicarboxylate;
DIEA is N,N-diisopropylethylamine;
DIPEA is N,N-diisopropylethylamine;
DMA is N,N-dimethylacetamide;
DMF is dimethylformamide;
DMSO-$d_6$ is fully deuterated dimethyl sulphoxide;
EDC/EDCI is N-(3-Dimethylaminopropyl)-N'-ethylcarbodiimide hydrochloride;
ES (in relation to mass spectrometry) is electrospray;
Et is ethyl;
EtOAc is ethyl acetate
Ex is Example;
h is hour(s);
HATU is N,N,N',N'-tetramethyl-O-(7-azabenzotriazol-1-yl)uronium hexafluorophosphate;
HBTU is N,N,N'N-tetramethyl-O-(1H-benzotriazol-1-yl) uronium hexafluorophosphate;
HCl is hydrochloric acid;
1H NMR or $^1$H NMR is proton nuclear magnetic resonance;
HOAt is 1-hydroxy-7-azabenzotriazole;
HOBt is 1-hydroxybenzotriazole;
HPLC is high performance liquid chromatography;
$H_2SO_4$ is sulphuric acid;
IPA is isopropyl alcohol;
iPr is isopropyl;
$K_2CO_3$ is potassium carbonate;
$KMnO_4$ is potassium permanganate;
KOH is potassium hydroxide;
KOAc is potassium acetate;
LCMS is liquid chromatography mass spectrometry;
LRMS is low resolution mass spectrometry;
NMM is 4-methylmorpholine;
Me is methyl;
MeCN is acetonitrile;
MeOD-$d_4$ is fully deuterated methanol;
$MgSO_4$ is magnesium sulphate;
2-MeTHF is 2-methyltetrahydrofuran;
min is minute(s);
MS is mass spectroscopy;
NaCl is sodium chloride;
NaH is sodium hydride;
NBS is N-bromosuccinimide;
NIS is N-iodosuccinimide;
NMP is N-methylpyrrolidine;
Obs is observed;
$Pd(OAc)_2$ is palladium(II)acetate;
RT is retention time;
SEM-Cl is (2-chloromethoxy-ethyl)-trimethyl-silane;
SPhos is 2-dicyclohexylphosphino-2',6'-dimethoxybiphenyl;
STAB is sodium (tri-acetoxy)borohydride;
TBTU is O-(benzotriazol-1-yl)-N,N,N',N'-tetramethyluronium tetrafluoroborate;
TEA is triethylamine;
TFA is trifluoroacetic acid;
THF is tetrahydrofuran;
tBME is 2-mMethoxy-2-methyl-propane;
p-TsOH is para-toluene sulfonic acid.

Unless otherwise defined herein, scientific and technical terms used in connection with the present invention have the meanings that are commonly understood by those of ordinary skill in the art.

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment. The term treatment encompasses any objective or subjective improvement in a subject with respect to a relevant condition or disease.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, decreased rate of a decline in lung function over time, inhibition of progressive nerve destruction, reduction of biomarkers associated and correlated with diseases or disorders, a reduction in relapses, improvement in quality of life, reduced time spent in hospital during an acute exacerbation event and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

The term "selective", when used to describe a functionally-defined receptor ligand or enzyme inhibitor means selective for the defined receptor or enzyme subtype as compared with other receptor or enzyme subtypes in the same family. For instance, a selective PDE5 inhibitor is a compound which inhibits the PDE5 enzyme subtype more potently than any other PDE enzyme subtype. Such selectivity is preferably at least 2 fold (as measured using conventional binding assays), more preferably at least 10 fold, most preferably at least 100 fold.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms.

The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical.

$Het^3$ is a saturated or partially saturated (i.e. non aromatic) heterocycle and may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

$Het^3$ may be fully saturated or partially unsaturated, i.e. may have one or more degrees of unsaturation but may not be fully aromatic.

$Het^1$ is an aromatic heterocycle and may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl.

$Het^2$ is an aromatic heterocycle and may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). $Het^2$ is aromatic and is therefore necessarily a fused bicycle. Specific examples include imidazo[2,1-b][1,3]thiazolyl, benzofuranyl, benzothienyl, indolyl, benzimidazolyl, indazolyl, benzotriazolyl, pyrrolo[2,3-b]pyridyl, pyrrolo[2,3-c]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-b]pyridyl, isoindolyl, indazolyl, purinyl, indolizinyl, imidazo[1,2-a]pyridyl, imidazo[1,5-a]pyridyl, pyrazolo[1,5-a]pyridyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl, pyrido[3,4-b]pyrazinyl, pyrimido[5,4-d]pyrimidinyl, pyrazino[2,3-b]pyrazinyl and pyrimido[4,5-d]pyrimidine.

The term "cycloalkyl" means a means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The term "oxo" means a doubly bonded oxygen.

The term "alkoxy" means a radical comprising an alkyl radical that is bonded to an oxygen atom, such as a methoxy radical. Examples of such radicals include methoxy, ethoxy, propoxy, isopropoxy, butoxy and tert-butoxy.

The term "halo" means, fluoro, chloro, bromo or iodo.

As used herein, the terms "co-administration", "co-administered" and "in combination with", referring to a combination of a compound of formula (I) and one or more other therapeutic agents, includes the following:

simultaneous administration of such a combination of a compound of formula (I) and a further therapeutic agent to a patient in need of treatment, when such components are formulated together into a single dosage form which releases said components at substantially the same time to said patient, substantially simultaneous administration of such a combination of a compound of formula (I) and a further therapeutic agent to a patient in need of treatment, when such components are formulated apart from each other into separate dosage forms which are taken at substantially the same time by said patient, whereupon said components are released at substantially the same time to said patient, sequential administration of such a combination of a compound of formula (I) and a further therapeutic agent to a patient in need of treatment, when such components are formulated apart from each other into separate dosage forms which are taken at consecutive times by said patient with a significant time interval between each administration, whereupon said components are released at substantially different times to said patient; and sequential administration of such a combination of a compound of formula (I) and a further therapeutic agent to a patient in need of treatment, when such components are formulated together into a single dosage form which releases said components in a controlled manner.

The term 'excipient' is used herein to describe any ingredient other than a compound of formula (I). The choice of excipient will to a large extent depend on factors such as the particular mode of administration, the effect of the excipient on solubility and stability, and the nature of the dosage form. The term "excipient" encompasses diluent, carrier or adjuvant.

One way of carrying out the invention is to administer a compound of formula (I) in the form of a prodrug. Thus, certain derivatives of a compound of formula (I) which may have little or no pharmacological activity themselves can, when administered into or onto the body, be converted into a compound of formula (I) having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, ACS Symposium Series (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs in accordance with the invention can, for example, be produced by replacing appropriate functionalities present in the compounds of formula (I) with certain moieties known to those skilled in the art as 'pro-moieties' as described, for example, in 'Design of Prodrugs' by H. Bundgaard (Elsevier, 1985).

Thus, a prodrug in accordance with the invention is (a) an ester or amide derivative of a carboxylic acid in a compound of formula (I); (b) an ester, carbonate, carbamate, phosphate or ether derivative of a hydroxyl group in a compound of formula (I); (c) an amide, imine, carbamate or amine derivative of an amino group in a compound form formula (I); (d) a thioester, thiocarbonate, thiocarbamate or sulphide derivatives of a thiol group in a compound of formula (I); or (e) an oxime or imine derivative of a carbonyl group in a compound of formula (I).

Some specific examples of prodrugs in accordance with the invention include:

(i) where the compound of formula (I) contains a carboxylic acid functionality (—COOH), an ester thereof, such as a compound wherein the hydrogen of the carboxylic acid functionality of the compound of formula (I) is replaced by $C_1$-$C_8$ alkyl (e.g. ethyl) or ($C_1$-$C_8$ alkyl)C(=O)OCH$_2$— (e.g. $^t$BuC(=O)OCH$_2$—);

(ii) where the compound of formula (I) contains an alcohol functionality (—OH), an ester thereof, such as a compound wherein the hydrogen of the alcohol functionality of the compound of formula (I) is replaced by CO($C_1$-$C_8$ alkyl) (e.g. methylcarbonyl) or the alcohol is esterified with an amino acid;

(iii) where the compound of formula (I) contains an alcohol functionality (—OH), an ether thereof, such as a compound wherein the hydrogen of the alcohol functionality of the compound of formula (I) is replaced by ($C_1$-$C_8$ alkyl)C(=O)OCH$_2$— or —CH$_2$OP(=O)(OH)$_2$;

(iv) where the compound of formula (I) contains an alcohol functionality (—OH), a phosphate thereof, such as a compound wherein the hydrogen of the alcohol functionality of the compound of formula (I) is replaced by —P(=O)(OH)$_2$ or —P(=O)(ONa)$_2$ or —P(=O)(O$^-$)$_2$Ca$^{2+}$;

(v) where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by ($C_1$-$C_{10}$)alkanoyl, —COCH$_2$NH$_2$ or the amino group is derivatised with an amino acid;

(vi) where the compound of formula (I) contains a primary or secondary amino functionality (—NH$_2$ or —NHR where R≠H), an amine thereof, for example, a compound wherein, as the case may be, one or both hydrogens of the amino functionality of the compound of formula (I) is/are replaced by —CH$_2$OP(=O)(OH)$_2$.

Certain compounds of formula (I) may themselves act as prodrugs of other compounds of formula (I). It is also possible for two compounds of formula (I) to be joined together in the form of a prodrug. In certain circumstances, a prodrug of a compound of formula (I) may be created by internally linking two functional groups in a compound of formula (I), for instance by forming a lactone.

References below to compounds of formula (I) are taken to include the compounds themselves and prodrugs thereof. The invention includes such compounds of formula (I) as well as pharmaceutically acceptable salts of such compounds and pharmaceutically acceptable solvates of said compounds and salts.

Pharmaceutically acceptable salts of the compounds of formula (I) include acid addition and base salts.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphatlene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of formula (I) may be prepared by one or more of three methods:

(i) by reacting the compound of formula (I) with the desired acid or base;

(ii) by removing an acid- or base-labile protecting group from a suitable precursor of the compound of formula (I) or by ring-opening a suitable cyclic precursor, for example, a lactone or lactam, using the desired acid or base; or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I), and pharmaceutically acceptable salts thereof, may exist in unsolvated and solvated forms. The term 'solvate' is used herein to describe a molecular complex comprising the compound of formula (I), or a pharmaceutically acceptable salt thereof, and one or more pharmaceutically acceptable solvent molecules, for example, ethanol. The term 'hydrate' may be employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of formula (I) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3$$^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to pharmaceutically acceptable salts, solvates, multi-component complexes and liquid crystals thereof and to solvates, multi-component complexes and liquid crystals of pharmaceutically acceptable salts thereof.

The compounds of formula (I) may exhibit polymorphism and/or one or more kinds of isomerism (e.g. optical, geometric or tautomeric isomerism). The compounds of formula (I) may also be isotopically labelled. Such variation is implicit to the compounds of formula (I) defined as they are by reference to their structural features and therefore within the scope of the invention.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

The pharmaceutically acceptable salts of compounds of formula (I) may also contain a counterion which is optically active (e.g. d-lactate or l-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid.

The resulting diastereomeric mixture may be separated by chromatography and/or fractional crystallization and one or both of the diastereoisomers converted to the corresponding pure enantiomer(s) by means well known to a skilled person. Chiral compounds of formula (I) (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein).

In some relevant examples herein, columns were obtained from Chiral Technologies, Inc, West Chester, Pa., USA, a subsidiary of Daicel® Chemical Industries, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature. Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed. In particular, hydrogen atoms may be replaced by deuterium atoms since such deuterated compounds are sometimes more resistant to metabolism.

Also included within the scope of the invention are active metabolites of compounds of formula (I), that is, compounds formed in vivo upon administration of the drug, often by oxidatation or dealkylation. Some examples of metabolites in accordance with the invention include (i) where the compound of formula (I) contains a methyl group, an hydroxymethyl derivative thereof ($-CH_3->-CH_2OH$):

(ii) where the compound of formula (I) contains an alkoxy group, an hydroxy derivative thereof ($-OR->-OH$);

(iii) where the compound of formula (I) contains a tertiary amino group, a secondary amino derivative thereof ($-NRR'->-NHR$ or $-NHR'$);

(iv) where the compound of formula (I) contains a secondary amino group, a primary derivative thereof ($-NHR->-NH_2$);

(v) where the compound of formula (I) contains a phenyl moiety, a phenol derivative thereof (-Ph->-PhOH); and (vi) where the compound of formula (I) contains an amide group, a carboxylic acid derivative thereof ($-CONH_2->COOH$).

For administration to human patients, the total daily dose of a compound of formula (I) is typically in the range of 0.01 mg to 500 mg depending, of course, on the mode of administration. In another embodiment of the present invention, the total daily dose of a compound of formula (I) is typically in the range of 0.1 mg to 300 mg. In yet another embodiment of the present invention, the total daily dose of a compound of formula (I) is typically in the range of 1 mg to 30 mg. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly.

In the case of dry powder inhalers and aerosols, the dosage unit is determined by means of a prefilled capsule, blister or pocket or by a system that utilises a gravimetrically fed dosing chamber. Units in accordance with the invention are typically arranged to administer a metered dose or "puff" containing from 1 to 5000 µg of drug. The overall daily dose will typically be in the range 1 µg to 20 mg which may be administered in a single dose or, more usually, as divided doses throughout the day.

A compound of formula (I) can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Compounds of formula (I) may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (I) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

Compounds of formula (I) may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques.

Compounds of the invention may also be administered topically to the skin or mucosa, that is, dermally or transdermally.

The compounds of formula (I) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. Delivery by inhalation is the preferred route of administration for the compounds of the present invention.

The pressurised container, pump, spray, atomizer, or nebuliser contains a solution or suspension of the compound of formula (I) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (I) may also be administered directly to the eye or ear, typically in the form of drops of a micronised suspension or solution in isotonic, pH-adjusted, sterile saline.

Compounds of formula (I) may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound of formula (I), may conveniently be combined in the form of a kit suitable for coadministration of the compositions. Thus, a kit of the invention comprises two or more separate pharmaceutical compositions, at least one of which contains a compound of formula (I), and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

All the compounds of formula (I) can be made by the specific and general experimental procedures described below in combination with the common general knowledge of one skilled in the art (see, for example, Comprehensive Organic Chemistry, Ed. Barton and 011 is, Elsevier; Comprehensive Organic Transformations: A Guide to Functional Group Preparations, Larock, John Wiley and Sons). In the general methods that follow, $R^1$, $R^2$, $R^3$, X and n have the meanings given in embodiment E1 described above unless otherwise stated.

Compounds of formula (I) can be made by reacting a compound of formula:

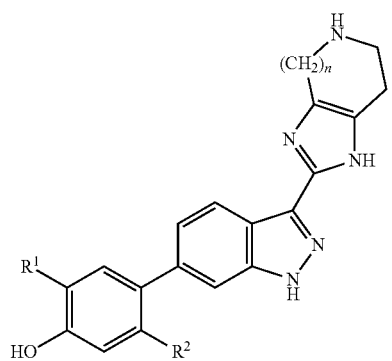

(II)

with a compound of formula:

$R^3$—X-$LG^1$ (III)

in which $LG^1$ is a suitable leaving group such as a halogen atom. The reaction will typically be carried out in a suitable inert solvent in the presence of a base such as diisopropylethylamine. When X is —$SO_2$—, for example, a sulphonyl chloride ($LG^1$=Cl) may be used. In a typical procedure, a solution of the compound of formula (II) in DMF is treated with one equivalent of the sulphonyl chloride and 1 equivalent of diisopropylethylamine and stirred at room temperature. When X is —$CH2$-, an alkyl bromide ($LG^1$=Br) may be used. In a typical procedure, a solution of the compound of formula (II) in DMF is treated with 1.1 equivalents of the alkyl bromide and 1.1 equivalents of diisopropylethylamine and stirred at 50° C. When X is CO—, an acid chloride ($LG^1$=Cl) may be used. In a typical procedure, a solution of the compound of formula (II) in DMF is treated with 1.1 equivalents of the acid chloride and 1.1 equivalents of diisopropylethylamine and stirred at room temperature.

Where X is a carbonyl group, the leaving group $LG^1$ may be created in situ from the corresponding carboxylic acid of formula $R^3$—$CO_2H$ (IV)

by using a condensation reagent such as HATU. In a typical procedure, a solution of the compound of formula (II) in DMF is treated with 1.1 equivalents of HATU and 1.1 equivalents of diisopropylethylamine and stirred at room temperature for 30 minutes. An equivalent of the acid of formula (IV) is then added. For a general review on amide bond formation, see Chem. Soc. Rev., 2009, 38(2), 606-631

Where X is —$CH_2$—, an aldehyde of formula:

$R^3$—CHO (V)

may alternatively be condensed with a compound of formula (II) under reducing conditions in order to provide the desired compound of formula (I). In a typical procedure, a solution of the compound of formula (II) in DMF is treated with the 1.5 equivalents of the aldehyde of formula (V), 2 equivalents of diisopropylethylamine and 1.5 equivalents of acetic acid and stirred at room temperature for one hour. Sodium triacetoxyborohydride (1.5 equivalents) is then added and stirring continued at room temperature.

Compounds of formula (II) can be assembled by successive aryl-heteroaryl and heteroaryl-heteroaryl organometallic coupling reactions. One example of a possible reaction sequence is shown in Scheme 1 (PG=protecting group, LG=leaving group, M=metal species; where multiple protecting groups are shown, they may be the same or different). Free NH groups will generally need to be protected during these reactions. Suitable protecting groups, their introduction and their removal are all part of the common general knowledge of the skilled person see, for instance, 'Protective Groups in Organic Chemistry' by Wuts and Greene (Wiley-Blackwell).

Suitable reaction conditions for the various steps necessary to prepare and react together the compounds in Scheme 1 may be found in the specific Preparations listed below. For a general review on organometallic cross-coupling chemistry, see 'Handbook of Organopalladium Chemistry for Organic Synthesis' (Volume 1) edited by E1-ichi Negishi (John Wiley & Sons).

Scheme 1

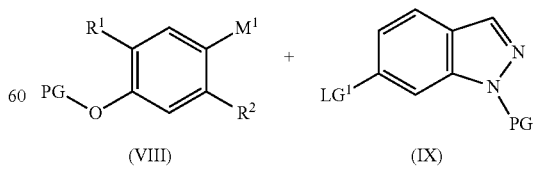

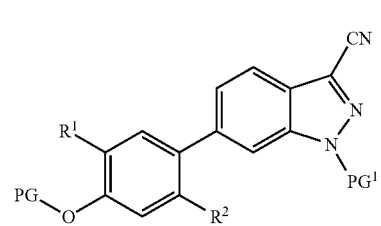

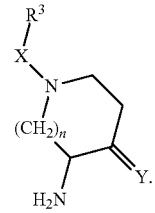

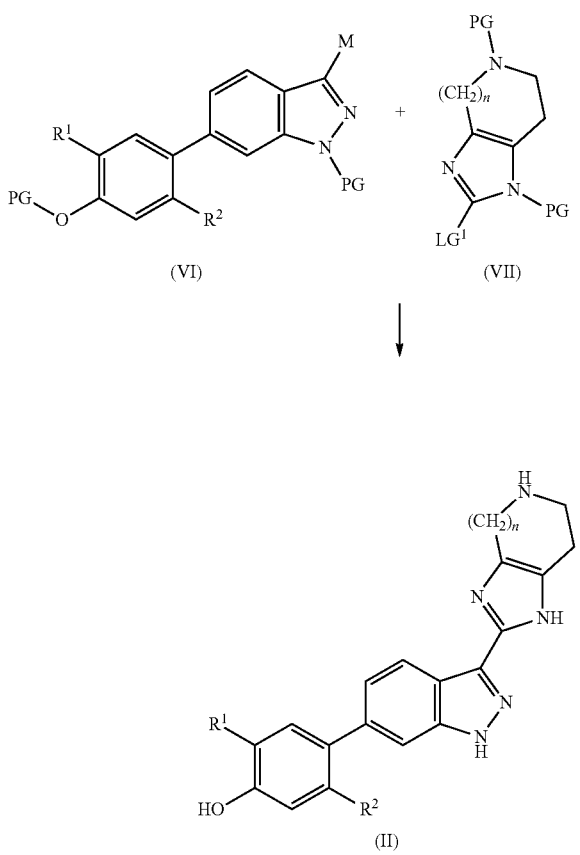

Compounds of formula (I) can also be prepared by treating a compound of formula:

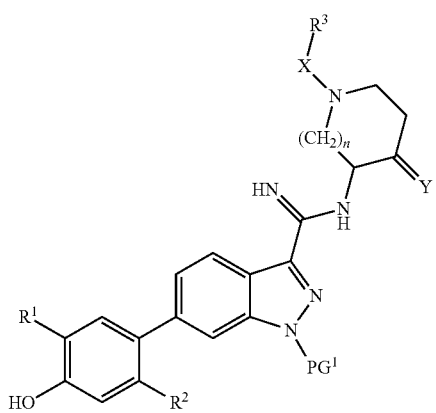

with an acid (e.g. concentrated hydrochloric acid). PG$^1$ is an acid-labile protecting group and C=Y is a carbonyl group or an acid-labile, protected form of a carbonyl group (e.g. a ketal). The reaction will usually be performed in a suitable inert solvent with heating.

Compounds of formula (X) can be made from precursors of formula:

Compounds of formula (XI) can be assembled using the aryl-heteroaryl bond forming reactions discussed above.

The skilled person will appreciate that many compounds of formula (I) may be interconverted by functional group manipulation.

The starting materials necessary for carrying out the methods described above are in many cases commercially available and may otherwise be described in the literature or in the Preparations below or may be made using analgous procedures to those described in the literature or in the Preparations below.

Supplementing the general methods presented above, the following experimental details illustrate specifically how certain compounds of formula (I) may be prepared. All Examples are compounds of formula (I). Preparations are intermediates useful in the synthesis of compounds of formula (I).

The following HPLC methods have been used in the characterization of the Examples below:

Method A

| HPLC conditions | Analytical (QC) | | Preparative | |
|---|---|---|---|---|
| Column | Gemini-NX 3 μm C18 110A | | Gemini-NX 5 μm C18 21.2 × 100 mm | |
| Temperature | Ambient | | Ambient | |
| Detection | UV 225 nm - ELSD - MS | | UV 225 nm - ELSD - MS | |
| Injection volume | 5 μL | | 1000 μL | |
| Flow rate | 1.5 mL/min | | 18 mL/min | |
| Mobile phase | A: H2O + 0.1% ammonium acetate B: MeCN + 0.1% ammonium acetate | | A: H2O + 0.1% DEA B: MeCN + 0.1% DEA | |
| | Time (min) | % B | Time (min) | % B |
| Gradient | 0 | 5 | 0-1.0 | 5 |
| | 0-3.0 | 5-95 | 1.0-7.0 | 5-98 |
| | 3.0-4.0 | 95 | 7.0-9.0 | 98 |
| | 4.0-4.1 | 95-5 | 9.0-9.10 | 98-5 |
| | 4.1-5.0 | 5 | 9.10-10 | 5 |

Method B

| HPLC conditions | Analytical (QC) | Preparative |
| --- | --- | --- |
| Column | Gemini-NX 3 μm C18 110A | Gemini-NX 5 μm C18 21.1 × 100 mm |
| Temperature | Ambient | Ambient |
| Detection | UV 225 nm - ELSD - MS | UV 225 nm - ELSD - MS |
| Injection volume | 5 μL | 1000 μL |
| Flow rate | 1.5 mL/min | 18 mL/min |
| Mobile phase | A: H2O + 0.1% formic acid<br>B: MeCN + 0.1% formic acid | A: H2O + 0.1% formic acid<br>B: MeCN + 0.1% formic acid |
|  | Time (min) / % B | Time (min) / % B |
| Gradient | 0 / 5<br>0-3.0 / 5-95<br>3.0-4.0 / 95<br>4.0-4.1 / 95-5<br>4.1-5.0 / 5 | initial / 20<br>1 / 20<br>5.4 / 70<br>6.33 / 98<br>6.4 / 20<br>7 / 20 |

Method C

| HPLC conditions | Preparative |
| --- | --- |
| Column | Phenomenex Luna C18 5 μm-100 Å 21.2 × 150 mm |
| Temperature | Ambient |
| Detection | UV 254 nm - ELSD - MS |
| Injection volume | 1000 μL |
| Flow rate | 18 mL/min |
| Mobile phase | A: H2O + 0.05% formic acid<br>B: MeCN + 0.05% formic acid |
|  | Time (min) / % B |
| Gradient | 0-2.5 / 5<br>2.5-17.5 / 5-95<br>17.5-22.5 / 95<br>22.5-22.6 / 95-5<br>22.6-23.0 / 5 |

Method D

| HPLC conditions | Preparative |
| --- | --- |
| Column | Zorbax SB C18 5 μm-100 Å 21.2 × 150 mm |
| Temperature | Ambient |
| Detection | UV 254 nm - ELSD - MS |
| Injection volume | 1000 μL |
| Flow rate | 20 mL/min |
| Mobile phase | A: H2O + 0.05% NH4OAc<br>B: MeCN + 0.05% NH4OAc |
|  | Time (min) / % B |
| Gradient | 0-2.5 / 5<br>2.5-17.5 / 5-95<br>17.5-22.5 / 95<br>22.5-22.6 / 95-5<br>22.6-23.0 / 5 |

Method E

| HPLC conditions | Preparative |
| --- | --- |
| Column | Luna Phenyl-Hexyl 5 μm-100 Å 21.2 × 150 mm |
| Temperature | Ambient |
| Detection | UV 254 nm - ELSD - MS |
| Injection volume | 1000 μL |
| Flow rate | 20 mL/min |
| Mobile phase | A: H2O + 0.05% NH4OAc<br>B: MeCN + 0.05% NH4OAc |
|  | Time (min) / % B |
| Gradient | 0-2.5 / 5<br>2.5-17.5 / 5-95<br>17.5-22.5 / 95<br>22.5-22.6 / 95-5<br>22.6-23.0 / 5 |

Method F

| HPLC conditions | Preparative |
| --- | --- |
| Column | Xterra RP18 19-250 mm |
| Temperature | Ambient |
| Detection | UV 254 nm - ELSD - MS |
| Injection volume | 1000 μL |
| Flow rate | 16 mL/min |
| Mobile phase | A: H2O + 0.05% NH4OAc<br>B: MeCN + 0.05% NH4OAc |
|  | Time (min) / % B |
| Gradient | 0-2.5 / 5<br>2.5-17.5 / 5-95<br>17.5-22.5 / 95<br>22.5-22.6 / 95-5<br>22.6-25.0 / 5 |

Method G

| HPLC conditions | Preparative |
| --- | --- |
| Column | Sunfire C18 30 × 100 mm 5u |
| Temperature | Ambient |
| Detection | UV 254 nm - ELSD - MS |
| Injection volume | 1000 μL |
| Flow rate | 16 mL/min |
| Mobile phase | A: H2O + 0.05% NH4OAc<br>B: MeCN + 0.05% NH4OAc |

-continued

| HPLC conditions | Preparative | |
|---|---|---|
| | Time (min) | % B |
| Gradient | 0-2.5 | 5 |
| | 2.5-17.5 | 5-95 |
| | 17.5-22.5 | 95 |
| | 22.5-22.6 | 95-5 |
| | 22.6-25.0 | 5 |

Example 1

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-fluoro-phenyl)-methanone To a solution of 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 μmol) in DMF (1 mL), was added HATU (32 mg, 84 μmol), and DIPEA (56 μL, 320 μmol). The reaction mixture was stirred at room temperature for 30 minutes. 4-Fluoro-benzoic acid (11.2 mg, 80 μmol) was added to the reaction mixture and stirring was continued for 18 hours. Saturated aqueous sodium hydrogen carbonate solution (5 mL) was added to the reaction mixture. The resulting solid was collected by filtration, washing with further saturated aqueous sodium hydrogen carbonate solution. The crude material was purified by HPLC Method B to afford 7.7 mg of the title compound.
LCMS (Method A): RT 2.52 min (100% area), ES m/z 500.182 [M+H]$^+$.

Example 2

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone The title compound was prepared from 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 μmol) and isothiazole-3-carboxylic acid (11 mg, 80 μmol) using the same method as described in Example 1. The crude material was purified by HPLC Method A to afford 7.7 mg of the title compound.
LCMS (Method A) RT 2.39 min (100% area), ES m/z 489.143 [M+H]$^+$.

Example 3

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone To a solution of N-(1-benzyl-4,4-diethoxy-piperidin-3-yl)-6-(2-ethyl-5-fluoro-4-hydroxy-phenyl)-1-(tetrahydro-pyran-2-yl)-1H-indazole-3-carboxamidine (Preparation 9, 6.06 g, 9.41 mmol) in ethanol (34 mL) was added concentrated hydrochloric acid (12M, 15.8 mL, 189 mmol). The reaction mixture was heated at 65° C. for 18 hours. The reaction mixture was concentrated in vacuo and recharged with fresh ethanol (34 mL) and concentrated hydrochloric acid (12M, 15.8 mL, 189 mmol). The reaction mixture was heated at 65° C. for a further 4 hours. Water (20 mL) was added to the reaction mixture at 65° C. and then the reaction was allowed to cool slowly to room temperature. The solvents were removed in vacuo and the residue was partitioned between 2-MeTHF (200 mL) and saturated sodium hydrogen carbonate aqueous solution (100 mL). The organic layer was washed with further saturated sodium hydrogen carbonate aqueous solution (100 mL). The combined aqueous layers were re-extracted with 2-MeTHF (250 mL). The combined organic layers were dried over MgSO$_4$ and concentrated in vacuo to yield a brown foam. The crude material was dissolved in MeCN (150 mL) and ethanol (30 mL) and heated at 50° C. for 2 days. The product crystallised from this solution and was collected by filtration and dried in vacuo to give the title compound as a crystalline white solid (3.53 g) in an 80% yield.
$^1$H NMR (400 MHz, CD$_3$OD) δ ppm 1.04 (t, 3H), 2.52 (q, 2H), 2.81 (t, 2H), 2.91 (t, 2H), 3.62 (s, 2H), 3.80 (s, 2H), 6.87 (d, 1H), 6.92 (d, 1H), 7.11 (d, 1H), 7.26-7.43 (m, 6H), 8.22 (d, 1H).
LCMS: m/z 468 [M+H]$^+$, 466 [M−H]$^−$.

Example 4

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-piperidin-1-yl-pyrazin-2-yl)-methanone To a solution of 5-piperidin-1-yl-pyrazine-2-carboxylic acid (Preparation 43, 10.7 g, 51.8 mmol) in DMF (200 mL) was added DIPEA (24.6 mL, 141 mmol) and HATU (21.5 g, 56.5 mmol) and the resulting mixture was stirred at room temperature for 10 minutes before being added dropwise to a suspension of 5-ethyl-2-fluoro-4-[3-(4,5,6,7-tetrahydro-1H-imidazo[4,5-c]pyridin-2-yl)-1H-indazol-6-yl]-phenol dihydrochloric acid salt (Preparation 11, 19.5 g, 47.1 mmol) in DMF (200 mL) over 30 minutes, using a further 75 mL DMF to wash the vessel. The reaction mixture was then stirred at room temperature for 18 hours. A further portion of 5-piperidin-1-yl-pyrazine-2-carboxylic acid (1.07 g, 5.18 mmol) in DMF (40 mL) was treated with DIPEA (2.46 mL, 14.1 mmol) and activated with HATU (2.15 g, 5.65 mmol) and the resulting mixture was stirred at room temperature for 10 minutes before being added to the original reaction mixture which was then stirred for a further 4 hours at room temperature. The reaction mixture was poured onto water (1.2 L) and the pH was adjusted to 7 with sodium hydroxide solution. The resulting suspension was stirred at room temperature for 30 minutes. The precipitate was collected by filtration, washed with water (400 mL) and then dried under vacuum. The crude material was dissolved in ethanol (113 mL) and treated with a 1M aqueous solution of sodium hydroxide. The reaction mixture was stirred at room temperature for 18 hours. The precipitate was collected by filtration, washed with a cold solution of 1:3 1M sodium hydroxide:ethanol (100 mL) and dried under vacuum to give the sodium salt of the title compound, 16.14 g. This material was dissolved in water (100 mL) and treated with a 10% aqueous solution of citric acid (10 mL) to adjust the pH to 4. A few drops of 1M sodium hydroxide solution were added to bring the pH to 7. The resulting suspension was stirred at room temperature for 1 hour and the solid was collected by filtration, washed with water and then dried under vacuum to give the title compound as a white solid (13.864 g) in an 89% yield.
$^1$H NMR (400 MHz, DMSO-d6) δ ppm 0.94 (t, 3H), 1.54-1.60 (m, 2H), 1.60-1.67 (m, 2H), 2.38 (q, 2H), 2.71-2.83 (m, 2H), 3.64-3.71 (m, 4H), 3.85-3.98 (m, 4H), 4.63-4.78 (m, 2H), 6.66 (d, 1H), 6.73 (d, 1H), 7.00-7.08 (m, 1H), 7.16-7.24 (m, 1H), 816-8.25 (m, 1H), 8.29 (s, 1H), 8.37 (s, 1H).
LCMS: m/z 567 [M+H]$^+$, 565 [M−H]$^-$ Example 5

{2-[6-(2-Ethyl-5-fluoro-4-hydroxy-phenyl)-1H-indazol-3-yl]-1,4,6,7-tetrahydro-imidazo[4,5-c]pyridin-5-yl}-(6-bhenoxy-pyridin-3-yl)-methanone The title compound was prepared from 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 μmol) and 6-phenoxy-nicotinic acid (17 mg, 80 μmol) using the method of Example 1. The crude material was purified by HPLC Method A to afford 3.1 mg of the title compound.
LCMS (Method A): RT 2.67 min (100% area), ES m/z 575.213 [M+H]$^+$.

Example 6

5-Ethyl-2-fluoro-4-{3-[5-(6-morpholin-4-yl-pyridine-3-sulfonyl)-4,5,6,7-tetrahydro-1H-imidazo[4,5-c]pyridin-2-yl]-1H-indazol-6-yl}-phenol To a solution of 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 μmol) in DMF (1 mL), was added 6-morpholin-4-yl-pyridine-3-sulfonyl chloride (21 mg, 80 μmol) and DIPEA (56 μL, 320 μmol). The reaction mixture was stirred at room temperature for 18 hours. Saturated aqueous sodium hydrogen carbonate solution (5 mL) was added and the resulting solid was collected by filtration and washed with further saturated aqueous sodium hydrogen carbonate solution. The crude material was purified by HPLC Method A to afford 18.7 mg of the title compound.
LCMS (Method A): RT 2.58 min (100% area), ES m/z 602.206 [M−H]$^-$.

Example 7

5-Ethyl-2-fluoro-4-{3-[5-(6-phenoxy-pyridine-3-sulfonyl)-4,5,6,7-tetrahydro-1H-imidazo[4,5-c]pyridin-2-yl]-1H-indazol-6-yl}-phenol The title compound was prepared from 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 μmol) and 6-phenoxy-pyridine-3-sulfonyl chloride (22 mg, 80 μmol) using the method of Example 6. The crude material was purified by HPLC Method A to afford 8.4 mg of the title compound.
LCMS (Method A): RT 2.82 min (100% area), ES m/z 611.18 [M+H]$^+$.

Example 8

(5-Chloro-pyridin-2-yl)-{2-[6-(2-ethyl-5-fluoro-4-hydroxy-phenyl)-1H-indazol-3-yl]-4,5,7,8-tetrahydro-1H-imidazo[4,5-d]azebin-6-yl}-methanone To a solution of 5-chloro-pyridine-2-carboxylic acid (13.2 mg, 85 μmol) in DMF (1 mL) was added HATU (32 mg, 85 μmol) and the resulting reaction mixture was stirred at room temperature for 30 minutes. 5-Ethyl-2-fluoro-4-[3-(1,4,5,6,7,8-hexahydro-imidazo[4,5-d]azepin-2-yl)-1H-indazol-6-yl]-phenol trihydrobromide salt (Preparation 32, 50 mg, 80 μmol) and DIPEA (56 μL, 320 μmol) were added and stirring was continued at room temperature for 18 hours. Saturated aqueous sodium hydrogen carbonate solution (5 mL) was added to the reaction mixture. The resulting solid was collected by filtration and washed with further saturated aqueous sodium hydrogen carbonate solution. The crude material was purified by HPLC Method A to afford 20.5 mg of the title compound.
LCMS (Method A): RT 2.76 min (100% area), ES m/z 531.163 [M−H]$^-$.

Example 9

2-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-isonicotinonitrile The title compound was prepared from 4-cyano-pyridine-2-carboxylic acid (12.5 mg, 85 μmol) and 5-ethyl-2-fluoro-4-[3-(1,4,5,6,7,8-hexahydro-imidazo[4,5-d]azepin-2-yl)-1H-indazol-6-yl]-phenol trihydrobromide salt (Preparation 32, 50 mg, 80 μmol) using the method of Example 8. The crude material was purified by HPLC Method B to afford 6.5 mg of the title compound.
LCMS (Method A): RT 2.66 min (100% area), ES m/z 522.198 [M+H]$^+$.

Example 10

{2-[6-(2-Ethyl-5-fluoro-4-hydroxy-phenyl)-1H-indazol-3-yl]-4,5,7,8-tetrahydro-1H-imidazo[4,5-d]azepin-6-yl}-(4-fluoro-phenyl)-methanone The title compound was prepared from 4-fluoro-benzoic acid (12.5 mg, 85 μmol) and 5-ethyl-2-fluoro-4-[3-(1,4,5,6,7,8-hexahydro-imidazo[4,5-d]azepin-2-yl)-1H-indazol-6-yl]-phenol trihydrobromide salt (Preparation 32, 50 mg, 80 μmol) using the method of Example 8. The crude material was purified by HPLC Method B to afford 14.5 mg of the title compound.
LCMS (Method A): RT 2.76 min (100% area), ES m/z 514.198 [M+H]$^+$.

Example 11

{2-[6-(2-Ethyl-5-fluoro-4-hydroxy-phenyl)-1H-indazol-3-yl]-4,5,7,8-tetrahydro-1H-imidazo[4,5-d]azepin-6-yl}-isothiazol-3-yl-methanone The title compound was prepared from isothiazole-3-carboxylic acid (11 mg, 85 μmol) and 5-ethyl-2-fluoro-4-[3-(1,4,5,6,7,8-hexahydro-imidazo[4,5-d]azepin-2-yl)-1H-indazol-6-yl]-phenol trihydrobromide salt (Preparation 32, 50 mg, 80 μmol) using the method of Example 8. The crude material was purified by HPLC Method B to afford 10.3 mg of the title compound.
LCMS (Method A): RT 2.54 min (100% area), ES m/z 503.159 [M+H]$^+$.

Example 12

5-Ethyl-2-fluoro-4-{3-[5-(4-fluoro-benzenesulfonyl)-4,5,6,7-tetrahydro-1H-imidazo[4,5-c]pyridin-2-yl]-1H-indazol-6-yl}-phenol To a solution of 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 µmol) in DMF (1 mL), was added 4-fluoro-benzenesulfonyl chloride (16 mg, 80 µmol), and DIPEA (56 µL, 320 µmol). The reaction mixture was stirred at room temperature for 4 hours. Saturated aqueous sodium hydrogen carbonate solution (5 mL) was added to the reaction mixture. The resulting solid was collected by filtration and washed with further saturated aqueous sodium hydrogen carbonate solution. The crude material was purified by reverse phase chromatography (Method C) to afford 7 mg of the title compound.

$^1$H NMR (400 MHz, CD$_3$OD) δ ppm 1.02 (t, 3H), 2.52 (q, 2H), 3.78-3.81 (m, 2H), 4.37-4.29 (m, 2H), 6.88-6.96 (m, 2H), 7.15 (d, 1H), 7.32-7.36 (m, 2H), 7.40 (s, 1H), 7.89-7.95 (m, 2H), 8.21 (d, 1H)

LCMS: m/z 536 [M+H]$^+$.

Example 13

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-fluoro-phenoxy)-Dvrazin-2-yl]-methanone To a solution of 5-(2-fluoro-phenoxy)-pyrazine-2-carboxylic acid (Preparation 45, 19 mg, 80 µmol) in DMF (1 mL) was added HBTU (32 mg, 85 µmol) and the resulting reaction mixture was stirred at room temperature for 30 minutes. 5-Ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 µmol) and DIPEA (56 µL, 320 µmol) were added and stirring was continued at room temperature for 18 hours. Saturated aqueous sodium hydrogen carbonate solution (5 mL) was added to the reaction mixture. The resulting solid was collected by filtration and washed with further saturated aqueous sodium hydrogen carbonate solution. The crude material was purified by HPLC Method B to afford 8.3 mg of the title compound.

LCMS (Method A): RT 2.97 min (100% area), ES m/z 594.199 [M−H]$^-$.

Example 14

4-[3-(6-Benzyl-1,4,5,6,7,8-hexahydro-imidazo[4,5-d]azepin-2-yl)-1H-indazol-6-yl]-5-ethyl-2-fluoro-phenol To a solution of 5-ethyl-2-fluoro-4-[3-(1,4,5,6,7,8-hexahydro-imidazo[4,5-d]azepin-2-yl)-1H-indazol-6-yl]-phenol trihydrobromide salt (Preparation 32, 50 mg, 80 µmol) in DMF (1 mL), was added benzyl bromide (14.4 mg, 10 µL, 85 µmol), and DIPEA (56 µL, 320 µmol). The reaction mixture was heated at 50° C. for 18 hours. The reaction mixture was then cooled to room temperature and partitioned between EtOAc (50 mL) and water (50 mL). The organic layer was washed with brine (50 mL), dried over sodium sulfate and concentrated in vacuo to furnish a brown oil. The crude material was purified by reverse phase chromatography (Method C) to afford 4 mg of the title compound.

$^1$H NMR (400 MHz, CD$_3$OD) δ ppm 1.02 (t, 3H), 2.55 (q, 2H), 3.08-3.11 (m, 4H), 3.34-3.38 (m, 4H), 4.23 (s, 2H), 6.88-6.94 (m, 2H), 7.18 (d, 1H), 7.41-7.4 (m, 3H), 7.52-7.55 (m, 2H), 8.20 (d, 1H), 8.39 (br s, 1H).

LCMS: m/z 482 [M+H]$^+$, 480 [M−H]$^-$.

Example 15

(5-Chloro-pyridin-2-yl)-{2-[6-(2-ethyl-5-fluoro-4-hydroxy-phenyl)-1H-indazol-3-yl]-1,4,6,7-tetrahydro-imidazo[4,5-d]pyridin-5-yl}-methanone To a solution of 5-chloro-pyridine-2-carboxylic acid (12 mg, 80 µmol) in DMF (1 mL) was added HBTU (32 mg, 85 µmol) and the resulting reaction mixture was stirred at room temperature for 30 minutes. 5-Ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 µmol) and DIPEA (56 µL, 320 µmol) were added and stirring was continued at room temperature for 18 hours. Saturated aqueous sodium hydrogen carbonate solution (5 mL) was added to the reaction mixture. The resulting solid was collected by filtration and washed with further saturated aqueous sodium hydrogen carbonate solution. The crude material was purified by reverse phase chromatography (Method C) to afford 3.3 mg of the title compound.

$^1$H NMR (400 MHz, CD$_3$OD) δ ppm 1.02 (t, 3H), 2.52 (q, 2H), 2.88-2.96 (m, 2H), 3.79-3.82 (m, 2H), 4.15-4.19 (m, 2H), 6.82-6.96 (m, 2H), 7.08-7.18 (m, 1H), 7.39-7.41 (m, 1H), 7.69-7.71 (m, 1H), 7.99-8.01 (m, 1H), 8.19-8.21 (d, 1H), 8.38-8.42 (m, 1H).

LCMS: m/z 517 [M+H]$^+$, 515 [M−H]$^-$.

Example 16

5-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-pyridine-2-carbonitrile To a solution of 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 80 µmol) in DMF (1 mL), was added 6-cyano-nicotinoyl chloride (Preparation 46, 17 mg, 96 µmol), and DIPEA (56 µL, 320 µmol). The reaction mixture was stirred at room temperature for 72 hours and then saturated aqueous sodium hydrogen carbonate solution (5 mL) was added. The resulting solid was collected by filtration and washed with further saturated aqueous sodium hydrogen carbonate solution. The crude material was purified by reverse phase chromatography (Method C) to afford 6.9 mg of the title compound.

$^1$H NMR (400 MHz, CD$_3$OD) δ ppm 1.02 (t, 3H), 2.52 (q, 2H), 2.85-2.98 (m, 2H), 3.75-3.79 (m, 2H), 4.15-4.19 (m, 2H), 6.82-6.96 (m, 2H), 7.08-7.18 (m, 1H), 7.38-7.40 (m, 1H), 8.00 (d, 1H), 8.15-8.20 (m, 2H), 8.22 (d, 1H).

LCMS: m/z 508 [M+H]$^+$, 506 [M−H]$^-$.

Example 17

5-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-pyridine-2-carbonitrile To a solution of 5-ethyl-2-fluoro-4-[3-(1,4,5,6,7,8-hexahydro-imidazo[4,5-d]azepin-2-yl)-1H-indazol-6-yl]-phenol trihydrobromide salt (Preparation 32, 28 mg, 44 µmol) in DMF (1 mL), was added 6-cyano-nicotinoyl chloride (Preparation 46, 20.9 mg, 141 µmol), and DIPEA (31 µL, 176 µmol). The reaction mixture was stirred at room temperature for 18 hours and then saturated aqueous sodium hydrogen carbonate solution (5 mL) was added. The resulting solid was collected by filtration and washed with further saturated aqueous sodium hydrogen carbonate solution. The crude material was purified by HPLC Method A to afford 10.3 mg of the title compound.

LCMS (Method A): RT 2.69 min (100% area), ES m/z 522.198 [M−H]−.

Example 18

5-Ethyl-2-fluoro-4-[3-(5-quinolin-6-ylmethyl-4,5,6,7-tetrahydro-1H-imidazo[4,5-c]pyridin-2-yl)-1H-indazol-6-yl]-phenol To a solution of 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) in DMF (1 mL), was added quinoline-6-carbaldehyde (31 mg, 198 µmol), DIPEA (34 mg, 46 µL, 264 µmol) and AcOH (11.8 mg, 11 µL, 198 µmol). The reaction mixture was stirred at room temperature for 1 hour. STAB (42 mg, 198 µmol) was added and stirring was continued for 18 hours. The reaction mixture was partitioned between EtOAc (10 mL) and saturated aqueous sodium hydrogen carbonate solution (10 ml). The organic layer was washed with further saturated aqueous sodium hydrogen carbonate solution (2×10 mL), dried over magnesium sulfate and concentrated in vacuo to furnish a brown oil. The crude material was purified by HPLC Method A to afford 20.6 mg of the title compound.

LCMS (Method A): RT 2.59 min (100% area), ES m/z 519.223 [M−H]−.

Example 19

5-Ethyl-2-fluoro-4-{3-[5-(4-hydroxy-benzyl)-4,5,6,7-tetrahydro-1H-imidazo[4,5-c]pyridin-2-yl]-1H-indazol-6-yl}-phenol The title compound was prepared from 4-hydroxy-benzaldehyde (24.2 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 18. The crude material was purified by HPLC Method A to afford 31.4 mg of the title compound.

LCMS (Method A): RT 2.32 min (100% area), ES m/z 482.207 [M−H]−.

Example 20

5-Ethyl-2-fluoro-4-{3-[5-(3-hydroxy-benzyl)-4,5,6,7-tetrahydro-1H-imidazo[4,5-c]pyridin-2-yl]-1H-indazol-6-yl}-phenol The title compound was prepared from 3-hydroxy-benzaldehyde (24.2 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 18. The crude material was purified by HPLC Method A to afford 39.6 mg of the title compound.

LCMS (Method A): RT 2.39 min (100% area), ES m/z 484.207 [M+H]+.

Example 21

4-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile The title compound was prepared from 4-formyl-pyridine-2-carbonitrile (26 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 18. The crude material was purified by HPLC Method B to afford 16 mg of the title compound.

LCMS (Method B): RT 1.75 min (100% area), ES m/z 494.203 [M+H]+.

Example 22

5-Ethyl-2-fluoro-4-{3-[5-(3-methoxy-benzyl)-4,5,6,7-tetrahydro-1H-imidazo[4,5-c]pyridin-2-yl]-1H-indazol-6-yl}-phenol formic acid salt To a solution of 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) in DMF (1 mL), was added 3-methoxy-benzaldehyde (27 mg, 198 µmol), DIPEA (34 mg, 46 µL, 264 µmol) and AcOH (11.8 mg, 11 µL, 198 µmol). The reaction mixture was stirred at room temperature for 1 hour. STAB (42 mg, 198 µmol) was added and stirring was continued for 18 hours. Saturated aqueous sodium hydrogen carbonate solution (5 ml) was added to the reaction mixture. The resulting solid was collected by filtration and washed with further saturated aqueous sodium hydrogen carbonate solution. The crude material was purified by HPLC Method B to afford 30.1 mg of the title compound.

LCMS (Method A): RT 2.64 min (100% area), ES m/z 496.223 [M−H]−.

Example 23

5-Ethyl-2-fluoro-4-[3-(5-quinolin-3-ylmethyl-4,5,6,7-tetrahydro-1H-imidazo[4,5-c]pyridin-2-yl)-1H-indazol-6-yl]-phenol The title compound was prepared from quinoline-3-carbaldehyde (31 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 22. The crude material was purified by HPLC Method B to afford 14.3 mg of the title compound.

LCMS (Method A): RT 2.59 min (100% area), ES m/z 519.223 [M+H]+.

Example 24

5-Ethyl-2-fluoro-4-{3-[5-(6-phenoxy-pyridin-3-ylmethyl)-4,5,6,7-tetrahydro-1H-imidazo[4,5-c]pyridin-2-yl]-1H-indazol-6-yl}-phenol The title compound was prepared from 6-phenoxy-pyridine-3-carbaldehyde (39 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 22. The crude material was purified by HPLC Method A to afford 24.7 mg of the title compound.

LCMS (Method B): RT 2.53 min (100% area), ES m/z 561.234 [M+H]$^+$.

Example 25

5-Ethyl-2-fluoro-4-{3-[5-(3,4,5,6-tetrahydro-2H-[1, 2']bipyridinyl-5'-ylmethyl)-4,5,6,7-tetrahydro-1H-imidazo[4,5-c]pyridin-2-yl]-1H-indazol-6-yl}-phenol The title compound was prepared from 3,4,5,6-tetrahydro-2H-[1,2']bipyridinyl-5'-carbaldehyde (38 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 22. The crude material was purified by HPLC Method A to afford 22.1 mg of the title compound.

LCMS (Method B): RT 2.22 min (100% area), ES m/z 552.281 [M+H]$^+$.

Example 26

3-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile The title compound was prepared from 3-formyl-pyridine-2-carbonitrile (26 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 22. The crude material was purified by HPLC Method A to afford 14.9 mg of the title compound.

LCMS (Method A): RT 1.46 min (100% area), ES m/z 494.203 [M+H]$^+$.

Example 27

5-Ethyl-2-fluoro-4-{3-[5-(4-fluoro-benzyl)-4,5,6,7-tetrahydro-1H-imidazo[4,5-c]pyridin-2-yl]-1H-indazol-6-yl}-phenol The title compound was prepared from 4-fluoro-benzaldehyde (25 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 22. The crude material was purified by HPLC Method A to afford 3.4 mg of the title compound.

LCMS (Method A): RT 2.77 min (100% area), ES m/z 486.203 [M+H]$^+$.

Example 28

5-Ethyl-2-fluoro-4-[3-(5-[1,8]naphthyridin-2-ylmethyl-4,5,6,7-tetrahydro-1H-imidazo[4,5-c]pyridin-2-yl)-1H-indazol-6-yl]-phenol The title compound was prepared from [1,8]naphthyridine-2-carbaldehyde (31 mg, 198 µmol) and 5-ethyl-2-fluoro-4-[3-(4,5,6,7-tetrahydro-1H-imidazo[4,5-c]pyridin-2-yl)-1H-indazol-6-yl]-phenol trihydrobromide salt (Preparation 25, 50 mg, 132 µmol) using the method of Example 22. The crude material was purified by HPLC Method B to afford 22.5 mg of the title compound.

LCMS (Method B): RT 2.28 min (100% area), ES m/z 520.218 [M+H]$^+$.

Example 29

(2-{6-[5-Fluoro-4-hydroxy-2-(2,2,2-trifluoro-ethyl)-pheny]-1H-indazol-3-yl}-1,4,6,7-tetrahydro-imidazo[4,5-c]pyridin-5-yl)-(5-piperidin-1-yl-pyrazin-2-yl)-methanone diethylamine salt The title compound was prepared from 5-piperidin-1-yl-pyrazine-2-carboxylic acid (Preparation 44, 35 mg, 168 µmol) and 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (Preparation 39, 100 mg, 168 µmol) using the method of Example 8. The crude material was purified by HPLC Method A to afford 29.0 mg of the title compound as the diethylamine salt.

LCMS (Method B): RT 2.66 min (100% area), ES m/z 621.227 [M+H]$^+$.

Example 30

(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(4-fluoro-phenyl)-methanone diethylamine salt The title compound was prepared from 4-fluoro-benzoic acid (24 mg, 168 µmol) and 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (Preparation 39, 100 mg, 168 µmol) using the method of Example 8. The crude material was purified by HPLC Method A to afford 33.3 mg of the title compound.

LCMS (Method B): RT 2.62 min (100% area), ES m/z 554.154 [M+H]$^+$.

Example 31

4-[3-(5-Benzyl-4,5,6,7-tetrahydro-1H-imidazo[4,5-c]pyridin-2-yl)-1H-indazol-6-yl]-2-fluoro-5-(2,2,2-trifluoro-ethyl)-phenol diethylamine salt To a solution of 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (Preparation 39, 100 mg, 168 µmol) in DMF (1 mL), was added benzyl bromide (28.8 mg, 20 µL, 168 µmol), and DIPEA (120 µL, 672 µmol). The reaction mixture was heated at 80° C. for 3 hours. The reaction mixture was then cooled to room temperature and saturated aqueous sodium hydrogen carbonate solution (5 mL) was added. The resulting solid was collected by filtration and washed with further saturated aqueous sodium hydrogen carbonate solution. The crude material was purified by HPLC Method A to afford 10.6 mg of the title compound.

LCMS (Method A): RT 2.67 min (100% area), ES m/z 522.184 [M+H]$^+$.

Example 32

{5-[(2-Dimethylamino-ethyl)-methyl-amino]-pyrazin-2-yl}-{2-[6-(2-ethyl-5-fluoro-4-hydroxy-phenyl)-1H-indazol-3-yl]-1,4,6,7-tetrahydro-imidazo[4,5-c]pyridin-5-yl}-methanone To a solution of (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone (80 mg, 0.154 mmol) in DMSO (1 mL) were added DIPEA (0.08 mL, 0.463 mmol) and N,N,N-trimethylethylendiamine (31.56 mg, 0.308 mmol) and the mixture stirred at room temperature for 18 hours. The crude reaction mass was purified by prep-HPLC Method C to afford the title compound as an off white solid (25 mg, 28%).

1H NMR (400 MHz, DMSO) δ (ppm): 1.01 (t, 3H), 2.18 (s, 6H), 2.44 (m, 4H), 2.78 (bs, 2H), 3.13 (s, 3H), 3.70 (t, 3H), 3.94 (bs, 2H), 4.66-4.76 (m, 2H), 6.90 (d, 1H), 7.00 (d, 1H), 7.09 (d, 1H), 7.37 (s, 1H), 8.12 (s, 1H), 8.31 (d, 1H), 8.38 (d, 1H), 12.51 (s, 1H), 13.21 (s, 1H);

LCMS: Rt=2.59 min; m/z 584[M+H]+

Example 33

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-pyrrolidin-1-yl-ethylamino)-pyrazin-2-yl]-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (50 mg, 96 μmol) and (2-(pyrrolidin-1-yl) ethanamine, 50 mg, 132 μmol) using the method of Example 32. The crude material was purified by HPLC Method E to afford (30 mg, 52%) of the title compound.

1H NMR (400 MHz, DMSO) δ (ppm): 0.98-1.01 (t, 3H), 1.13 (s, 3H), 1.22 (bs, 2H), 1.68 (bs, 3H), 1.90 (s, 1H), 2.11 (s, 1H), 2.60 (t, 2H), 2.78 (bs, 3H), 3.42 (m, 2H), 3.91 (bs, 2H), 4.64-4.68 (m, 2H), 6.90 (d, 1H), 7.00 (d, 1H), 7.08 (d, 1H), 7.36 (s, 1H), 7.60 (bs, 1H), 7.95 (s, 1H), 8.29-8.33 (m, 2H), 9.80 (bs, 1H), 12.52 (s, 1H), 13.22 (s, 1H);

LCMS: Rt=5.71 min; m/z 596.4[M+H]+.

Example 34

[5-(2-Dimethylamino-ethylamino)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (100 mg, 193 μmol) and N,N-dimethylethylendiamine, (34 mg, 386 μmol) using the method of Example 32. The crude material was purified by HPLC Method E to afford (50 mg, 46%) of the title compound as white solid.

1H NMR (400 MHz, DMSO) δ (ppm): 1.03 (t, 3H), 2.18 (s, 6H), 2.40-2.45 (m, 4H), 2.77 (bs, 2H), 2.93-2.98 (m, H), 3.16 (s, 3H), 3.38-3.44 (m, 2H), 3.78 (m, 2H), 4.66 (m, 2H), 6.90 (d, 1H), 6.99 (d, 1H), 7.09 (d, 1H), 7.37 (s, 1H), 7.53 (bs, 1H), 7.96 (s, 1H), 8.29 (s, 2H):

LCMS: Rt=2.53 min; m/z 570[M+H]+.

Example 35

[5-(4-Dimethylamino-piperidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 μmol) and 4-N,N-dimethylaminopiperidine, (40 mg, 308 μmol) using the method of Example 32. The crude material was purified by HPLC Method C to afford (60 mg, 64%) of the title compound as off-white solid.

1H NMR (400 MHz, DMSO) δ (ppm): 1.01 (t, 3H), 1.39-1.41 (m, 2H), 1.83-1.86 (m, 2H), 2.18 (s, 6H), 2.32-2.38 (m, 2H), 2.78 (bs, 2H), 2.95-3.01 (t, 2H), 3.90 (s, 2H), 3.92-3.94 (m, 2H), 4.42-4.45 (m, 2H), 4.67-4.75 (m, 2H), 6.87 (d, 1H), 6.92 (d, 1H), 7.03 (bs, 1H), 7.37 (s, 1H), 8.33-8.39 (m, 3H), 12.50 (bs, 1H), 13.22 (bs, 1H);

LCMS: Rt=5.46 min; m/z 610.4[M+H]+

Example 36

{2-[6-(2-Ethyl-5-fluoro-4-hydroxy-phenyl)-1H-indazol-3-yl]-1,4,6,7-tetrahydro-imidazo[4,5-c]pyridin-5-yl}-{5-[ethyl-(2-hydroxy-ethyl)-amino]-pyrazin-2-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (120 mg, 231 μmol) and N-ethylaminoethanol, (41 mg, 463 μmol) using the method of Example 32. The crude material was purified by HPLC Method D to afford (60 mg, 64%) of the title compound as off-white solid.

1H NMR (400 MHz, DMSO) δ (ppm): 0.99-1.03 (t, 3H), 1.13-1.16 (t, 3H), 2.32-2.41 (m, 2H), 2.78 (bs, 2H), 2.94-2.97 (m, 1H), 3.61 (bs, 5H), 3.94 (m, 2H), 4.65-4.86 (m, 3H), 6.90 (d, 1H), 7.00 (d, 1H), 7.09 (bs, 1H), 7.36 (s, 1H), 8.14 (s, 1H), 8.31-8.38 (m, 2H), 9.82 (bs, 1H), 12.51 (bs, 1H), 13.20 (bs, 1H);

LCMS: Rt=2.69 min; m/z 571.4[M+H]+.

Example 37

[5-((R)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 μmol) and (R)-3-dimethylaminopyrrolidine, (35 mg, 308 μmol) using the method of Example 32. The crude material was purified by HPLC Method C to afford (35 mg, 38%) of the title compound as white solid.

1H NMR (400 MHz, DMSO) δ (ppm): 1.03 (t, 3H), 1.75 (m, 2H), 2.21 (s, 6H), 2.79-2.81 (m, 3H), 3.20 (m, 2H), 3.41-3.47 (m, 2H), 3.71 (m, 1H), 3.77-3.81 (m, 1H), 3.92 (bs, 2H), 4.66-4.74 (m, 2H), 6.90 (d, 1H), 7.00 (d, 1H), 7.09 (d, 1H), 7.37 (s, 1H), 7.98 (s, 1H), 8.31 (d, 1H), 8.39 (m, 1H), 12.50 (s, 1H), 13.21 (s, 1H);

LCMS: Rt=2.61 min; m/z 596.4[M+H]+.

Example 38

[5-((S)-3-Dimethylamino-pyrrolidin-1-yl)-oyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 μmol) and (S)-3- dimethylaminopyrrolidine, (35 mg, 308 µmol) using the method of Example 32. The crude material was purified by HPLC Method C to afford (38 mg, 40%) of the title compound as off-white solid.

1H NMR (400 MHz, DMSO) δ (ppm): 1.03 (t, 3H), 1.75-1.83 (m, 2H), 2.21 (s, 6H), 2.79-2.81 (m, 3H), 3.18-3.23 (m, 2H), 3.43-3.45 (m, 2H), 3.69-3.77 (m, 1H), 3.79-3.81 (m, 1H), 3.90 (bs, 2H), 4.66 (m, 2H), 6.90 (d, 1H), 7.00 (d, 1H), 7.09 (d, 1H), 7.37 (s, 1H), 7.98 (s, 1H), 8.32 (m, 1H), 8.39 (m, 1H), 12.51 (s, 1H), 13.22 (s, 1H);

LCMS: Rt=2.61 min; m/z 596.4[M+H]+.

Example 39

{2-[6-(2-Ethyl-5-fluoro-4-hydroxy-phenyl)-1H-indazol-3-yl]-1,4,6,7-etrahydroimidazo[4,5c]pyridin-5-yl}-[5-(2-piperidin-1-yl-ethylamino)-pyrazin-2-yl]-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (120 mg, 231 µmol) and (2-(piperidine-1-yl) ethanamine, (59 mg, 463 µmol) using the method of Example 32. The crude material was purified by HPLC Method G to afford (38 mg, 27%) of the title compound as off-white solid.

1H NMR (400 MHz, DMSO) δ (ppm): 1.09 (t, 3H), 1.39 (Brs, 2H), 1.39-1.50 (m, 3H), 2.32 (m, 3H), 2.43-2.54 (m, 4H), 2.77 (Brs, 2H), 3.33-3.42 (m, 2H), 3.90 (Brs, 2H), 4.68 (m, 2H), 6.90-6.92 (d, 1H), 7.00-7.03 (d, 1H), 7.09 (m, 1H), 7.37 (s, 1H), 7.48 (s, 1H) 7.94 (s, 1H), 8.29-8.32 (s, 2H);

LCMS: Rt=2.64 min; m/z 610.2 [M+H]+.

Example 40

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-piperazin-1-yl-ethylamino)-pyrazin-2-yl]-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 µmol) and (2-(piperazinyl-1-yl) ethanamine, (40 mg, 309 µmol) using the method of Example 32. The crude material was purified by HPLC Method D to afford (26 mg, 28%) of the title compound as off-white solid.

1H NMR (400 MHz, DMSO) δ (ppm): 0.97-1.00 (t, 3H), 1.20 (s, 2H), 2.40-2.43 (m, 2H), 2.50 (s, 2H), 2.76 (Brs, 2H), 3.51-3.54 (d, 2H), 3.64 (Brs, 4H), 3.87-3.93 (d, 2H), 4.41-4.42 (m, 1H), 4.64-4.68 (d, 2H) 6.87-6.89 (d, 1H), 6.97-7.08 (m, 2H), 7.34 (s, 1H), 8.29 (s, 2H), 8.37 (s, 1H), 9.79 (s, 1H), 12.48 (s, 1H), 13.17 (s, 1H);

LCMS: Rt=2.59 min; m/z 612.4 [M+H]+.

Example 41

{2-[6-(2-Ethyl-5-fluoro-4-hydroxy-phenyl)-1H-indazol-3-yl]-1,4,6,7-tetrahydro-imidazo[4, 5-]pyridin-5-yl}-(4-methyl-3,4,5,6-tetrahydro-2H-[1,2']bipyrazinyl-5'-yl)-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 µmol) and 1-methyl-piperazine, (31 mg, 309 µmol) using the method of Example 32. The crude material was purified by HPLC Method D to afford (21 mg, 23%) of the title compound as off-white solid.

1H NMR (400 MHz, DMSO) δ (ppm): 0.90-1.03 (m, 6H), 2.22 (s, 3H), 2.40-2.49 (m, 4H), 2.78 (Brs, 2H), 3.67 (s, 3H), 3.88 (m, 2H), 4.66 (m, 2H), 6.90-6.92 (d, 1H), 7.00-7.03 (d, 2H), 7.37 (s, 1H) 8.32 (s, 3H), 9.82 (s, 1H), 12.50 (s, 1H), 13.20 (s, 1H);

LCMS: Rt=2.63 min; m/z 582.6 [M+H]+.

Example 42

{2-[6-(2-Ethyl-5-fluoro-4-hydroxy-phenyl)-1H-indazol-3-yl]-1,4,6,7-tetrahydro-imidazo[4,5-c]hyridin-5-yl}-(5-morpholin-4-yl-pyrazin-2-yl)-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (100 mg, 154 µmol) and morpholine, (34 mg, 386 µmol) using the method of Example 32. The crude material was purified by HPLC Method F to afford (42 mg, 38%) of the title compound as off-white solid.

1H NMR (400 MHz, DMSO) δ (ppm): 0.99-1.03 (t, 3H), 2.78 (Brs, 2H), 3.65-3.72 (q, 8H), 3.88 (d, 2H), 4.67-4.77 (m, 2H), 6.90 (d, 1H), 2H) 7.00-7.11 (m, 2H), 7.37 (s, 1H), 8.26 (s, 2H), 8.42 (s, 1H), 12.50 (s, 1H), 13.20 (s, 1H);

LCMS: Rt=3.23 min; m/z 569.4 [M+H]+.

Example 43

{2-[6-(2-Ethyl-5-fluoro-4-hydroxy-phenyl)-1H-indazol-3-yl]-1,4,6,7-tetrahydro-idazo[4,5c]pyridin-5-yl}-[5-(4-methyl-piperidin-1-yl)-pyrazin-2-yl]-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (100 mg, 154 µmol) and 4-methyl-piperidine, (38 mg, 386 µmol) using the method of Example 32. The crude material was purified by HPLC Method F to afford (34 mg, 30%) of the title compound as off-white solid.

1H NMR (400 MHz, DMSO) δ (ppm): 0.92-0.93 (d, 3H), 0.99-1.03 (t, 3H), 1.10-1.16 (m, 2H), 1.69-1.75 (m, 3H), 1.85 (s, 1H), 2.78 (Brs, 2H), 2.91-2.98 (t, 2H), 3.93 (Brs, 2H), 4.42-4.45 (d, 2H), 4.66-4.75 (m, 2H) 6.90-6.92 (d, 1H), 7.00-7.03 (d, 2H), 7.37 (s, 1H), 8.31-8.39 (m, 3H), 12.51 (s, 1H), 13.21 (s, 1H);

LCMS: Rt=3.11 min; m/z 581.4 [M+H]+.

Example 44

(5-Cyclopentylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (90 mg, 173 µmol) and cylopenylamine, (30 mg, 347 µmol) using the method of Example 32. The crude material was purified by HPLC Method G to afford (28 mg, 28%) of the title compound as off-white solid.

1H NMR (400 MHz, DMSO) δ (ppm): 1.03 (t, 3H), 1.45-1.51 (m, 2H), 1.56-1.57 (m, 2H), 1.69 (m, 2H), 1.93-1.95 (m, 2H), 2.53 (m, 1H), 2.78 (Brs, 2H), 3.16 (s, 1H), 3.91 (Brs, 2H), 4.14-4.19 (m 1H), 4.64 (m, 2H), 6.90-6.92 (d, 1H), 7.00-7.03 (d, 1H), 7.09 (d, 1H), 7.37 (s, 1H), 7.62 (s, 1H) 7.88 (s, 1H), 8.29 (s, 2H);
LCMS: Rt=2.98 min; m/z 567.6 [M+H]+.

Example 45

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-morpholin-4-yl-ethylamino)-pyrazin-2-yl]-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (100 mg, 193 µmol) and 2-morpholin-4-yl-ethylamine, (30 mg, 347 µmol) using the method of Example 32. The crude material was purified by HPLC Method F to afford (28 mg, 28%) of the title compound as off-white solid.
1H NMR (400 MHz, DMSO) δ (ppm): 0.99-1.03 (t, 3H), 2.49-2.57 (m, 2H), 2.77 (Brs, 2H), 3.16 (s, 2H), 3.32 (s, 3H), 3.56-3.58 (m, 2H), 2H) 3.90 (m, 2H) 4.69 (m, 2H) 6.90-6.92 (d, 1H), 7.00-7.03 (d, 1H), 7.09 (m, 1H), 7.37 (s, 1H), 7.53 (Brs, 1H), 7.95 (s, 1H), 8.29 (s, 2H);
LCMS: Rt=5.89 min; m/z 612.4 [M+H]+.

Example 46

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-isopropyl-3,4,5,6-tetrahydro-2H-[1,2']bipyrazinyl-5'-yl)-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 µmol) and 1-isopropyl-piperazine, (40 mg, 308 µmol) using the method of Example 32. The crude material was purified by HPLC Method D to afford (18 mg, 19%) of the title compound as off-white solid.
1H NMR (400 MHz, DMSO) δ (ppm): 0.95-1.03 (m, 9H), 2.53 (m, 4H), 2.68-2.78 (m, 3H), 3.65 (s, 4H), 3.89-3.95 (m, 2H), 4.70 (m, 2H), 6.90 (d, 1H), 7.00 (d, 1H), 7.09 (d, 1H), 7.37 (s, 1H), 8.31 (m, 2H), 8.39 (d, 1H), 9.82 (bs, 1H), 12.51 (s, 1H), 13.20 (s, 1H);
LCMS: Rt=6.52 min; m/z 610.4[M+H]+.

Example 47

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-pyrrolidin-1-yl-pyrazin-2-yl)-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 µmol) and pyrrolidine (22 mg, 308 µmol) using the method of Example 32. The crude material was purified by HPLC Method D to afford (18 mg, 19%) of the title compound as off-white solid.
1H NMR (400 MHz, DMSO) δ (ppm): 1.01 (t, 3H), 1.97 (bs, 4H), 2.78 (bs, 2H), 3.50 (s, 4H), 3.93 (bs, 2H), 4.65-4.76 (m, 2H), 6.90 (d, 1H), 7.00 (d, 1H), 7.08 (d, 1H), 7.36 (s, 1H), 7.96 (s, 1H), 8.31 (d, 1H), 8.39 (s, 1H), 9.86 (bs, 1H), 12.52 (s, 1H), 13.22 (s, 1H); LCMS: Rt=2.85 min; m/z 553.4[M+H]+.
LCMS: Rt=2.85 min; m/z 553.4[M+H]+.

Example 48

{2-[6-(2-Ethyl-5-fluoro-4-hydroxy-phenyl)-1H-indazol-3-yl]-1,4,6,7-tetrahydro-imidazo[4,5-]pyridin-5-yl}-[5-(ethyl-methyl-amino)-pyrazin-2-yl]-methanon The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 µmol) and ethyl-methylamine (18 mg, 308 µmol) using the method of Example 32. The crude material was purified by HPLC Method E to afford (38 mg, 46%) of the title compound as off-white solid.
1H NMR (400 MHz, DMSO) δ (ppm): 1.01 (t, 3H), 1.12 (t, 3H), 2.78 (m, 2H), 3.11 (s, 3H), 3.65 (m, 2H), 3.93 (m, 2H), 4.76 (m, 2H), 6.90 (d, 1H), 7.00 (d, 1H), 7.09 (d, 1H), 7.37 (s, 1H), 8.13 (s, 1H), 8.31 (m, 1H), 8.39 (s, 1H), 9.84 (bs, 1H), 12.51 (s, 1H), 13.22 (s, 1H);
LCMS: Rt=2.85 min; m/z 541.6[M+H]+.

Example 49

(5-Cyclohexylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (126 mg, 243 µmol) and cyclohexylamine (48 mg, 487 µmol) using the method of Example 32. The crude material was purified by HPLC Method D to afford (29 mg, 20%) of the title compound as off-white solid.
1H NMR (400 MHz, DMSO) δ (ppm): 0.99-1.04 (m, 3H), 1.18-1.35 (m, 6H), 1.62-1.84 (m, 6H), 1.90-1.93 (m, 1H), 2.78 (m, 2H), 3.32 (m, 1H), 3.76-3.91 (m, 2H), 4.66-4.72 (m, 2H), 6.90 (d, 1H), 7.00 (d, 1H), 7.09 (d, 1H), 7.37 (s, 1H), 7.51 (bs, 1H), 7.88 (s, 1H), 8.23 (s, 1H), 12.50 (bs, 1H), 13.22 (bs, 1H);
LCMS: Rt=3.06 min; m/z 581.6[M+H]+.

Example 50

(5-Dimethylamino-pyrazin-2-yl)-{2-[6-(2-ethyl-5-fluoro-4-hydroxy-phenyl)-1H-indazol-3-yl]-,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl) methanone (80 mg, 154 µmol) and dimethylamine HCl (25 mg, 308 µmol) using the method of Example 32. The crude material was purified by HPLC Method D to afford (17 mg, 21%) of the title compound as off-white solid.
1H NMR (400 MHz, DMSO) δ (ppm): 1.01 (t, 3H), 2.79 (m, 2H), 3.15 (s, 6H), 3.93 (m, 2H), 4.70 (m, 2H), 6.90 (d, 1H), 7.00 (d, 1H), 7.01 (d, 1H), 7.09 (d, 1H), 7.37 (s, 1H), 8.15 (s, 1H), 8.31 (m, 1H), 8.40 (s, 1H), 9.84 (bs, 1H), 12.51 (s, 1H), 13.20 (s, 1H);
LCMS: Rt=2.81 min; m/z 527.4[M+H]+.

Example 51

(5-Azetidin-1-yl-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone (80 mg, 154 μmol) and azetdine HCl (29 mg, 308 μmol) using the method of Example 32. The crude material was purified by HPLC Method D to afford (19 mg, 23%) of the title compound as off-white solid.

1H NMR (400 MHz, DMSO) δ (ppm): 1.03 (t, 3H), 2.43-2.49 (m, 2H), 2.78 (bs, 2H), 3.37 (m, 2H), 3.87-3.95 (m, 2H), 4.13 (t, 4H), 4.65-4.70 (m, 2H), 6.90 (d, 1H), 7.00 (d, 1H), 7.09 (d, 1H), 7.37 (s, 1H), 7.83 (s, 1H), 8.33-8.37 (m, 2H), 9.84 (bs, 1H), 12.52 (s, 1H), 13.21 (s, 1H);
LCMS: Rt=2.78 min; m/z 539.4[M+H]+.

Example 52

2-Fluoro-4-{3-[5-(4-fluoro-benzyl)-4,5,6,7-tetrahydro-1H-imidazo[4,5-c]pyridin-2-yl]-1H-indazol-6-yl}-5-(2,2,2-trifluoro-ethyl)-phenol To a solution of 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (Preparation 39, 100 mg, 0.21 mmol) and KOAc (22.75 mg, 0.23 mmol) in MeOH (1 mL), 4-fluorobenzaldehyde (57.54 mg, 0.46 mmol) was added and the mixture stirred at room temperature for 1 hr followed by portionwise addition of sodium triacetoxy borohydride (162.12 mg, 0.76 mmol) over 2 hrs. The mixture was thereafter stirred at room temperature for 18 hrs. The reaction mixture was concentrated and the residue partitioned between saturated sodium bicarbonate solution & ethyl acetate. The organic phase was dried over sodium sulphate, evaporated in vacuo, purified initially over silica and finally by Prep TLC (Mobile Phase: 10% MeOH-DCM) to afford the title compound as a light yellow solid in 30.35% yield, 35 mg.

1H NMR (400 MHz, DMSO) δ (ppm): 2.66 (m, 2H), 2.76-2.80 (m, 2H), 3.44-3.56 (m, 4H), 3.71 (s, 2H), 7.07-7.10 (m, 2H), 7.13-7.19 (m, 2H), 7.36 (s, 1H), 7.41-7.43 (m, 2H), 8.29-8.36 (m, 1H), 10.13 (s, 1H), 12.21-12.34 (m, 1H), 13.19 (s, 1H);
LCMS: Rt=3.17 min; m/z 540.4 [M+H]+

Example 53

2-Fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and 3,4,5,6-tetrahydro-2H-[1,2']bipyridinyl-5'-carbaldehyde (88.2 mg, 0.46 mmol) using the method of Example 51. The crude material was purified initially over silica and finally by Prep TLC (Mobile Phase: 10% MeOH-DCM) to afford the title compound as an off white solid in 16.99% yield, 22 mg.

1H NMR (400 MHz, DMSO) δ (ppm): 1.53 (m, 6H), 2.64 (m, 2H), 2.73-2.77 (m, 2H), 3.41-3.57 (m, 10H), 6.78 (d, 1H), 7.02-7.10 (m, 2H), 7.14-7.17 (m, 1H), 7.36 (s, 1H), 7.48 (d, 1H), 8.03 (s, 1H), 8.30-8.35 (m, 1H), 10.15 (s, 1H), 12.22-12.34 (m, 1H), 13.20 (s, 1H);
LCMS: Rt=3.17 min; m/z 606.2 [M+H]+

Example 54

2-Fluoro-4-{3-[5-(6-ohenoxy-pyridin-3-ylmethyl)-4,5,6,7-tetrahydro-1H-imidazo[4,5-c]pyridin-2-yl]-H-indazol-6-yl}-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and 6-phenoxy-pyridine-3-carbaldehyde (92.3 mg, 0.46 mmol) using the method of Example 51. The crude material was purified initially over silica and finally by Prep TLC (Mobile Phase: 10% MeOH-DCM) to afford the title compound as an off white solid in 23.6% yield, 31 mg.

1H NMR (400 MHz, DMSO) δ (ppm): 2.67 (m, 2H), 2.77 (m, 2H), 3.45-3.56 (m, 4H), 3.70 (s, 2H), 6.78 (d, 1H), 7.00-7.22 (m, 6H), 7.36 (s, 1H), 7.39-7.43 (t, 2H), 7.84 (d, 1H), 8.11 (s, 1H), 8.30-8.35 (m, 1H), 10.15 (s, 1H), 12.24-12.36 (m, 1H), 13.21 (s, 1H);
LCMS: Rt=3.20 min; m/z 615.4 [M+H]+

Example 55

2-Fluoro-4-{3-[5-(4-methoxy-benzyl)-4,5,6,7-tetrahydro-1H-imidazo[4,5-d]pyridin-2-yl]-1H indazol-6-yl}-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and 4-methoxybenzaldehyde (63.1 mg, 0.46 mmol) using the method of Example 51. The crude material was purified initially over silica and finally by Prep TLC (Mobile Phase: 10% MeOH-DCM) to afford the title compound as an off white solid in 22.1% yield, 26 mg.

1H NMR (400 MHz, DMSO) δ (ppm): 2.65 (m, 2H), 2.73-2.79 (m, 2H), 3.37-3.47 (m, 2H), 3.50-3.56 (m, 2H), 3.64 (s, 2H), 3.75 (s, 3H), 6.90-6.92 (m, 2H), 7.02-7.10 (m, 2H), 7.13-7.16 (m, 1H), 7.27-7.29 (m, 2H), 7.36 (s, 1H), 8.29-8.36 (m, 1H), 10.13 (s, 1H), 12.20-12.35 (m, 1H), 13.19 (s, 1H);
LCMS: Rt=3.15 min; m/z 552.2 [M+H]+

Example 56

2-Fluoro-4-{3-[5-(4-hydroxy-benzyl)-4,5,6,7-tetrahydro-1H-imidazo[4,5-d]pyridin-2-yl]-1H-indazol-6-yl}-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and 4-hydroxybenzaldehyde (56.6 mg, 0.46 mmol) using the method of Example 51. The crude material was purified initially over silica and finally by Prep TLC (Mobile Phase: 10% MeOH-DCM) to afford the title compound as an off white solid in 24.4% yield, 28 mg.

1H NMR (400 MHz, DMSO) δ (ppm): 2.66 (m, 2H), 2.73-2.78 (m, 2H), 3.40-3.43 (m, 2H), 3.47-3.56 (m, 2H), 3.59 (s, 2H), 6.72-6.74 (d, 2H), 7.02-7.10 (m, 2H), 7.14-7.18 (m, 3H), 7.36 (s, 1H), 8.29-8.36 (m, 1H), 9.27 (s, 1H), 10.13 (s, 1H), 12.20-12.32 (m, 1H), 13.19 (s, 1H);
LCMS: Rt=2.86 min; m/z 538.2 [M+H]+

Example 57

2-Fluoro-4-{3-[5-(3-methoxy-benzyl)-4,5,6,7-tetrahydro-1H-imidazo[4,5-d]pyridin-2-yl]-1H-indazol-6-yl}-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and 3-methoxybenzaldehyde (63.1 mg, 0.46 mmol) using the method of Example 51. The crude material was purified initially over silica and finally by Prep TLC (Mobile Phase: 10% MeOH-DCM) to afford the title compound as an off white solid in 21.2% yield, 25 mg.

1H NMR (400 MHz, DMSO) δ (ppm): 2.66 (m, 2H), 2.76-2.80 (m, 2H), 3.45-3.56 (m, 4H), 3.69 (s, 2H), 3.75 (s, 3H), 6.83-6.85 (d, 1H), 6.94 (m, 2H), 7.02-7.10 (m, 2H), 7.14 (d, 1H), 7.24-7.28 (t, 1H), 7.36 (s, 1H), 8.29-8.36 (m, 1H), 10.15 (s, 1H), 12.23-12.35 (m, 1H), 13.20 (s, 1H);

LCMS: Rt=3.14 min; m/z 552 [M+H]+

Example 58

2-Fluoro-4-{3-[5-(3-hydroxy-benzyl)-4,5,6,7-tetrahydro-1H-imidazo[4,5-d]pyridin-2-yl]-1H-indazol-6-yl}-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and 3-hydroxybenzaldehyde (56.6 mg, 0.46 mmol) using the method of Example 51. The crude material was purified initially over silica and finally by Prep TLC (Mobile Phase: 10% MeOH-DCM) to afford the title compound as an off white solid in 26.1% yield, 30 mg.

1H NMR (400 MHz, DMSO) δ (ppm): 2.66 (m, 2H), 2.76-2.81 (m, 2H), 3.43-3.53 (m, 4H), 3.63 (s, 2H), 6.64-6.66 (d, 1H), 6.76-6.81 (m, 2H), 7.02-7.16 (m, 4H), 7.36 (s, 1H), 8.30-8.32 (m, 1H), 9.28 (d, 1H), 10.13 (s, 1H), 12.21-12.33 (m, 1H), 13.19 (s, 1H);

LCMS: Rt=2.90 min; m/z 538.2 [M+H]+

Example 59

2-Fluoro-4-[3-(5-quinolin-6-ylmethyl-4,5,6,7-tetrahydro-1H-imidazo[4,5-d]pyridin-2-yl)-1H-indazol-6-yl]-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and quinoline-6-carbaldehyde (72.9 mg, 0.46 mmol) using the method of Example 51. The crude material was purified initially over silica and finally by Prep TLC (Mobile Phase: 10% MeOH-DCM) to afford the title compound as an off white solid in 22.9% yield, 28 mg.

1H NMR (400 MHz, DMSO) δ (ppm): 2.67 (m, 2H), 2.83. 2.89 (m, 2H), 3.49-3.55 (m, 4H), 3.93 (s, 2H), 7.01-7.17 (m, 3H), 7.36 (s, 1H), 7.51 (m, 1H), 7.80 (d, 1H), 7.95 (s, 1H), 7.99 (d, 1H), 8.29-8.38 (m, 2H), 8.87 (d, 1H), 10.13 (s, 1H), 12.21-12.33 (m, 1H), 13.19 (s, 1H);

LCMS: Rt=2.90 min; m/z 573.6 [M+H]+

Example 60

2-Fluoro-4-[3-(5-quinolin-3-ylmethyl-4,5,6,7-tetrahydro-1H-imidazo[4,5-d]pyridin-2-yl)-1H-indazol-6-yl]-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and quinoline-3-carbaldehyde (72.9 mg, 0.46 mmol) using the method of Example 51. The crude material was purified initially over silica and finally by Prep TLC (Mobile Phase: 10% MeOH-DCM) to afford the title compound as an off white solid in 27.8% yield, 34 mg.

1H NMR (400 MHz, DMSO) δ (ppm): 2.67-2.70 (m, 2H), 2.83. 2.90 (m, 2H), 3.47-3.58 (m, 4H), 3.95 (s, 2H), 7.01-7.17 (m, 3H), 7.36 (s, 1H), 7.59 (t, 1H), 7.74 (t, 1H), 8.02 (t, 2H), 8.29-8.38 (m, 2H), 8.93 (d, 1H), 10.14 (s, 1H), 12.23-12.36 (m, 1H), 13.20 (s, 1H);

LCMS: Rt=2.97 min; m/z 573.6 [M+H]+

Example 61

2-Fluoro-4-[3-(5-[1,8]naphthyridin-3-ylmethyl-4,5,6,7-tetrahydro-1H-imidazo[4,5-c]pyridin-2-yl)-1H-indazol-6-yl]-5-(2,2,2-trifluoro-ethyl)-phenol The title compound was prepared from 2-fluoro-4-[3-(4,5,6,7-tetrahydro-1H-imidazo[4,5-c]pyridin-2-yl)-1H-indazol-6-yl]-5-(2,2,2-trifluoro-ethyl)-phenol (100 mg, 0.21 mmol) and [1,8]naphthyridine-3-carbaldehyde (146.1 mg, 0.92 mmol) using the method of Example 51. The crude material was purified initially over silica and finally by Prep TLC (Mobile Phase: 10% MeOH-DCM) to afford the title compound as an off white solid in 9.0% yield, 22 mg.

1H NMR (400 MHz, DMSO) δ (ppm): 2.72 (m, 2H), 2.89. 2.92 (m, 2H), 3.50-3.54 (m, 2H), 3.60-3.63 (m, 2H), 4.08 (s, 2H), 7.02-7.17 (m, 3H), 7.36 (s, 1H), 7.61-7.64 (m, 1H), 7.82-7.85 (m, 1H), 8.29-8.38 (m, 2H), 8.44-8.47 (m, 2H), 9.06 (m, 1H), 10.15 (s, 1H), 12.26-12.39 (m, 1H), 13.21 (s, 1H);

LCMS: Rt=2.86 min; m/z 574.2 [M+H]+

Example 62

((3R,5S)-3,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone To a stirring solution of (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone (150 mg, 0.154 mmol) in DMSO (1.5 mL) were added DIPEA (0.143 mL, 0.87 mmol) and (2R,6S)-2,6-Dimethyl-piperazine-1-carboxylic acid tert-butyl ester (124 mg, 0.58 mmol) and the mixture stirred at room temperature for 18 hours. The crude reaction mass was purified by prep-HPLC Method F to afford (3R,5S)-5'-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-3,5-dimethyl-2,3,5,6-tetrahydro-[1,2']bipyrazinyl-4-carboxylic acid tert-butyl ester as an off white solid (80 mg, 40%).

LCMS: Rt=3.18 min; m/z 696.6 [M+H]+.

To a stirring solution of (3R,5S)-5'-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-3,5-dimethyl-2,3,5,6-tetrahydro-[1,2']bipyrazinyl-4-carboxylic acid tert-butyl ester (80 mg, 0.114 mmol) in dioxane (3 mL), 10% dioxane-HCl (2 mL) was added and the mixture stirred at RT for 18 hours. The reaction mass was evaporated in vacuo and the resulting solid triturated with ether to afford the title compound (HCl salt) as an off white solid (62 mg 91%).

1H NMR (400 MHz, DMSO): 1.06 (t, 3H), 1.22-1.34 (s, 6H), 2.94 (Brs, 2H), 3.01-3.07 (t, 2H), 3.32 (Brs, 2H), 3.97 (m, 2H), 4.61-4.64 (d, 2H), 4.84 (s, 2H), 6.94 (d, 1H), 7.03 (d, 1H), 7.32 (s, 1H), 7.58 (s, 1H), 8.41-8.48 (m, 3H), 9.27 (m, 1H), 9.64 (m, 1H), 9.79 (s, 1H), 14.33 (s, 1H);

LCMS: Rt=2.65 min; m/z 596.4 [M+H]+.

Example 63

{2-[6-(2-Ethyl-5-fluoro-4-hydroxy-phenyl)-1H-indazol-3-yl]-1,4,6,7-tetrahydro-imidazo[4,5-c]pyridin-5-yl}-((S)-3-methyl-3,4,5,6-tetrahydro-2H-[1,2']bipyrazinyl-5'-yl)-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone (200 mg, 386 µmol) and (S)-2-methyl-piperazine-1-carboxylic acid tert-butyl ester (155 mg, 773 µmol) using the method from Example 61. After purification by HPLC Method E and deprotection using HCl/dioxan, the title compound (58 mg, 25% yield over two steps) was obtained as off-white solid (HCl-salt).

1H NMR (400 MHz, DMSO): 0.82 (t, 3H), 1.23-1.31 (s, 3H), 2.93 (Brs, 2H), 3.07-3.18 (m, 3H), 3.97 (Brs, 2H), 4.50-4.53 (d, 2H), 4.83 (s, 2H), 6.93-6.95 (d, 1H), 7.03-7.06 (d, 1H), 7.28-7.30 (m, 1H), 7.57 (s, 1H), 8.37 (m, 1H), 8.44 (s, 1H), 8.49 (s, 1H), 9.24 (s, 1H), 9.40 (m, 1H), 9.94 (s, 1H), 14.25 (s, 1H);

LCMS: Rt=2.61 min; m/z 582.4 [M+H]+.

Example 64

((2S,5R)-2,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone (100 mg, 193 µmol) and (2S,5R)-2,5-Dimethyl-piperazine-1-carboxylic acid tert-butyl ester (84 mg, 386 µmol) using the method from Example 61. After purification by HPLC Method E and deprotection using HCl/dioxan, the title compound (43 mg, 37% yield over two steps) was obtained as off-white solid (HCl-salt).

1H NMR (400 MHz, DMSO): 0.82 (t, 3H), 1.33-1.34 (m, 6H), 2.95 (Brs, 3H), 3.11-3.14 (d, 1H), 3.37 (s, 1H), 3.51-3.62 (m, 5H), 3.83 (Brs, 2H), 4.01 (m, 1H), 4.84 (m, 3H), 6.94-6.96 (d, 1H), 7.03-7.06 (d, 1H), 7.31 (Brs, 1H), 7.58 (s, 1H), 8.36 (s, 2H), 8.49 (s, 1H), 9.33 (m, 1H), 9.53 (s, 1H), 14.33 (s, 1H);

LCMS: Rt=2.55 min; m/z 596.2 [M+H]+.

Example 65

{2-[6-(2-Ethyl-5-fluoro-4-hydroxy-phenyl)-1H-indazol-3-yl]-1,4,6,7-tetrahydro-imidazo[4, 5-]pyridin-5-yl}-(3,4,5,6-tetrahydro-2H-[1,2']bipyrazinyl-5'-yl)-methanone The title compound was prepared from (5-chloropyrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone (200 mg, 386 µmol) and piperazine-1-carboxylic acid tert-butyl ester (144 mg, 773 µmol) using the method from Example 61. After purification by HPLC Method E and deprotection using HCl/dioxan, the title compound (64 mg, 29% yield over two steps) was obtained as off-white solid (HCl-salt).

1H NMR (400 MHz, DMSO): 1.00-1.03 (t, 3H), 2.94 (Brs, 2H), 3.22 (s, 4H), 3.93-3.95 (m, 6H), 4.84 (s, 2H), 6.94-6.96 (d, 1H), 7.03-7.06 (d, 1H), 7.30-7.33 (m, 1H), 7.58 (s, 1H), 8.42 (s, 2H), 8.50 (s, 1H), 9.29 (Brs, 2H), 9.95 (s, 1H), 14.30 (s, 1H);

LCMS: Rt=2.48 min; m/z 568.2 [M+H]+.

Preparation 1

6-Bromo-1-(tetrahydro-pyran-2-yl)-1H-indazole-3-carbaldehyde

To a solution of 6-bromo-1H-indazole-3-carbaldehyde (13.97 g, 61.9 mmol) in DCM (150 mL) was added p-TsOH (2.36 g, 12.4 mmol) and the mixture was cooled to 0° C. 3,4-Dihydro-2H-pyran (8.47 mL, 92.8 mmol) was added dropwise to the solution and the reaction was stirred at room temperature overnight. The reaction mixture was diluted with DCM (200 mL) and washed with a solution of saturated aqueous sodium hydrogen carbonate (500 mL). The aqueous layer was re-extracted with DCM (500 mL) and the combined organic layers were washed with brine (2×1 L), dried over $MgSO_4$ and concentrated in vacuo to yield a black oil. The crude material was refluxed in cyclohexane (20 mL) and filtered while hot. The filtrate was concentrated in vacuo and the residue was stirred in heptane for 48 hours. The resulting solid was collected by filtration to give the title compound (13.87 g) in a 73% yield.

$^1$H NMR (400 MHz, $CDCl_3$) δ ppm 1.71-1.80 (m, 3H), 2.10-2.20 (m, 2H), 2.49-2.57 (m, 1H), 3.76-3.82 (m, 1H), 3.98-4.03 (m, 1H), 5.78 (dd, 1H), 7.46 (dd, 1H), 7.87 (d, 1H), 8.16 (d, 1H), 10.22 (s, 1H).

Preparation 2

6-Bromo-1-(tetrahydro-pyran-2-yl)-1H-indazole-3-carbonitrile

To a solution of 6-bromo-1-(tetrahydro-pyran-2-yl)-1H-indazole-3-carbaldehyde (Preparation 1, 60 g, 194 mmol) in MeCN (1.5 L) was added triethylamine (68.5 mL, 485 mmol) and hydroxylamine hydrochloride (20 g, 291 mmol). The reaction was heated at 60° C. for 3 hours. The reaction was cooled to 0° C., further triethylamine (220 mL, 1.55 mol) was added and TFAA (109 mL, 776 mmol) was added dropwise. The reaction was allowed to warm to room temperature and stirred for 2 hours. Water (2 L) was added to the reaction mixture and the resulting solid was collected by filtration. The solid was dissolved in DCM (1 L) and the resulting solution was washed with water (2×500 mL). The organic layer was dried over MgSO₄ and concentrated in vacuo to give the title compound as a white solid (58.59 g) in a 99% yield.

¹H NMR (400 MHz, CDCl₃) δ ppm 1.71-1.80 (m, 3H), 2.08-2.18 (m, 2H), 2.43-2.50 (m, 1H), 3.73-3.79 (m, 1H), 3.92-3.96 (m, 1H), 5.77 (dd, 1H), 7.47 (dd, 1H), 7.69 (d, 1H), 7.93 (d, 1H).

Preparation 3

4-Bromo-5-ethyl-2-fluoro-phenol

To a solution of 5-ethyl-2-fluoro-phenol (WO 2007/002313, 76.36 g, 545 mmol) in MeCN (2.5 L) was added copper (II) bromide (361.5 g, 1.619 mol). The resulting suspension was stirred at room temperature overnight. The solvent was removed in vacuo and the residue was suspended in EtOAc (3 L) and filtered through a pad of Arbocel®. The filtrate was washed with water (2 L) and brine (2 L), dried over MgSO₄ and concentrated in vacuo to furnish the title compound (119 g) in 100% yield.

¹H NMR (400 MHz, CDCl₃) δ ppm 1.19 (t, 3H), 2.86 (q, 2H), 5.20 (s, 1H), 6.90 (d, 1H), 7.25 (d, 1H).

Preparation 4

[2-(4-Bromo-5-ethyl-2-fluoro-phenoxymethoxy)-ethyl]-trimethyl-silane

To a solution of 4-bromo-5-ethyl-2-fluoro-phenol (Preparation 3, 80 g, 365 mmol) in DCM (1 L) was added DIPEA (70 mL, 401 mmol) and SEM-Cl (71 mL, 401 mmol). The resulting solution was stirred at room temperature for 18 hours. The reaction mixture was washed with water (1 L), dried over MgSO₄ and concentrated in vacuo to yield the crude product. This material was purified by silica gel chromatography eluting with 30% DCM in heptane to give the title compound as a pale yellow oil (109.8 g, 86%).

¹H NMR (400 MHz, CDCl₃) δ ppm 0.00 (s, 9H), 0.92-0.97 (m, 2H), 1.19 (t, 3H), 2.67 (q, 2H), 3.77-3.81 (m, 2H), 5.22 (s, 2H), 7.08 (d, 1H), 7.25 (d, 1H).

Preparation 5

2-[2-Ethyl-5-fluoro-4-(2-trimethylsilanyl-ethoxymethoxy)-phenyl]-4,4,5,5-tetramethyl-[1,3,2]dioxaborolane To a solution of [2-(4-bromo-5-ethyl-2-fluoro-phenoxymethoxy)-ethyl]-trimethyl-silane (Preparation 4, 105 g, 300.6 mmol) in dioxane (1 L) was added bis(pinacolato)diboron (76.4 g, 300.6 mmol) and KOAc (88.5 g, 902 mmol). The resulting suspension was degassed with nitrogen, Pd(dppf)Cl₂ (24.54 g, 30.1 mmol) was added and the reaction was heated at reflux for 18 hours. The reaction was cooled to room temperature and the solvent was removed in vacuo. The resulting black solid was suspended in EtOAc (2 L) and filtered through Arbocel®, washing with further EtOAc. The filtrate was washed with water (1.5 L) and brine (1.5 L), dried over MgSO₄ and concentrated in vacuo to yield the title compound as a black oil (155.6 g, 130%) that was used crude in the next step.

¹H NMR (400 MHz, CDCl₃) δ ppm 0.00 (s, 9H), 0.93-0.97 (m, 2H), 1.17 (t, 3H), 1.32 (s, 12H), 2.86 (q, 2H), 3.73-3.82 (m, 2H), 5.25 (s, 2H), 7.01 (d, 1H), 7.47 (d, 1H).

Preparation 6

6-[2-Ethyl-5-fluoro-4-(2-trimethylsilanyl-ethoxymethoxy)-phenyl]-1-(tetrahydro-pyran-2-yl)-1H-indazole-3-carbonitrile To a solution of 6-bromo-1-(tetrahydro-pyran-2-yl)-1H-indazole-3-carbonitrile (Preparation 2, 28.5 g, 93 mmol) and 2-[2-ethyl-5-fluoro-4-(2-trimethylsilanyl-ethoxymethoxy)-phenyl]-4,4,5,5-tetramethyl-[1,3,2]dioxaborolane (Preparation 5, 73.8 g, 112 mmol) in dioxane (500 mL) was added a solution of potassium phosphate (59.2 g, 279 mmol) in water (120 mL). The mixture was degassed with nitrogen and then tetrakis (triphenylphosphine) palladium(0) (10.8 g, 9.3 mmol) was added. The reaction mixture was heated at 110° C. for 18 hours. The reaction mixture was concentrated in vacuo and the residue was redissolved in EtOAc (1 L) and filtered through Arbocel®, washing with EtOAc (2×500 mL). The combined organic phases were concentrated in vacuo to give a brown oil. The residue was purified by column chromatography on silica gel eluting with 10% EtOAc in heptane to give the title compound as a viscous oil (37.4 g) in an 81% yield.

¹H NMR (400 MHz, CDCl₃) δ ppm 0.00 (s, 9H), 0.97 (t, 2H), 1.06 (t, 3H), 1.66-1.77 (m, 3H), 2.05-2.17 (m, 2H), 2.44-2.48 (m, 3H), 3.67-3.73 (m, 1H), 3.82 (t, 2H), 3.90-3.94 (m, 1H), 5.28 (s, 2H), 5.77 (dd, 1H), 6.95 (d, 1H), 7.13 (d, 1H), 7.25 (d, 1H), 7.58 (s, 1H), 7.80 (d, 1H).

Preparation 7

6-[2-Ethyl-5-fluoro-4-(2-trimethylsilanyl-ethoxymethoxy)-phenyl]-1-(tetrahydro-pyran-2-yl)-1H-indazole-3-carboximidic acid methyl ester To a solution of 6-[2-ethyl-5-fluoro-4-(2-trimethylsilanyl-ethoxymethoxy)-phenyl]-1-(tetrahydro-pyran-2-yl)-1H-indazole-3-carbonitrile (Preparation 6, 37.42 g, 75.6 mmol) in methanol (700 mL) was added sodium methoxide (12.21 g, 226.8 mmol) and the reaction mixture was then stirred at room temperature for 18 hours. The solvent was removed in vacuo and the residue was partitioned between EtOAc (1 L) and water (500 mL). The organic layer was washed with water (500 mL), dried over MgSO₄ and concentrated in vacuo to give the title compound as a gum (37.26 g) in a 94% yield.

¹H NMR (400 MHz, CDCl₃) δ ppm 0.00 (s, 9H), 0.97 (t, 2H), 1.06 (t, 3H), 1.61-1.76 (m, 3H), 2.03-2.15 (m, 2H), 2.47-2.56 (m, 3H), 3.67-3.72 (m, 1H), 3.82 (t, 2H), 3.97-4.01 (m, 1H), 4.03 (s, 3H), 5.28 (s, 2H), 5.71 (dd, 1H), 6.97 (d, 1H), 7.12 (d, 1H), 7.15 (d, 1H), 7.46 (s, 1H), 8.03 (d, 1H), 8.45 (s, 1H).

LCMS: m/z 528 M+H⁺.

Preparation 8

N-(1-Benzyl-4,4-diethoxy-piperidin-3-yl)-6-[2-ethyl-5-fluoro-4-(2-trimethylsilanyl-ethoxymethoxy)-phenyl]-1-(tetrahydro-pyran-2-yl)-1H-indazole-3-carboxamidine To a solution of 6-[2-ethyl-5-fluoro-4-(2-trimethylsilanyl-ethoxymethoxy)-phenyl]-1-(tetrahydro-pyran-2-yl)-1H-indazole-3-carboximidic acid methyl ester (Preparation 7, 17.15 g, 32.49 mmol) in ethanol (100 mL) was added a solution of 1-benzyl-4,4-diethoxy-piperidin-3-ylamine (Tetrahedron, 1995, 51, 13447-13454; 9.51 g, 34.2 mmol) in ethanol (70 mL). Acetic acid (3.56 mL, 62.1 mmol) was added and the reaction mixture was heated at 50° C. for 18 hours. The reaction mixture was concentrated in vacuo and the residue was partitioned between EtOAc (400 mL) and saturated sodium hydrogen carbonate aqueous solution (300 mL). The organic layer was washed with further saturated sodium hydrogen carbonate aqueous solution (300 mL). The combined aqueous layers were re-extracted with EtOAc (400 mL). The combined organic layers were dried over MgSO$_4$ and concentrated in vacuo. The crude product was purified by column chromatography on silica gel eluting with DCM:methanol:ammonia (80:20:2) to give the title compound (11.31 g) in a 45% yield.

$^1$H NMR (400 MHz, CDCl$_3$,) δ ppm 0.00 (s, 9H), 0.95-0.99 (m, 2H), 1.04-1.07 (m, 3H), 1.11-1.19 (m, 6H), 1.58-1.82 (m, 4H), 1.84-1.93 (m, 2H), 2.06-2.31 (m, 3H), 2.46-2.55 (m, 2H), 2.55-2.71 (m, 3H), 2.71-2.85 (m, 1H), 3.47-3.75 (m, 7H), 3.80-3.84 (m, 2H), 3.95-4.05 (m, 1H), 5.27 (s, 2H), 5.68-5.76 (m, 1H), 6.98-7.01 (m, 1H), 7.11-7.24 (m, 5H), 7.29-7.36 (m, 2H), 7.44-7.49 (m, 1H), 8.11-8.28 (m, 1H).

LCMS: m/z 774 M+H$^+$.

Preparation 9

N-(1-Benzyl-4,4-diethoxy-piperidin-3-yl)-6-(2-ethyl-5-fluoro-4-hydroxy-phenyl)-1-(tetrahydro-pyran-2-yl)-1H-indazole-3-carboxamidine To a solution of N-(1-benzyl-4,4-diethoxy-piperidin-3-yl)-6-[2-ethyl-5-fluoro-4-(2-trimethylsilanyl-ethoxymethoxy)-phenyl]-1-(tetrahydro-pyran-2-yl)-1H-indazole-3-carboxamidine (Preparation 8, 7.28 g, 9.4 mmol) in ethanol (32 mL) was added concentrated hydrochloric acid (12M, 3.92 mL, 47 mmol) and the resulting solution was allowed to stir at room temperature for 18 hours. The reaction mixture was cooled to 0° C. and neutralised by dropwise addition of a saturated aqueous solution of sodium hydrogen carbonate (150 mL). The mixture was extracted with EtOAc (2×200 mL). The combined organic layers were washed with further saturated aqueous sodium hydrogen carbonate solution (100 mL), dried over MgSO$_4$ and concentrated in vacuo to give the title compound as a foam (6.06 g).

$^1$H NMR (400 MHz, CDCl$_3$) δ ppm 1.01-1.05 (m, 3H), 1.11-1.19 (m, 6H), 1.58-1.82 (m, 3H), 1.84-1.93 (m, 2H), 2.06-2.22 (m, 2H), 2.23-2.35 (m, 1H), 2.43-2.49 (m, 2H), 2.55-2.71 (m, 3H), 2.79-2.89 (m, 1H), 3.44-3.68 (m, 7H), 3.95-4.05 (m, 1H), 4.17-4.26 (m, 1H), 5.68-5.76 (m, 1H), 6.87-6.95 (m, 2H), 7.11-7.24 (m, 4H), 7.29-7.36 (m, 2H), 7.44-7.49 (m, 1H), 8.13-8.24 (m, 1H).

LCMS: m/z 644 M+H$^+$.

Preparation 10

4,4-Diethoxy-3-{[6-[2-ethyl-5-fluoro-4-(2-trimethyl-silanyl-ethoxymethoxy)-phenyl]-1-(tetrahydro-pyran-2-yl)-1H-indazole-3-carboximidoyl]-amino}-piperidine-1-carboxylic acid tert-butyl ester To a solution of 6-[2-ethyl-5-fluoro-4-(2-trimethylsilanyl-ethoxymethoxy)-phenyl]-1-(tetrahydro-pyran-2-yl)-1H-indazole-3-carboximidic acid methyl ester (Preparation 7, 31.4 g, 59.5 mmol) in ethanol (140 mL) was added a solution of 3-amino-4,4-diethoxy-piperidine-1-carboxylic acid tert-butyl ester (US-2004/0229862, 18.02 g, 62.48 mmol) in ethanol (100 mL). Acetic acid (6.81 mL, 119 mmol) was added and the reaction mixture was heated at 50° C. for 18 hours. The reaction mixture was concentrated in vacuo and azeotroped with toluene (100 mL) to give the title compound as a foam (54.7 g).

$^1$H NMR (400 MHz, CDCl$_3$,) δ ppm 0.03 (s, 9H), 0.96-1.00 (m, 2H), 1.05-1.08 (m, 3H), 1.17-1.31 (m, 6H), 1.46 (s, 9H), 1.69-1.75 (m, 2H), 1.93-2.19 (m, 4H), 2.52-2.58 (m, 2H), 3.47-3.58 (m, 2H), 3.59-3.70 (m, 4H), 3.70-3.75 (m, 4H), 3.84-3.88 (m, 2H), 3.92-4.07 (m, 3H), 5.32 (s, 2H), 5.94-5.99 (m, 1H), 7.01 (d, 1H), 7.21 (d, 1H), 7.27 (d, 1H), 7.69 (s, 1H), 8.10 (s, 1H).

LCMS: m/z 784 M+H$^+$.

Preparation 11

5-Ethyl-2-fluoro-4-[3-(4,5,6,7-tetrahydro-1H-imidazo[4,5-c]pyridin-2-yl)-1H-indazol-6-yl]-phenol dihydrochloric acid salt To a solution of 4,4-diethoxy-3-{[6-[2-ethyl-5-fluoro-4-(2-trimethylsilanyl-ethoxymethoxy)-phenyl]-1-(tetrahydro-pyran-2-yl)-1H-indazole-3-carboximidoyl]-amino}-piperidine-1-carboxylic acid tert-butyl ester (Preparation 10, 46.65 g, 55.27 mmol) in ethanol (200 mL) was added concentrated hydrochloric acid (12M, 100 mL, 1.2 mol) and the resulting solution was stirred at room temperature for 18 hours. The reaction mixture was concentrated in vacuo and azeotroped with toluene (100 mL) and DCM (2×100 mL). The resulting gum was dried under vacuum for 3 hours. The crude material was triturated in MeCN (300 mL) and the resulting solid was collected by filtration. The solid was dissolved in ethanol (250 mL) and treated with concentrated hydrochloric acid (12M, 77.2 mL, 927 mmol). The resulting solution was heated at 40° C. for 18 hours, then at 50° C. for 2 hours. The solvents were removed in vacuo and the resulting gum was triturated in MeCN (200 mL). The solid which formed was collected by filtration, washed with further MeCN (200 mL) and dried under vacuum to give the title compound as a beige solid (23.5 g, 88% yield, dihydrochloride salt).

$^1$H NMR (400 MHz, CD$_3$OD) δ ppm 1.05 (t, 3H), 2.53 (q, 2H), 3.22 (t, 2H), 3.73 (t, 2H), 4.55 (s, 2H), 6.90-6.96 (m, 2H), 7.35 (d, 1H), 7.58 (s, 1H), 8.21 (d, 1H).

LCMS: m/z 378 M+H$^+$

Preparation 12

1-Bromo-2-ethyl-5-fluoro-4-methoxy-benzene

To a solution of 4-ethyl-1-fluoro-2-methoxy-benzene (WO 2010/090537, 12.2 g, 79.1 mmol) in MeCN (150 mL) was added a solution of NBS (14.4 g, 80.7 mmol) in MeCN (50 mL). The resulting solution was stirred at room temperature for 18 hours. The solvent was removed in vacuo and the residue was diluted with diethyl ether (150 mL). Precipitated solid was removed by filtration and the filtrate was washed with sodium sulfite aqueous solution (100 mL) and brine (100 mL), dried over MgSO$_4$ and concentrated in vacuo to give the title compound as a yellow oil (18 g) in a 97% yield.

$^1$H NMR (400 MHz, CDCl$_3$) δ ppm 1.21 (t, 3H), 2.69 (q, 2H), 3.87 (s, 3H), 6.82 (d, 1H), 7.24 (d, 1H).

Preparation 13

2-(2-Ethyl-5-fluoro-4-methoxy-phenyl)-4,4,5,5-tetramethyl-[1,3,2]dioxaborolane

To a solution of 1-bromo-2-ethyl-5-fluoro-4-methoxy-benzene (Preparation 12, 18.0 g, 77.2 mmol) in dioxane (100 mL) were added SPhos (4.12 g, 10.0 mmol), 4,4,5,5-tetramethyl-1,3,2-dioxaborolane (14.8 g, 116 mmol) and triethylamine (10.7 mL, 77.2 mmol). The reaction mixture was degassed with nitrogen prior to the addition of dichlorobis (acetonitrile)palladium (II) (801 mg, 3.09 mmol). The reaction mixture was then heated at 110° C. for 18 hours, cooled to room temperature and filtered through a pad of Celite, washing with EtOAc. The solvent was removed in vacuo and the residue was redissolved in EtOAc (30 mL) and washed with water (30 mL). The organic layer was dried over sodium sulfate and concentrated in vacuo. The crude material was triturated with methanol and the resulting solid was collected by filtration to give the title compound as a beige solid (13.8 g) in a 64% yield.

$^1$H NMR (400 MHz, CDCl$_3$) δ ppm 1.18 (t, 3H), 1.32 (s, 12H), 2.87 (q, 2H), 3.89 (s, 3H), 6.76 (d, 1H), 7.46 (d, 1H).

LCMS: m/z 281 M+H$^+$.

Preparation 14

6-(2-Ethyl-5-fluoro-4-methoxy-phenyl)-1-(tetrahydro-pyran-2-yl)-1H-indazole

To a solution of 6-bromo-1-(tetrahydro-pyran-2-yl)-1H-indazole (WO 2010/027500, 2.25 g, 8.0 mmol) and 2-(2-ethyl-5-fluoro-4-methoxy-phenyl)-4,4,5,5-tetramethyl-[1,3,2]dioxaborolane (Preparation 13, 2.24 g, 8.0 mmol) in dioxane (32 mL) was added potassium phosphate (5.1 g, 24 mmol) as a solution in water (8 mL). The reaction mixture was degassed with nitrogen and treated with tetrakis (triphenylphosphine) palladium(0) (1.85 g, 1.6 mmol). The reaction mixture was heated at 110° C. for 18 hours, cooled to room temperature and filtered through a pad of Arbocel®, washing with EtOAc (2×100 mL). The filtrate was washed with water (100 mL), dried over MgSO$_4$ and concentrated in vacuo. The crude material was purified by column chromatography on silica gel eluting with 10% EtOAc in heptane to give the title compound as a white solid (2.024 g) in a 71% yield.

$^1$H NMR (400 MHz, CDCl$_3$) δ ppm 1.12 (t, 3H), 1.62-1.81 (m, 3H), 2.07-2.17 (m, 2H), 2.54-2.63 (m, 3H), 3.70-3.76 (m, 1H), 3.95 (s, 3H), 4.01-4.07 (m, 1H), 5.71 (dd, 1H), 6.90 (d, 1H), 7.01 (d, 1H), 7.09 (dd, 1H), 7.46 (s, 1H), 7.71 (d, 1H), 8.05 (s, 1H).

Preparation 15

6-(2-Ethyl-5-fluoro-4-methoxy-phenyl)-1H-indazole

To a solution of 6-(2-ethyl-5-fluoro-4-methoxy-phenyl)-1H-(tetrahydro-pyran-2-yl)-1H-indazole (Preparation 14, 1.8 g, 5.07 mmol) in methanol (100 mL) was added concentrated hydrochloric acid (12M) and the resulting solution was heated at 60° C. overnight, cooled to room temperature and concentrated in vacuo. The residue was redissolved in EtOAc (50 mL) and washed with saturated sodium hydrogen carbonate aqueous solution (50 mL). The organic layer was dried over MgSO$_4$ and concentrated in vacuo to yield the title product (1.465 g) in 95% yield.

$^1$H NMR (400 MHz, CDCl$_3$) δ ppm 1.09 (t, 3H), 2.56 (q, 2H), 3.95 (s, 3H), 6.90 (d, 1H), 6.98 (d, 1H), 7.10 (dd, 1H), 7.38 (s, 1H), 7.76 (d, 1H), 8.14 (br s, 1H), 10.69 (br s, 1H)

LCMS: m/z 271 M+H$^+$.

Preparation 16

6-(2-Ethyl-5-fluoro-4-methoxy-phenyl)-3-iodo-1H-indazole

To a solution of 6-(2-ethyl-5-fluoro-4-methoxy-phenyl)-1H-indazole (Preparation 15, 1.46 g, 5.4 mmol) in DMF (20 mL) was added KOH (1.14 g, 20.3 mmol) and the mixture was stirred for 5 minutes. A solution of iodine (2.75 g, 10.8 mmol) in DMF (5 mL) was slowly added and the reaction was stirred at room temperature for 30 minutes. The reaction mixture was diluted with water (100 mL) and extracted with EtOAc (100 mL). The organic layer was washed with water (2×100 mL) and saturated sodium metabisulfite aqueous solution (100 mL), dried over MgSO$_4$ and concentrated in vacuo to furnish the title compound (1.94 g) in a 91% yield.

$^1$H NMR (400 MHz, CDCl$_3$) δ ppm 1.08 (t, 3H), 2.55 (q, 2H), 3.95 (s, 3H), 6.90 (d, 1H), 6.97 (d, 1H), 7.16 (dd, 1H), 7.37 (s, 1H), 7.52 (d, 1H), 10.64 (br s, 1H).

LCMS: m/z 397 M+H$^+$.

Preparation 17

6-(2-Ethyl-5-fluoro-4-methoxy-phenyl)-3-iodo-1-(tetrahydro-pyran-2-yl)-1H-indazole To a solution of 6-(2-ethyl-5-fluoro-4-methoxy-phenyl)-3-iodo-1H-indazole (Preparation 16, 1.94 g, 4.9 mmol) in DCM (10 mL) was added p-TsOH (187 mg, 982 µmol) and the mixture was cooled to 0° C. 3,4-Dihydro-2H-pyran (660 µL, 7.4 mmol) was added dropwise to the solution and the reaction was stirred at room temperature overnight. The reaction mixture was diluted with DCM (5 mL) and washed with saturated sodium hydrogen carbonate aqueous solution (20 mL). The organic layer was dried over MgSO$_4$ and concentrated in vacuo to yield a black oil. The residue was purified by column chromatography (Biotage SNAP 10 g) eluting with a gradient of 20% EtOAc in heptane to give the title compound as a colourless oil (2.09 g) in an 89% yield.

$^1$H NMR (400 MHz, CDCl$_3$) δ ppm 1.11 (t, 3H), 1.60-1.64 (m, 1H), 1.72-1.76 (m, 2H), 2.02-2.10 (m, 2H), 2.50-2.58 (m, 3H), 3.69-3.73 (m, 1H), 3.95 (s, 3H), 4.01-4.05 (m, 1H), 5.68 (dd, 1H), 6.90 (d, 1H), 7.10 (d, 1H), 7.15 (dd, 1H), 7.42-7.46 (m, 2H).

LCMS: m/z 481 M+H$^+$.

Preparation 18

6-(2-Ethyl-5-fluoro-4-methoxy-phenyl)-1H-(tetrahydro-pyran-2-yl)-3-trimethylstannanyl-1H-indazole To a solution of 6-(2-ethyl-5-fluoro-4-methoxy-phenyl)-3-iodo-1-(tetrahydro-pyran-2-yl)-1H-indazole (Preparation 17, 2.09 g, 4.35 mmol) in toluene (24 mL) was added 1,1,1,2,2,2-hexamethyl-distannane (1 mL, 4.79 mmol) followed by tetrakis (triphenylphosphine) palladium(0) (100 mg, 87 µmol). The reaction mixture was degassed with nitrogen and heated at 100° C. for 18 hours. The reaction was then cooled to room temperature and concentrated in vacuo. The residue was purified by column chromatography on silica gel eluting with 10% EtOAc in heptane to give the title compound as a colourless oil (1.47 g) in a 65% yield.

$^1$H NMR (400 MHz, CDCl$_3$) δ ppm 0.47 (t, 9H), 1.12 (t, 3H), 1.60-1.64 (m, 1H), 1.73-1.78 (m, 2H), 2.05-2.18 (m, 2H), 2.57 (q, 2H), 2.59-2.67 (m, 1H), 3.70-3.76 (m, 1H), 3.95 (s, 3H), 4.06-4.09 (m, 1H), 5.74 (dd, 1H), 6.91 (d, 1H), 7.00-7.06 (m, 2H), 7.48 (s, 1H), 7.68 (s, 1H).

LCMS: m/z 519 M+H$^+$.

Preparation 19

6,7-Dihydro-4H-imidazo[4,5-c]pyridine-1,5-dicarboxylic acid di-tert-butyl ester

To a solution of 4,5,6,7-tetrahydro-1H-imidazo[4,5-c]pyridine (21.3 g, 109 mmol) in methanol (250 mL) was added DIPEA (47.3 mL, 272 mmol) and a solution of di-tert-butyl dicarbonate (59.3 g, 272 mmol) in methanol (130 mL). The reaction mixture was stirred at room temperature for 18 hours and concentrated in vacuo to yield an oil. The residue was redissolved in EtOAc (500 mL) and the resulting solution was washed with water (500 mL), dried over MgSO$_4$ and concentrated in vacuo. The residue was purified by column chromatography on silica gel eluting with 30% EtOAc in DCM to yield the title compound as a white solid (26.85 g) in 76% yield.

$^1$H NMR (400 MHz, CDCl$_3$) δ ppm 1.48 (s, 9H), 1.60 (s, 9H), 2.61-2.92 (m, 2H), 3.62-3.72 (m, 2H), 4.59-4.65 (m, 2H), 7.98 (s, 1H).

Preparation 20

1,4,6,7-Tetrahydro-imidazo[4,5-c]pyridine-5-carboxylic acid tert-butyl ester

To a solution of 6,7-dihydro-4H-imidazo[4,5-c]pyridine-1,5-dicarboxylic acid di-tert-butyl ester (Preparation 19, 26.8 g, 82.9 mmol) in methanol (210 mL) was added 1M sodium hydroxide aqueous solution (170 mL, 170 mmol). The resulting mixture was stirred at room temperature for 1 hour. The reaction mixture was diluted with 10% citric acid aqueous solution (250 mL), basified to pH8 and extracted with DCM (2×500 mL). The combined organic layers were dried over MgSO$_4$ and concentrated in vacuo to give the title compound as a brown foam (18.5 g) in a 97% yield.

$^1$H NMR (400 MHz, CDCl$_3$) δ ppm 1.47 (s, 9H), 2.64-2.72 (m, 2H), 3.68-3.75 (m, 2H), 4.43-4.53 (m, 2H), 7.52 (s, 1H).

Preparation 21

2-Iodo-1,4,6,7-tetrahydro-imidazo[4,5-c]pyridine-5-carboxylic acid tert-butyl ester To a solution of 1,4,6,7-tetrahydro-imidazo[4,5-c]pyridine-5-carboxylic acid tert-butyl ester (Preparation 20, 18 g, 80.62 mmol) in THF (300 mL) was added NIS (27.2 g, 121 mmol). The reaction mixture was stirred at room temperature for 1 hour. The reaction mixture was diluted with EtOAc (800 mL), washed with sodium thiosulfate aqueous solution (3×700 mL) and brine (500 mL), dried over MgSO$_4$ and concentrated in vacuo to give the title compound as a yellow solid (18.25 g) in a 64.8% yield.

$^1$H NMR (400 MHz, CDCl$_3$) δ ppm 1.46 (s, 9H), 2.66-2.74 (m, 2H), 3.64-3.75 (m, 2H), 4.42-4.54 (m, 2H).

Preparation 22

2-Iodo-1-(2-trimethylsilanyl-ethoxymethyl)-1,4,6,7-tetrahydro-imidazo[4,5-c]pyridine-5-carboxylic acid tert-butyl ester To a solution of 2-iodo-1,4,6,7-tetrahydro-imidazo[4,5-c]pyridine-5-carboxylic acid tert-butyl ester (Preparation 21, 17.25 g, 49.4 mmol) in THF (250 mL) was added NaH (60% in paraffin oil, 2.08 g, 51.9 mmol) and the resulting solution was stirred at room temperature for 1.5 hours. The reaction mixture was cooled to 0° C. and SEM-Cl (9.18 mL, 51.9 mmol) was added dropwise. The reaction was stirred at room temperature for 18 hours, cooled to 0° C. and quenched carefully with water (500 mL). The resulting solution was extracted with EtOAc (2×500 mL) and the combined organics layers were dried over MgSO$_4$, filtered through a pad of silica and concentrated in vacuo to give the title compound (23.4 g) in a 99% yield.

$^1$H NMR (400 MHz, CDCl$_3$) δ ppm 0.00 (s, 9H), 0.90-0.95 (m, 2H), 1.47 (s, 9H), 2.64-2.76 (m, 2H), 3.54 (t, 2H), 3.63-3.75 (m, 2H), 4.43-4.57 (m, 2H), 5.15 (s, 2H).

Preparation 23

2-[6-(2-Ethyl-5-fluoro-4-methoxy-phenyl)-1H-(tetrahydro-pyran-2-yl)-1H-indazol-3-yl]-1-(2-trimethylsilanyl-ethoxymethyl)-1,4,6,7-tetrahydro-imidazo[4,5-c]pyridine-5-carboxylic acid tert-butyl ester To a solution of 6-(2-ethyl-5-fluoro-4-methoxy-phenyl)-1H-(tetrahydro-pyran-2-yl)-3-trimethylstannanyl-1H-indazole (Preparation 18, 735 mg, 1.53 mmol) in toluene (6 mL) was added 2-iodo-1-(2-trimethylsilanyl-ethoxymethyl)-1,4,6,7-tetrahydro-imidazo[4,5-c]pyridine-5-carboxylic acid tert-butyl ester (Preparation 22, 805 mg, 1.68 mmol), copper (I) iodide (60 mg, 310 μmol) and tetrakis (triphenylphosphine) palladium(0) (173 mg, 150 μmol). The reaction mixture was degassed with nitrogen, heated at 100° C. for 18 hours, cooled to room temperature and concentrated in vacuo. The residue was purified by column chromatography on silica gel eluting with 20% EtOAc in toluene to give the title compound as a foam (801 mg) in a 74% yield.

$^1$H NMR (400 MHz, CDCl$_3$) δ ppm−0.12 (s, 9H), 0.81-0.90 (m, 2H), 1.10 (t, 3H), 1.50 (s, 9H), 1.67-1.83 (m, 3H), 2.12-2.20 (m, 2H), 2.57 (q, 2H), 2.58-2.60 (m, 1H), 2.81-2.84 (m, 2H), 3.49-3.56 (m, 2H), 3.72-3.82 (m, 3H), 3.95 (s, 3H), 4.01-4.04 (m, 1H), 4.60-4.63 (m, 2H), 5.74-5.76 (m, 1H), 5.83-5.86 (m, 1H), 5.98-6.00 (m, 1H), 6.90 (d, 1H), 7.03 (d, 1H), 7.19 (dd, 1H), 7.46 (s, 1H), 8.42 (d, 1H).

LCMS: m/z 706 M+H$^+$.

Preparation 24

2-[6-(2-Ethyl-5-fluoro-4-methoxy-phenyl)-1H-indazol-3-yl]-4,5,6,7-tetrahydro-1H-imidazo[4,5-c]pyridine trihydrochloride salt To a solution of 2-[6-(2-ethyl-5-fluoro-4-methoxy-phenyl)-1-(tetrahydro-pyran-2-yl)-1H-indazol-3-yl]-1-(2-trimethylsilanyl-ethoxymethyl)-1,4,6,7-tetrahydro-imidazo[4,5-c]pyridine-5-carboxylic acid tert-butyl ester (Preparation 23, 801 mg, 1.13 mmol) in methanol (20 mL) was added concentrated hydrochloric acid (12M, 8 mL) and the resulting solution was heated at 60° C. for 18 hours. The reaction mixture was cooled to room temperature and concentrated in vacuo to furnish the title compound (739 mg).

$^1$H NMR (400 MHz, CD$_3$OD) δ ppm 1.04 (t, 3H), 2.55 (q, 2H), 3.25-3.26 (m, 2H), 3.62-3.65 (m, 2H), 3.89 (s, 3H), 4.48-4.52 (m, 2H), 6.94 (d, 1H), 7.02 (d, 1H), 7.30-7.32 (m, 1H), 7.56 (s, 1H), 8.27-8.29 (m, 1H).

LCMS: m/z 392 M+H$^+$.

Preparation 25

5-Ethyl-2-fluoro-4-[3-(4,5,6,7-tetrahydro-1H-imidazo[4,5-c]pyridin-2-yl)-1H-indazol-6-yl]-phenol trihydrobromide salt A 1M solution of boron tribromide in DCM (4.54 mL, 4.54 mmol) was added dropwise to a solution of 2-[6-(2-ethyl-5-fluoro-4-methoxy-phenyl)-1H-indazol-3-yl]-4,5,6,7-tetrahydro-1H-imidazo[4,5-c]pyridine (Preparation 24, 739 mg, 1.13 mmol) in DCM (10 mL) at 0° C. The resulting solution was stirred at room temperature for 18 hours. Further boron tribromide (4.54 mL, 4.54 mmol) was added dropwise and the reaction was allowed to stir at room temperature for 5 hours. Precipitated solid was collected by filtration, washed with tBME, then triturated with EtOAc to yield the title compound as the trihydrobromide salt (665 mg) in a 94% yield.

$^1$H NMR (400 MHz, CD$_3$OD) δ ppm 1.05 (t, 3H), 2.52 (q, 2H), 3.25-3.26 (m, 2H), 3.75-3.76 (m, 2H), 4.60-4.61 (m, 2H), 6.89-6.96 (m, 2H), 7.32-7.41 (m, 1H), 7.58-7.59 (m, 1H), 8.22-8.23 (m, 1H).

LCMS: m/z 378 M+H$^+$.

Preparation 26

4,5,7,8-Tetrahydro-imidazo[4,5-d]azepine-1,6-dicarboxylic acid di-tert-butyl ester To a solution of 1,4,5,6,7,8-Hexahydro-imidazo[4,5-d]azepine (WO 2000/063208; 5.0 g, 23.5 mmol) in methanol (60 mL) was added DIPEA (5.6 mL, 59.6 mmol) and a solution of BOC-anhydride (13.07 g, 59.6 mmol) in methanol (30 mL). The reaction mixture was stirred at room temperature for 18 hours and concentrated in vacuo to yield an oil. The residue was redissolved in DCM (250 mL) and the resulting solution was washed with water (100 mL) and saturated aqueous ammonium chloride solution (100 mL), dried over MgSO$_4$ and concentrated in vacuo. The residue was purified by column chromatography on silica gel eluting with 50% EtOAc in heptane to yield the title compound as a brown oil (6.87 g) in 85% yield.

$^1$H NMR (400 MHz, CDCl$_3$) δ ppm 1.40 (s, 9H), 1.53 (s, 9H), 2.84-2.87 (m, 2H), 3.10-3.12 (m, 2H), 3.50-3.62 (m, 4H), 7.87 (s, 1H).

Preparation 27

4,5,7,8-Tetrahydro-1H-imidazo[4,5-d]azepine-6-carboxylic acid tert-butyl ester

To a solution of 4,5,7,8-tetrahydro-imidazo[4,5-d]azepine-1,6-dicarboxylic acid di-tert-butyl ester (Preparation 26, 6.87 g, 20.37 mmol) in methanol (60 mL) was added an aqueous 1M solution of sodium hydroxide (40.7 mL, 40.7 mmol). The resulting mixture was stirred at room temperature for 2 hours and then concentrated in vacuo. The residue was partitioned between DCM (100 mL) and water (100 mL). The organic layer was dried over MgSO$_4$ and concentrated in vacuo to give the title compound as a brown foam (4.8 g) in a 99% yield.

$^1$H NMR (400 MHz, CDCl$_3$) δ ppm 1.46 (s, 9H), 2.78-2.83 (m, 4H), 3.56-3.62 (m, 4H), 7.40 (s, 1H).

Preparation 28

2-Iodo-4,5,7,8-tetrahydro-1H-imidazo[4,5-d]azepine-6-carboxylic acid tert-butyl ester To a solution of 4,5,7,8-tetrahydro-1H-imidazo[4,5-d]azepine-6-carboxylic acid tert-butyl ester (Preparation 27, 4.8 g, 20.23 mmol) in THF (60 mL) was added NIS (4.78 g, 21.24 mmol). The reaction was stirred at room temperature for 18 hours and the solvent was then removed in vacuo. The residue was dissolved in EtOAc (200 mL) and the resulting solution was washed with sodium thiosulfate solution (150 mL). The aqueous layer was re-extracted with EtOAc (150 mL) and the combined organic layers were washed with brine (150 mL), dried over MgSO$_4$ and concentrated in vacuo to give the title compound as a tan solid (6.14 g) in an 84% yield.

$^1$H NMR (400 MHz, CDCl$_3$) δ ppm 1.46 (s, 9H), 2.79-2.87 (m, 4H), 3.53-3.59 (m, 4H).

LCMS: m/z 364 M+H$^+$.

Preparation 29

2-Iodo-1-(2-trimethylsilanyl-ethoxymethyl)-4,5,7,8-tetrahydro-1H-imidazo[4,5-d]azepine-6-carboxylic acid tert-butyl ester To a solution of 2-iodo-4,5,7,8-tetrahydro-1H-imidazo[4,5-d]azepine-6-carboxylic acid tert-butyl ester (Preparation 28, 2.2 g, 6.06 mmol) in THF (35 mL) was added NaH (60% in paraffin oil, 254 mg, 6.36 mmol) and the resulting solution was stirred at room temperature for 1.5 hours. The reaction mixture was cooled to 0° C. and SEM-Cl (1.13 mL, 6.36 mmol) was added dropwise.

The reaction mixture was stirred at room temperature for 18 hours and then cooled to 0° C. and quenched carefully with water (100 mL). The resulting solution was extracted with EtOAc (2×100 mL) and the combined organic layers were dried over MgSO$_4$ and concentrated in vacuo. The residue was purified by column chromatography (Biotage SNAP 100 g) eluting with 40% EtOAc in DCM to give the title compound (2.34 g) in a 78% yield.

$^1$H NMR (400 MHz, CDCl$_3$) δ ppm−0.01 (s, 9H), 0.89-0.93 (m, 2H), 1.46 (s, 9H), 2.82-2.92 (m, 4H), 3.54-3.66 (m, 6H), 5.16 (s, 2H).

LCMS: m/z 494 M+H$^+$.

Preparation 30

2-[6-(2-Ethyl-5-fluoro-4-methoxy-phenyl)-1-(tetrahydro-byran-2-yl)-1H-indazol-3-yl]-1-(2-trimethylsilanyl-ethoxymethyl)-4,5,7,8-tetrahydro-1H-imidazo[4,5-d]azepine-6-carboxylic acid tert-butyl ester To a solution of 6-(2-ethyl-5-fluoro-4-methoxy-phenyl)-1-(tetrahydro-pyran-2-yl)-3-trimethylstannanyl-1H-indazole (Preparation 18, 735 mg, 1.53 mmol) in toluene (6 mL) was added 2-iodo-1-(2-trimethylsilanyl-ethoxymethyl)-4,5,7,8-tetrahydro-1H-imidazo[4,5-d]azepine-6-carboxylic acid tert-butyl ester (Preparation 29, 829 mg, 1.68 mmol), copper (I) iodide (60 mg, 310 µmol) and tetrakis (triphenylphosphine) palladium(0) (173 mg, 150 µmol). The reaction mixture was degassed with nitrogen, heated at 100° C. for 18 hours, cooled to room temperature and concentrated in vacuo. The residue was purified by column chromatography on silica gel eluting with 20% EtOAc in toluene to give the title compound as a foam (633 mg) in a 57% yield.

$^1$H NMR (400 MHz, CDCl$_3$) δ ppm−0.13 (s, 9H), 0.80-0.84 (m, 2H), 1.09 (t, 3H), 1.50 (s, 9H), 1.65-1.84 (m, 3H), 2.10-2.18 (m, 2H), 2.56 (q, 2H), 2.58-2.64 (m, 1H), 2.91-3.08 (m, 4H), 3.50-3.54 (m, 2H), 3.63-3.76 (m, 5H), 3.95 (s, 3H), 3.99-4.04 (m, 1H), 5.74 (dd, 1H), 5.83-5.88 (m, 1H), 5.97-6.03 (m, 1H), 6.90 (d, 1H), 7.03 (d, 1H), 7.18 (dd, 1H), 7.45 (s, 1H), 8.40-8.43 (m, 1H).

LCMS: m/z 720 M+H$^+$.

Preparation 31

2-[6-(2-Ethyl-5-fluoro-4-methoxy-phenyl)-1H-indazol-3-yl]-1,4,5,6,7,8-hexahydro-imidazo[4,5-d]azepine trihydrochloride salt To a solution of 2-[6-(2-ethyl-5-fluoro-4-methoxy-phenyl)-1-(tetrahydro-pyran-2-yl)-1H-indazol-3-yl]-1-(2-trimethylsilanyl-ethoxymethyl)-4,5,7,8-tetrahydro-1H-imidazo[4,5-d]azepine-6-carboxylic acid tert-butyl ester (Preparation 30, 633 mg, 879 µmol) in methanol (20 mL) was added concentrated hydrochloric acid (12M, 8 mL) and the resulting solution was heated at 60° C. for 18 hours. A further amount of concentrated hydrochloric acid (12M, 4 mL) was added and the reaction mixture was heated at 60° C. for a further 18 hours. The reaction mixture was cooled to room temperature and concentrated in vacuo to furnish the title compound (410 mg).

$^1$H NMR (400 MHz, CD$_3$OD) δ ppm 1.07 (t, 3H), 2.60 (q, 2H), 3.35-3.37 (m, 4H), 3.62-3.63 (m, 4H), 3.93 (s, 3H), 6.99 (d, 1H), 7.07 (d, 1H), 7.35 (d, 1H), 7.59 (s, 1H), 8.24 (m, 1H).

LCMS: m/z 406 M+H$^+$.

Preparation 32

5-Ethyl-2-fluoro-4-[3-(1,4,5,6,7,8-hexahydro-imidazo[4,5-d]azepin-2-yl)-1H-indazol-6-yl]-phenol trihydrobromide salt A 1M solution of boron tribromide in DCM (3.18 mL, 3.18 mmol) was added dropwise to a solution of 2-[6-(2-ethyl-5-fluoro-4-methoxy-phenyl)-1H-indazol-3-yl]-1,4,5,6,7,8-hexahydro-imidazo[4,5-d]azepine (Preparation 31, 410 mg, 796 µmol) in DCM (10 mL) at 0° C. The resulting solution was stirred at room temperature for 18 hours. The precipitated solid was collected by filtration, washed with tBME, then triturated with EtOAc to yield the title compound (380 mg) in a 75% yield.

$^1$H NMR (400 MHz, CD$_3$OD) ppm 1.05 (t, 3H), 2.52 (q, 2H), 3.36-3.39 (m, 4H), 3.63-3.66 (m, 4H), 6.89-6.96 (m, 2H), 7.34 (d, 1H), 7.57 (s, 1H), 8.22 (d, 1H).

LCMS: m/z 392 M+H$^+$.

Preparation 33

(2-Bromo-4-fluoro-5-methoxy-phenyl)-methanol

To a solution of (4-fluoro-3-methoxy-phenyl)-methanol (10.0 g, 64.04 mmol) in MeCN (160 mL) was added a solution of NBS (11.4 g, 64.04 mmol) in MeCN (50 mL) and the resulting mixture was stirred at room temperature for 18 hours. The reaction mixture was concentrated in vacuo and the residue was suspended in diethyl ether (200 mL). Solid material was removed by filtration and washed with further diethyl ether. The filtrate was washed with water (200 mL) and brine (100 mL), dried over MgSO$_4$ and concentrated in vacuo to give the title compound as a white solid (14.4 g) in a 96% yield.

$^1$H NMR (400 MHz, CDCl$_3$) δ ppm 1.94 (t, 1H), 3.90 (s, 3H), 4.70 (d, 2H), 7.14 (d, 1H), 7.27 (d, 1H).

Preparation 34

1-Bromo-2-bromomethyl-5-fluoro-4-methoxy-benzene

Phosphorus tribromide (11.56 mL, 122.5 mmol) was added to a solution of (2-bromo-4-fluoro-5-methoxy-phenyl)-methanol (Preparation 33, 14.4 g, 61.26 mmol) in DCM (235 mL) at 0° C. The reaction was allowed to warm to room temperature and stirred at that temperature for 18 hours. The reaction mixture was cooled to 0° C. and quenched by slow addition of saturated sodium hydrogen carbonate aqueous solution until effervescence had ceased. The layers were separated and the aqueous layer was extracted with DCM (2×100 mL). The combined organic layers were dried over MgSO$_4$ and concentrated in vacuo to give the title compound as a white solid (17.48 g) in a 96% yield.

$^1$H NMR (400 MHz, CDCl$_3$) δ ppm 3.89 (s, 3H), 4.55 (s, 2H), 7.04 (d, 1H), 7.29 (d, 1H).

Preparation 35

1-Bromo-5-fluoro-4-methoxy-2-(2,2,2-trifluoro-ethyl)-benzene

To a solution of 1-bromo-2-bromomethyl-5-fluoro-4-methoxy-benzene (Preparation 34, 10.84 g, 36.4 mmol) in DMF (80 mL) was added copper (I) iodide (1.746 g, 9.09 mmol) and the solution was degassed with nitrogen. To this solution was added difluoro-fluorosulfonyl-acetic acid methyl ester (11.57 mL, 90.9 mmol) and the resulting reaction mixture was heated at 120° C. for 4 hours. The reaction mixture was cooled to 0° C., diluted with EtOAc (60 mL) and stirred for 10 minutes at 0° C. A solution of ammonium hydroxide (60 mL) was added dropwise and the mixture was stirred as it warmed from 0° C. to room temperature over 20 minutes. Ethyl acetate (200 mL) and water (100 mL) were added and the layers were separated. The aqueous layer was further extracted with EtOAc (2×100 mL). The combined organic layers were washed with water (100 mL) and brine (100 mL), dried over Na$_2$SO$_4$ and concentrated in vacuo. The crude residue was purified by column chromatography on silica gel eluting with 20% EtOAc in heptane to give the title compound as a yellow solid (7.356 g) in a 70% yield.

$^1$H NMR (400 MHz, CDCl$_3$) δ ppm 3.56 (q, 2H), 3.89 (s, 3H), 6.94 (d, 1H), 7.32 (d, 1H).

LCMS: m/z 288 M+H$^+$.

Preparation 36

2-[5-Fluoro-4-methoxy-2-(2,2,2-trifluoro-ethyl)-phenyl]-4,4,5,5-tetramethyl-1,3,2]dioxaborolane To a solution of 1-bromo-5-fluoro-4-methoxy-2-(2,2,2-trifluoro-ethyl)-benzene (Preparation 35, 7.07 g, 26.82 mmol) in dioxane (100 mL) was added 4,4,5,5,4',4',5',5'-octamethyl-[2,2']bi[[1,3,2]dioxaborolanyl] (8.17 g, 32.18 mmol) and KOAc (7.9 g, 80.46 mmol). The mixture was degassed with nitrogen prior to the addition of [1,1-bis(diphenylphosphino)ferrocene]-dichloropalladium(II) (2.3 g, 2.68 mmol). The reaction mixture was stirred at 110° C. for 18 hours, then cooled to room temperature and concentrated in vacuo. The residue was dissolved in methanol and filtered through Arbocel®, washing with methanol. The filtrate was concentrated in vacuo and then partitioned between EtOAc (200 mL) and water (200 mL). The aqueous layer was extracted with further EtOAc (2×100 mL). The combined organic layers were washed with water (200 mL) and brine (150 mL), dried over Na$_2$SO$_4$ and concentrated in vacuo to give the title compound as an oil (8.96 g) in a 100% yield.

$^1$H NMR (400 MHz, CDCl$_3$) δ ppm 1.31 (s, 12H), 3.78 (q, 2H), 3.95 (s, 3H), 6.85 (d, 1H), 7.53 (d, 1H).

Preparation 37

6-[5-Fluoro-4-methoxy-2-(2,2,2-trifluoro-ethyl)-phenyl]-1-(tetrahydro-pyran-2-yl)-1H-indazole-3-carbonitrile To a solution of 6-bromo-1-(tetrahydro-pyran-2-yl)-1H-indazole-3-carbonitrile (Preparation 2, 3.99 g, 13.03 mmol) and 2-[5-fluoro-4-methoxy-2-(2,2,2-trifluoro-ethyl)-phenyl]-4,4,5,5-tetramethyl-[1,3,2]dioxaborolane (Preparation 36, 7.46 g, 15.63 mmol) in dioxane (60 mL) was added a solution of potassium phosphate (18.8 g, 39.09 mmol) in water (12 mL). The mixture was degassed with nitrogen, treated with tetrakis (triphenylphosphine) palladium(0) (3.01 g, 2.6 mmol) and heated at 110° C. for 18 hours. The reaction mixture was concentrated in vacuo and the residue was redissolved in EtOAc (500 mL) and filtered through Arbocel®, washing with EtOAc (2×500 mL). The combined organic phases were washed with water (300 mL), dried over $MgSO_4$ and concentrated in vacuo to give a brown oil. The residue was purified by column chromatography on silica gel, eluting with 25% EtOAc in heptanes, to give the title compound (1.737 g) in a 31% yield.

$^1$H NMR (400 MHz, $CDCl_3$) δ ppm 1.68-1.80 (m, 3H), 2.11-2.17 (m, 2H), 2.45-2.53 (m, 1H), 3.27-3.41 (m, 3H), 3.74 (m, 1H), 3.96 (s, 3H), 5.80 (dd, 1H), 7.06 (m, 2H), 7.24 (m, 1H), 7.84 (s, 1H), 7.87 (d, 1H).

Preparation 38

6-[5-Fluoro-4-methoxy-2-(2,2,2-trifluoro-ethyl)-phenyl]-1-(tetrahydro-pyran-2-yl)-1H-indazole-3-carboximidic acid methyl ester To a solution of 6-[5-fluoro-4-methoxy-2-(2,2,2-trifluoro-ethyl)-phenyl]-1-(tetrahydro-pyran-2-yl)-1H-indazole-3-carbonitrile (Preparation 37, 1.737 g, 4.00 mmol) in methanol (40 mL) was added sodium methoxide (648 mg, 12.0 mmol) and the reaction mixture was stirred at room temperature for 18 hours. The reaction mixture was partitioned between EtOAc (50 mL) and water (50 mL) and the aqueous layer was extracted with further EtOAc (2×50 mL). The combined organic layers were dried over $MgSO_4$ and concentrated in vacuo to give the title compound as an oily solid (1.64 g) in an 88% yield.

$^1$H NMR (400 MHz, $CDCl_3$) δ ppm 1.63-1.78 (m, 3H), 2.07-2.18 (m, 2H), 2.53-2.61 (m, 1H), 3.28-3.42 (m, 3H), 3.96 (s, 3H), 4.00-4.04 (m, 1H), 4.07 (s, 3H), 5.74 (dd, 1H), 7.05 (d, 1H), 7.09 (d, 1H), 7.14 (dd, 1H), 7.52 (s, 1H), 8.10 (d, 1H).

Preparation 38

2-{6-[5-Fluoro-4-methoxy-2-(2,2,2-trifluoro-ethyl)-phenyl]-1H-indazol-3-yl}-4,5,6,7-tetrahydro-3H-imidazo[4,5-c]pyridine trihydrochloride salt To a solution of 6-[5-fluoro-4-methoxy-2-(2,2,2-trifluoro-ethyl)-phenyl]-1-(tetrahydro-pyran-2-yl)-1H-indazole-3-carboximidic acid methyl ester (Preparation 37, 1.64 g, 3.78 mmol) in ethanol (5 mL) was added a solution of 3-amino-4,4-diethoxy-piperidine-1-carboxylic acid tert-butyl ester (US-2004/0229862, 1.15 g, 3.97 mmol) in ethanol (7.5 mL). Acetic acid (430 μL, 7.56 mmol) was added and the reaction mixture was heated at 50° C. for 18 hours and then concentrated in vacuo to give a brown oil. The oil was dissolved in ethanol (15 mL) and the resulting solution was treated with concentrated hydrochloric acid (12M, 4.75 mL, 56.7 mmol) and then heated at 80° C. for 18 hours. The solvent was removed in vacuo to yield the title compound (2.03 g) in a 97% yield.

$^1$H NMR (400 MHz, $CD_3OD$) δ ppm 3.20-3.26 (m, 2H), 3.40-3.54 (m, 2H), 3.66-3.75 (m, 2H), 3.80 (s, 3H), 4.51-4.55 (m, 2H), 7.15 (d, 1H), 7.24 (d, 1H), 7.33 (d, 1H), 7.62 (s, 1H), 8.27 (d, 1H)

LCMS: m/z 446 M+H$^+$. .

Preparation 39

2-Fluoro-4-[3-(4,5,6,7-tetrahydro-1H-imidazo[4,5-c]pyridin-2-yl)-1H-indazol-6-yl]-5-(2,2,2-trifluoro-ethyl)-phenol dihydrobromide salt Boron tribromide (750 μL, 7.83 mmol) was added driowuse to a solution of 2-{6-[5-fluoro-4-methoxy-2-(2,2,2-trifluoro-ethyl)-phenyl]-1H-indazol-3-yl}-4,5,6,7-tetrahydro-3H-imidazo[4,5-c]pyridine trihydrochloride salt (Preparation 38, 2.03 g, 3.66 mmol) in DCM (25 mL) at 0° C. The resulting solution was stirred at room temperature for 18 hours. Further boron tribromide (2 mL, 20.7 mmol) was added dropwise and the reaction mixture was allowed to stir at room temperature for 18 hours. The precipitated solid was collected by filtration, washed with DCM and triturated with EtOAc to yield the title compound as the dihydrobromide salt (1.56 g) in a 67% yield.

$^1$H NMR (400 MHz, $CD_3OD$) δ ppm 3.24 (dd, 2H), 3.41 (q, 2H), 3.75 (dd, 2H), 4.58 (s, 2H), 7.05-7.09 (m, 2H), 7.34 (d, 1H), 7.60 (s, 1H), 8.26 (d, 1H).

LCMS: m/z 432 M+H$^+$.

Preparation 40

5-Hydroxy-pyrazine-2-carboxylic acid methyl ester

Thionyl chloride (152 mL, 2.08 mol) was added dropwise at 20° C. to methanol (5 L). After the addition was completed, the mixture was stirred at this temperature for 30 minutes. Then 5-hydroxy-pyrazine-2-carboxylic acid (100 g, 714 mmol) was added, and the mixture was heated at reflux for 2 hours. The reaction mixture was concentrated in vacuo, and the residue was recrystallised from methanol (400 mL) to give 71 g (464 mmol) of the title compound in 65% yield.

Preparation 41

5-Chloro-pyrazine-2-carboxylic acid methyl ester

A mixture of 5-hydroxy-pyrazine-2-carboxylic acid methyl ester (Preparation 40, 50 g, 324 mmol) and $POCl_3$ (500 mL, 5.36 mol) was heated under reflux for 1.5 hours and then poured onto ice. The resulting mixture was extracted with ether (4×500 mL). The organic layers were concentrated in vacuo, and the residue was recrystallised from toluene to give the title compound (30.8 g) in a 55% yield.

Preparation 42

5-Piperidin-1-yl-pyrazine-2-carboxylic acid methyl ester

To a solution of 5-chloro-pyrazine-2-carboxylic acid methyl ester (Preparation 41, 85 g, 492 mmol) in DMF (365 mL) was added DIPEA (129 mL, 738 mmol) and piperidine (58.4 mL, 591 mmol) and the resulting solution was stirred at room temperature for 18 hours. The reaction mixture was poured onto water (4 L) and the resulting precipitate was collected by filtration to give the title compound as a white solid (85.12 g) in a 78% yield.

$^1$H NMR (400 MHz, DMSO-d6) δ ppm 1.50-1.56 (m, 4H), 1.60-1.62 (m, 2H), 3.68-3.73 (m, 4H), 3.80 (s, 3H), 8.35 (s, 1H), 8.60 (s, 1H).

Preparation 43

5-Piperidin-1-yl-pyrazine-2-carboxylic acid

5-Piperidin-1-yl-pyrazine-2-carboxylic acid methyl ester (Preparation 42, 85.1 g, 384 mmol) was added to a solution of sodium hydroxide (61.5 g, 1.53 mol) in water (760 mL). The mixture was stirred mechanically for 1 hour at room temperature. THF (300 mL) was added and stirring was continued for 3 hours. The volatile solvents were removed in vacuo and the remaining aqueous solution was adjusted to pH 4. The mixture was cooled on ice to induce precipitation of the product. The resulting solid was collected by filtration and dried in vacuo to give the title compound as a white solid (56 g) in a 70% yield.

$^1$H NMR (400 MHz, DMSO-d6) δ ppm 1.43-1.61 (m, 6H), 3.60-3.70 (m, 4H), 8.28 (s, 1H), 8.58 (s, 1H), 12.59 (br s, 1H).
LCMS: m/z 208 [M+H]$^+$.

Preparation 44

5-(2-Fluoro-phenoxy)-pyrazine-2-carboxylic acid methyl ester

2-Fluorophenol (21.6 g, 233 mmol) was dissolved in DMF (250 mL) under a calcium chloride drying tube. The solution was cooled to 0° C., and then 60% NaH in paraffin oil (9.3 g, 233 mmol) was added in small portions. After the main portion of NaH had dissolved, 5-chloro-pyrazine-2-carboxylic acid methyl ester (Preparation 41, 40.2 g, 233 mmol) was added. The mixture was refluxed for 1 hour and then poured into water (1 L). The aqueous mixture was extracted with ether (3×300 mL), and the combined organic layers were washed with 2% sodium hydroxide aqueous solution (400 mL) and filtered through a layer of silica gel (40/60 prn). The filtrate was concentrated in vacuo to yield the title compound which was used without further purification.

Preparation 45

5-(2-Fluoro-phenoxy)-pyrazine-2-carboxylic acid 5-(2-Fluoro-phenoxy)-pyrazine-2-carboxylic acid methyl ester (Preparation 44, 57.9 g, 233 mmol) was added to a solution of KOH (15 g, 267 mmol) in 78% ethanol (330 mL). The solution was stirred at room temperature for 18 hours, and the formed precipitate was collected by filtration. The resulting solid was dissolved in water (200 mL), and the solution was acidified with aqueous hydrochloric acid. The formed precipitate was collected by filtration, dried and recrystallised from 41% ethanol (265 mL) to give the title compound (28.3 g, 120.8 mmol) in 51.8% yield.

$^1$H NMR (400 MHz, DMSO-d6) δ ppm 7.29-7.48 (m, 4H), 8.75 (s, 2H), 13.51 (s, 1H).
LCMS: m/z 235.1 [M+H]$^+$.

Preparation 46

6-Cyano-nicotinoyl chloride

6-Cyano-nicotinic acid (120 mg, 810 μmol) was suspended in toluene (1 mL) and thionyl chloride (119 μL, 1.62 mmol) was added dropwise followed by one drop of DMF. The reaction mixture was refluxed for 2.5 hours and then allowed to cool to room temperature for 18 hours. The solvents were removed in vacuo and the residue was azeotroped with toluene to furnish the title compound as a brown oil (134 mg) which was used in further experiments without purification.
LCMS: m/z 167.02 M+H$^+$.

The activity of the compounds of formula (I) may be assessed in the following assays.

Preparation 47

(5-chloroovrazin-2-yl)(2-(6-(2-ethyl-5-fluoro-4-hydroxyphenyl)-1H-indazol-3-yl)-6,7-dihydro-1H-imidazo[4,5-c]pyridin-5(4H)-yl)methanone To a solution of 5-ethyl-2-fluoro-4-[3-(4,5,6,7-tetrahydro-1H-imidazo[4,5-c]pyridin-2-yl)-1H-indazol-6-yl]-phenol preparation 25 (500 mg, 1.326 mmol) and 7 (209.54 mg, 1.326 mmol) in dry DMF (10 ml), DIPEA (0.65 ml, 3.978 mmol) and T3P (2.38 ml, 3.978 mmol) were added and the reaction mixture was stirred at room temperature for 1 h. TLC & LCMS showed product formation. The reaction mixture was evaporated in vacuo, ice water was added to form solid precipitate which was washed with water, saturated sodium bi carbonate and pentane to afford a brown solid (460 mg, 67.08%).

1H NMR (400 MHz, DMSO) δ (ppm): 1.04 (t, 3H), 2.66-2.81 (m, 2H), 3.72 (m, 1H), 4.04 (t, 1H), 4.57 (s, 1H), 4.74 (s, 1H), 6.89-6.92 (m, 1H), 6.98-7.13 (m, 2H), 7.36 (d, 1H), 8.31 (d, 1H), 8.75 (d, 1H), 8.86-8.87 (m, 1H), 9.82 (s, 1H), 12.55 (s, 1H), 13.21 (s, 1H);
LCMS: Rt=2.89 min; m/z 518.4 [M+H]+.

JAK3 Isolated Enzyme High ATP Caliper Endpoint Assay 4 mM stock solutions of test compounds are prepared and serially diluted in 100% DMSO. A standard curve using PF-00956980-00 at a top concentration of 4 mM is also prepared. High percentage effect (HPE) is defined by 500 μM PF-00956980-00 and 0% effect (ZPE) is defined by 100% DMSO. Greiner 384 well plates are prepared containing 400 nl of serially diluted compound, standard and HPE/ZPE. Final top assay concentration is 80 μM as the assay dilution factor is fifty.

JAK3 enzyme (Invitrogen) stock solution is made up at 4.1 μM in sterile water. JAK3 enzyme stock is diluted to 2 nM in assay buffer (10 mM HEPES free acid pH 7.5, 10 mM HEPES free base pH 7.5, 10 mM MgCL$_2$, 0.0005% Tween-20, 0.01% BSA) containing 2 mM DTT (all supplied by Sigma). ATP is made up at 10 mM stock in sterile water and diluted to 800 μM in assay buffer. Peptide (American peptide company) is made up at 30 mM in 100% DMSO and diluted to 3 μM in assay buffer. Stop buffer comprises 140 mM HEPES, 22.5 mM EDTA (Sigma) and 0.15% coating reagent (Caliper Life Sciences).

Assays are performed in Greiner polypropylene 384 well plates. Following compound preparation within the plate 10 μl of enzyme in assay buffer containing DTT is added using a Multidrop Micro. Final assay concentration of enzyme is 1 nM. Compound and enzyme are pre-incubated for 60 minutes at room temperature using low evaporation lids before addition of 10 μl ATP/peptide mixture in assay buffer using a Multidrop Micro. Final assay concentrations are 400 μM ATP and 1.5 μM peptide. Plates are foil sealed and incubated for a further 60 minutes at room temperature. Stop solution is added to the plates (20 μl/well) using a Multidrop Micro and plates are loaded onto the Caliper EZReader II. Data is generated by the shift in mobility of non-phosphorylated peptide substrates and phosphorylated products by electrophoresis within a chip and detected via LED induced fluorescence. Data is analysed using LabChip EZReader software which calculates the relative heights of the substrate and product peaks and reports product/product plus substrate peak ratio. Test compound data are subsequently expressed as percentage inhibition defined by HPE and ZPE values for each plate. Percentage inhibition in the presence of test compound is plotted against compound concentration on a log scale to determine an $IC_{50}$ from the resultant sigmoid curve.

JAK1 Isolated Enzyme High ATP Caliper Endpoint Assay 4 mM stock solutions of test compounds are prepared and serially diluted in 100% DMSO. A standard curve using PF-00956980 (commercially available from Sigma Aldrich) at a top concentration of 4 mM is also prepared. High percentage effect (HPE) is defined by 500 µM PF-00956980 and 0% effect (ZPE) is defined by 100% DMSO. Greiner 384 well plates are prepared containing 400 nl of serially diluted compound, standard and HPE/ZPE. Final top assay concentration is 80 µM as the assay dilution factor is fifty.

JAK1 enzyme (Invitrogen) stock solution is made up at 5.2 µM in sterile water. JAK1 enzyme stock is diluted to 20 nM in assay buffer (10 mM HEPES free acid pH 7.5, 10 mM HEPES free base pH 7.5, 10 mM $MgCL_2$, 0.0005% Tween-20, 0.01% BSA) containing 2 mM DTT (all supplied by Sigma) with the addition of one protease tablet per 25 mls buffer (Roche). ATP is made up at 10 mM stock in sterile water and diluted to 5 mM in assay buffer. Peptide H236 (Caliper Life Sciences) is made up at 1.5 mM in 100% DMSO and diluted to 3 µM in assay buffer. Stop buffer comprises 140 mM HEPES, 22.5 mM EDTA (Sigma) and 0.15% coating reagent (Caliper Life Sciences).

Assays are performed in Greiner polypropylene 384 well plates. Following compound preparation within the plate 10 µl of enzyme in assay buffer containing DTT is added using a Multidrop Micro. Final assay concentration of enzyme is 10 nM. Compound and enzyme are pre-incubated for 30 minutes at room temperature using low evaporation lids before addition of 10 µl ATP/peptide mixture in assay buffer using a Multidrop Micro. Final assay concentrations are 2.5 mM ATP and 1.5 µM peptide. Plates are foil sealed and incubated for a further 120 minutes at room temperature. Stop solution is added to the plates (20 µl/well) using a Multidrop Micro and plates are loaded onto the Caliper EZReader II. Data is generated by the shift in mobility of non-phosphorylated peptide substrates and phosphorylated products by electrophoresis within a chip and detected via LED induced fluorescence. Data is analysed using LabChip EZReader software which calculates the relative heights of the substrate and product peaks and reports product/product plus substrate peak ratio. Test compound data are subsequently expressed as percentage inhibition defined by HPE and ZPE values for each plate. Percentage inhibition in the presence of test compound is plotted against compound concentration on a log scale to determine an $IC_{50}$ from the resultant sigmoid curve.

The following Table shows the available $IC_{50}$ data for Examples 1-31 in the JAK-1 and JAK-3 isolated enzyme high ATP Caliper endpoint assays described above.

| Example number | JAK-3 $IC_{50}$ (nM) | JAK-1 $IC_{50}$ (nM) |
|---|---|---|
| 1 | <0.6 | <0.7 |
| 2 | 0.5 | 46 |
| 3 | 1.0 | 3.7 |
| 4 | 0.5 | 5.4 |
| 5 | No data | No data |
| 6 | 1.3 | 8.4 |
| 7 | 1.5 | 2.5 |
| 8 | 1.4 | 2.9 |
| 9 | 1.9 | 18.9 |
| 10 | 1.3 | 4.5 |
| 11 | 1.0 | 2.5 |
| 12 | 1.6 | 1.2 |
| 13 | 3.6 | 1.5 |
| 14 | 1.4 | 0.8 |
| 15 | 1.0 | No data |
| 16 | 1.9 | 0.7 |
| 17 | 1.4 | 3.4 |
| 18 | 1.4 | 4.2 |
| 19 | 2.2 | 4.3 |
| 20 | 5.6 | 2.6 |
| 21 | 1.4 | 5.9 |
| 22 | 2.6 | 3.0 |
| 23 | 1.2 | 1.7 |
| 24 | 2.4 | 6.2 |
| 25 | 1.4 | 4.0 |
| 26 | 4.1 | 4.0 |
| 27 | No data | No data |
| 28 | 10.9 | 13.7 |
| 29 | 42 | 1.1 |
| 30 | 6.7 | 7.7 |
| 31 | 186 | 66 |

As a comparator compound, Example 24(c) of WO 2001/002369 was tested. It gave an $IC_{50}$ of 119 nM in the JAK-3 assay and an $IC_{50}$ of 120 nM in the JAK-1 assay.

JAK1/3 Whole Cell Reporter Gene Assay 4 mM stock solutions of test compounds are prepared and serially diluted in 100% DMSO. A standard curve using PF-00956980 at a top concentration of 10 mM is also prepared. High percentage effect (HPE) is defined by 10 mM PF-00956980 and 0% effect (ZPE) is defined by 100% DMSO. Plates containing 1 µl of serially diluted compound, standard and HPE/ZPE are diluted by addition of 39 µl assay media (Optimem with 100 uM NEAA, 10 uM sodium pyruvate and 100 U penicillin/100 ug streptomycin (Invitrogen)) using a Multidrop Combi. This dilutes test compounds to a top concentration of 100 µM. Final top assay concentration is 10 µM as the assay dilution factor is ten. Final DMSO concentration is 0.25%.

CD40 ligand is a member of the TNF superfamily and activates B cells. CD40 (Invitrogen) is prepared at 0.1 mg/ml in PBS minus $Ca^{2+}$, minus $Mg^{2+}$. The concentration of CD40 required for activation is predetermined by CD40 titration with the cell line. Interleukin-4 (IL-4, Invitrogen) is used as the co-activator and functions by binding to the IL-4 receptor complex leading to recruitment and activation of JAK1 and JAK3 tyrosine kinases. IL-4 is prepared at 1 mg/ml in sterile water to generate a stock solution. This is further diluted to 100 ng/ml in assay media. Inhibition of the STATE-beta-lactamase reporter response is measured in the presence of IL-4 at an approximate $EC_{50}$ concentration.

Beta lactamase dye reagent comprises three components and is made up by adding 1 part CCF4 dye, 5 parts solution B and 77 parts Live Blazer-substrate mixture.

Assays are performed in Greiner 384 well black polypropylene clear bottomed plates. The Invitrogen Cellsensor STATE-bla-RA-1 cell line is thawed, counted and resuspended at $1.88 \times 10^6$ cells/ml. Cells are stimulated with CD40 ligand by addition of 5.56 µl of 0.1 mg/ml stock per 1 ml of cell suspension. Cells are plated out at 60000 cells/well, 32 µl/well and incubated at 37° C., 5% $CO_2$. After 18 hours 4 µl test compound is added to the plate using a Platemate Plus. Plates are incubated at 37° C., 5% $CO_2$ for 60 minutes using low evaporation lids before addition of 4 µl IL-4 at a concentration of 100 ng/ml. Plates are incubated at 37° C., 5% $CO_2$ for a further five hours before addition of 10 µl beta lactamase dye. After reagent addition plates are incubated at 37° C., 5% $CO_2$ for 18 hours. Beta lactamase fluorescence signal is read at 460 nm (blue) and 530 nm (green) and a ratio calculated using an Envision. Test compound data are expressed as percentage inhibition defined by HPE and ZPE values for each plate. Percentage inhibition in the presence of test compound is plotted against compound concentration on a log scale to determine an $IC_{50}$ from the resultant sigmoid curve.

Example 4 gave an $IC_{50}$ of 140 nM in this assay.

JAK1 and JAK2 PathHunter Assay 4 mM stock solutions of test compounds are prepared and serially diluted in 100% DMSO. A standard curve using PF-00956980 at a top concentration of 10 mM is also prepared. High percentage effect (HPE) is defined by 10 mM PF-00956980 and 0% effect (ZPE) is defined by 100% DMSO. Plates containing 1 µl of serially diluted compound, standard and HPE/ZPE are diluted by addition of 65 µl compound diluent (PBS minus $Ca^{2+}$, minus $Mg^{2+}$ with 0.05% pluronic F127) using a Multidrop Combi. This dilutes test compounds to a top concentration of 60 µM. Final top assay concentration is 10 µM as the assay dilution factor is six. Final DMSO concentration is 0.25%.

Prolactin (Peprotech) is used for the agonist challenge. Prolactin is prepared at 40 µM in compound diluent to generate a stock solution and further diluted to 6 µM in compound diluent. A standard curve is prepared in compound diluent. Prolactin is also diluted to a concentration of 15 nM (2.5 nM fac). Antagonism of the JAK1 or JAK2 prolactin response is measured in the presence of prolactin at an approximate $EC_B$ concentration for JAK1 and approximately $EC_{100}$ for JAK2.

PathHunter detection reagent comprises three components and is made up by adding 1 part Galacton Star, 5 parts Emerald II and 19 parts Cell Assay Buffer.

Assays are performed in Greiner white 384 well plates. The PathHunter U2OS cell line expressing the cytosolic tyrosine kinase JAK1 or JAK2 and the membrane bound cytokine receptor prolactin is plated out using OptiMEM (Invitrogen) at 5000 cells/well, 20 µl/well and incubated at 37° C., 5% $CO_2$. After 18 hours 5 µl test compound is added to the plate using a Platemate Plus. Plates are incubated at 37° C., 5% $CO_2$ for 60 minutes before addition of 5 µl prolactin at a concentration of 15 nM. Plates are incubated at room temperature for a further 180 minutes before addition of 10 µl detection reagent. After reagent addition plates are covered and incubated at room temperature for 60 minutes. Luminescence signal is read using an Envision. Test compound data are expressed as percentage inhibition defined by HPE and ZPE values for each plate. Percentage inhibition in the presence of test compound is plotted against compound concentration on a log scale to determine an $IC_{50}$ from the resultant sigmoid curve.

Example 4 gave a JAK-1 $IC_{50}$ of 75 nM and a JAK-2 $IC_{50}$ of 176 nM in this assay.

Functional Assessment of JAK Inhibitory Potency Using hrIL-2 and haCD3 stimulated IFNγ Production in Human Isolated PBMC.

Isolation of human Peripheral Blood Mononuclear Cells (PBMC)

Peripheral venous blood from healthy volunteers of either sex was collected into 50 ml centrifuge tubes (Corning) containing 1 ml of 5 mg/ml heparin (Sigma H3400) in distilled water. The heparininsed blood was diluted using an equal volume of sterile Dulbeccos phosphate buffered saline (PBS: Invitrogen 14190) before decanting into 50 ml Leucosep tubes (Sigma A0561). The Leucosep tubes were centrifuged at 400 g for 30 min at room temperature and the buffycoat at the Ficoll:Plamsa interface collected into clean centrifuge tubes and the volum made up to 50 ml using PBS and centrifuging at 200 g for 10 min at room temperature. The supernatent was discarded and the pellet resuspended in assay media (Dulbeccos Modified Essential Medium (DMEM: Invitrogen 11971025) containing 5% Foetal Bovine Serum, 100 U/mIpenicilin/100 µg/ml streptomycin (Sigma P4458) at $2\times10^6$ lymphocytes per ml for IFNγ experiments and at $1\times10^6$ lymphocytes per ml for the pYSTAT5 experiments.

hrIL$_2$/haCD3 Stimulated IFNγ Production

180 µl of PBMC cell suspension was added to each well of a sterile 96 well, flat bottomed plate (Corning-Costar 3598). After a 1 h incubation at 37° C., 10 µl of test compound dilution (final assay concentration range of 0.3 nM to 1 µM in half log increments) or vehicle (2% DMSO in Hanks Balanced Salt Solution (Sigma H8264)) was added to the appropriate well and the plates incubated at 37° C., in 95% $O_2$ 15% $CO_2$ for 1 h. 10 µl of 200 ng/ml IL-2(R&D systems 202-IL): 20 µg/ml aCD3 (BD Biosciences 555329) (final assay concentrations of 10 ng/ml and 1 µg/ml respectively) in assay buffer was added and the plates incubated at 37° C., in 95% $O_2$/5% $CO_2$ for 18 h. Plates were removed from the incubator and centrifuged at 200 g for 5 min at room temperature. 100 µl supernatant was collected, diluted 1:4 and IFNγ content determined using a commercially available IFNγ ELISA kit (Invitrogen CHC1233) as per the manufacturer's instructions. Absorbances were measured using a Spectramax 190/250 plate reader (Molecular Devices). The IFNγ concentration of test wells was expressed as % of the IFNγ concentration produced in wells exposed to IL-2/aCD3 in the absence of test compound, and $IC_{50}$ values determined using a 4 parameter curve fit.

Example 4 gave an $IC_{50}$ of 70 nM in this assay.

hrIL$_2$/haCD3 Stimulated pYSTAT5 in PBMC Lymphocytes

90 µl of PBMC cell suspension was added to each well of a 96 well plate (Corning-Costar 3598) along with 10 µl of test compound dilution giving a final assay concentration range of 0.03 nM to 1 µM in half log increments. The plates were incuated at 37° C., in 95% $O_2$/5% $CO_2$ for 1 h before 10 µl rhIL2 (3 µg/ml final assay concentration) was added to appropriate wells and the plates incubated at the stated conditions for a further 15 min. 25 µl of 20% formaldehyde (Tousimis) was added to all wells and the plates left at room temperature for 10 min prior to centrifugation at 400 g for 4 min at room temperature. 200 µl PBS was added to each well and centrifugation repeated as just described. The supernatant was removed and 50 µl of a 1:50 dilution of Mouse anti-human CD3 (BD Biosciences 555329) in 0.1% BSA (Sigma A7906)/PBS added to each well (excluding control wells) and the plates incubated at room temperature in the dark for 30 min. 150 µl of 0.1% BSA/PBS was added to each well and the plate centrifuged at 400 g for 4 min before the supernatant was discarded and 100 µl ice-cold Phosflow Perm Buffer III (BD Biosciences 612599) added. The plates were briefly vortexed and incubated on ice in the dark for 30 min before 100 µl of 0.1% BSA/PBS was added and the plates centrifuged again as just described. 20 µl of a 1:20 dilution of AF647 anti-phospho-STAT5 antibody (in PBS) was added to the wells (excluding controls) and incubated in the dark at room temperature for 30 min before adding 180 µl of 0.1% BSA/PBS and centrifuging as already described. Once the supernatant was discarded the cells were resuspended in 100 µl of 2% formaldehyde and the plates stored at 4° C. overnight. Plates were read the next day on a FACS Canto (Becton Dickinson). Lymphocytes were gated on PE immunofluorescence and the AF647 signal used as a measure of pYSTAT5 expression. IC$_{50}$ values were generated in Excel using a four parameter curve fit.

Example 4 gave an IC$_{50}$ of 45 nM in this assay.

For determination of compound duration of action (DoA) cells were incubated with compound at an approximate IC$_{80}$ concentration for 1 h before being washed by cenrifugation and resuspension in assay media without compound. At set intervals after wash cells were stimulated with IL-2:aCD3 for 15 min and the plates processed as described above. 100% inhibition was defined as reduction of pYSTAT5 levels down to basal. DoA was calculated as the time taken for the inhibition to reverse by 50% (T$_{50}$%)

Example 4 gave a DoA of >8.8 hours in this assay.

What is claimed is:

1. A method of treating a disease or condition for which a JAK inhibitor is indicated in a subject in need of such treatment, wherein said disease or condition is selected from allergic rhinitis, nasal congestion, rhinorrhea, perennial rhinitis, nasal inflammation, asthma, chronic obstructive pulmonary disease, chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, pulmonary vascular disease, pulmonary arterial hypertension, acute lung injury, bronchiectasis, sinusitis, allergic conjunctivitis, idiopathic pulmonary fibrosis, inflammation, neuroinflammation, arthritis, rheumatoid arthritis, spondyloarthropathies, systemic lupus erythematous arthritis, osteoarthritis, gouty arthritis, pain, fever, pulmonary sarcoisosis, silicosis, atherosclerosis, myocardial infarction, thrombosis, congestive heart failure and cardiac reperfusion injury, stroke, ischemia, reperfusion injury, brain edema, brain trauma, neurodegeneration, inflammatory bowel disease, Crohn's disease, ulcerative colitis, nephritis, retinitis, retinopathy, macular degeneration, glaucoma, diabetes (type 1 and type 2), diabetic neuropathy, myalgia, endotoxic shock, toxic shock syndrome, autoimmune disease, osteoporosis, multiple sclerosis, endometriosis, menstrual cramps, vaginitis, candidiasis, cancer, fibrosis, obesity, muscular dystrophy, polymyositis, Alzheimer's disease, skin flushing, eczema, psoriasis, or atopic dermatitis, comprising administering to the subject a therapeutically effective amount of a compound of formula (I)

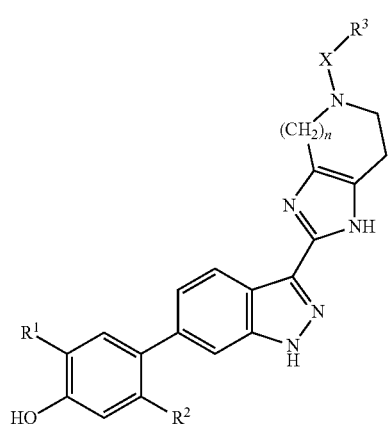

or a pharmaceutically acceptable salt thereof, or a pharmaceutically acceptable solvate of said compound or pharmaceutically acceptable salt, wherein:

$R^1$ is halo;

$R^2$ is $C_1$-$C_6$ alkyl optionally substituted by one or more fluorine atoms;

X is a bond, —CO—, —SO$_2$— or —CH$_2$—;

$R^3$ is Aryl$^1$, Het$^1$ or Het$^2$, each of which is optionally substituted by 1 substituent —Y—R$^4$ and/or 1-4 substituents each independently selected from R$^5$;

n is 1 or 2;

Aryl$^1$ is phenyl or naphthyl;

Het$^1$ is (i) a 6-membered aromatic heterocycle containing 1-3 N atoms or (ii) a 5-membered aromatic heterocycle containing either (a) 1-4 N atoms or (b) 1 O or S atom and 0-3 N atoms;

Het$^2$ is (i) a 10-membered bicyclic aromatic heterocycle containing 1-4 N atoms or (ii) a 9-membered bicyclic aromatic heterocycle containing either (a) 1-4 N atoms or (b) 1 O or S atom and 0-3 N atoms or (iii) an 8-membered bicyclic aromatic heterocycle containing (a) 1-4 N atoms or (b) 1 O or S atom and 1-3 N atoms or (c) 2 O or S atoms and 0-2 N atoms;

Y is a bond or —O—;

$R^4$ is Aryl$^2$ or Het$^3$;

$R^5$ is $C_1$-$C_6$ alkyl, $C_3$-$C_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ or —NR$^6$SO$_2$NR$^7$R$^8$;

$R^6$ is H, $C_1$-$C_6$ alkyl or $C_3$-$C_8$ cycloalkyl, said $C_1$-$C_6$ alkyl being optionally substituted by halo or $C_3$-$C_8$ cycloalkyl;

$R^7$ and $R^8$ are (a) each independently H, $C_1$-$C_6$ alkyl or $C_3$-$C_8$ cycloalkyl, said $C_1$-$C_6$ alkyl being optionally substituted by —NR$^{10}$R$^{11}$, wherein R$^1$ and R$^{11}$ are $C_1$-$C_6$ alkyl or taken together with the nitrogen atom to which they are attached form a 4-, 5- or 6-membered saturated heterocyclic ring containing 1-2 nitrogen atoms or 1 nitrogen and 1 oxygen atom, said heterocyclic ring being optionally substituted by one or more $C_1$-$C_6$ alkyl or $C_3$-$C_8$ cycloalkyl groups; or, (b) are taken together with the nitrogen atom to which they are attached to form a 4-, 5- or 6-membered saturated heterocyclic ring containing 1-2 nitrogen atoms or 1 nitrogen and 1 oxygen atom, said heterocyclic ring being optionally substituted by one or more $C_1$-$C_6$ alkyl or $C_3$-$C_8$ cycloalkyl groups;

$R^9$ is $C_1$-$C_6$ alkyl or $C_3$-$C_8$ cycloalkyl;

Aryl$^2$ is phenyl or naphthyl, said phenyl and naphthyl being optionally substituted with 1-5 substituents selected from $C_1$-$C_6$ alkyl, $C_3$-$C_8$ cycloalkyl, halo, —CN, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$; and Het$^3$ is a 3 to 8-membered saturated or partially unsaturated monocyclic heterocycle, containing 1 or 2 heteroatoms selected from O and N, said heterocycle being optionally substituted by 1-5 substituents selected from $C_1$-$C_6$ alkyl, $C_3$-$C_8$ cycloalkyl, halo, oxo, —OR$^6$, —NR$^7$R$^8$, —SR$^6$, —SOR$^9$, —SO$_2$R$^9$, —COR$^6$, —OCOR$^6$, —COOR$^6$, —NR$^6$COR$^6$, —CONR$^7$R$^8$, —NR$^6$SO$_2$R$^9$, —SO$_2$NR$^7$R$^8$, —NR$^6$CONR$^7$R$^8$, —NR$^6$COOR$^9$ and —NR$^6$SO$_2$NR$^7$R$^8$.

2. The method of claim 1 wherein R$^1$ is fluoro.

3. The method of claim 1 wherein R$^2$ is CH$_2$CH$_3$ or CH$_2$CF$_3$.

4. The method of claim 1 wherein n is 1.

5. The method of claim 1 wherein n is 2.

6. The method of claim 1 wherein X is a bond.

7. The method of claim 1 wherein X is —CO—.

8. The method of claim 1 wherein X is —SO$_2$—.

9. The method of claim 1 wherein X is —CH$_2$—.

10. The method of claim 1 wherein, wherein R$^3$ is phenyl, thiazolyl, quinolinyl, pyrimidinyl, [1,8]naphthyridinyl or pyridyl, each of which is optionally substituted by 1 substituent selected from piperidininyl, (fluorophenyl)oxy, phenyloxy and morpholinyl and 1-2 substituents each independently selected from fluoro, chloro, cyano, methoxy and hydroxy.

11. The method of claim 1 wherein the compound is selected from the group consisting of:

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-fluoro-phenyl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-piperidin-1-yl-pyrazin-2-yl)methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(6-phenoxy-pyridin-3-yl)methanone;

5-Ethyl-2-fluoro-4-{3-[5-(6-morpholin-4-yl-pyridine-3-sulfonyl)-4,5,6,7-tetrahydro-1H-imidazo[4,5-c]pyridin-2-yl]-1H-indazol-6-yl}-phenol;

5-Ethyl-2-fluoro-4-{3-[5-(6-phenoxy-pyridine-3-sulfonyl)-4,5,6,7-tetrahydro-1H-imidazo[4,5-c]pyridin-2-yl]-1H-indazol-6-yl}-phenol;

(5-Chloro-pyridin-2-yl)-{2-[6-(2-ethyl-5-fluoro-4-hydroxy-phenyl)-1H-indazol-3-yl]-4,5,7,8-tetrahydro-1H-imidazo[4,5-d]azepin-6-yl}-methanone;

2-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-isonicotinonitrile;

{2-[6-(2-Ethyl-5-fluoro-4-hydroxy-phenyl)-1H-indazol-3-yl]-4,5,7,8-tetrahydro-1H-imidazo[4,5-d]azepin-6-yl}-(4-fluoro-phenyl)methanone;

{2-[6-(2-Ethyl-5-fluoro-4-hydroxy-phenyl)-1H-indazol-3-yl]-4,5,7,8-tetrahydro-1H-imidazo[4,5-d]azepin-6-yl}-isothiazol-3-yl-methanone;

5-Ethyl-2-fluoro-4-{3-[5-(4-fluoro-benzenesulfonyl)-4,5,6,7-tetrahydro-1H-imidazo[4,5-c]pyridin-2-yl]-1H-indazol-6-yl}-phenol;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-fluoro-phenoxy)-pyrazin-2-yl]-methanone;

4-[3-(6-Benzyl-1,4,5,6,7,8-hexahydro-imidazo[4,5-d]azepin-2-yl)-1H-indazol-6-yl]-5-ethyl-2-fluoro-phenol;

(5-Chloro-pyridin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

5-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-pyridine-2-carbonitrile;

5-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-pyridine-2-carbonitrile;

5-Ethyl-2-fluoro-4-[3-(5-quinolin-6-ylmethyl-4,5,6,7-tetrahydro-1H-imidazo[4,5-c]pyridin-2-yl)-1H-indazol-6-yl]-phenol;

5-Ethyl-2-fluoro-4-{3-[5-(4-hydroxy-benzyl)-4,5,6,7-tetrahydro-1H-imidazo[4,5-c]pyridin-2-yl]-1H-indazol-6-yl}-phenol;

5-Ethyl-2-fluoro-4-{3-[5-(3-hydroxy-benzyl)-4,5,6,7-tetrahydro-1H-imidazo[4,5-c]pyridin-2-yl]-1H-indazol-6-yl}-phenol;

4-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;

5-Ethyl-2-fluoro-4-{3-[5-(3-methoxy-benzyl)-4,5,6,7-tetrahydro-1H-imidazo[4,5-c]pyridin-2-yl]-1H-indazol-6-yl}-phenol;

5-Ethyl-2-fluoro-4-[3-(5-quinolin-3-ylmethyl-4,5,6,7-tetrahydro-1H-imidazo[4,5-c]pyridin-2-yl)-1H-indazol-6-yl]-phenol;

5-Ethyl-2-fluoro-4-{3-[5-(6-phenoxy-pyridin-3-ylmethyl)-4,5,6,7-tetrahydro-1H-imidazo[4,5-c]pyridin-2-yl]-1H-indazol-6-yl}-phenol;

5-Ethyl-2-fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-phenol;

3-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;

5-Ethyl-2-fluoro-4-{3-[5-(4-fluoro-benzyl)-4,5,6,7-tetrahydro-1H-imidazo[4,5-c]pyridin-2-yl]-1H-indazol-6-yl}-phenol;

5-Ethyl-2-fluoro-4-[3-(5-[1,8]naphthyridin-2-ylmethyl-4,5,6,7-tetrahydro-1H-imidazo[4,5-c]pyridin-2-yl)-1H-indazol-6-yl]-phenol;

(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(5-piperidin-1-yl-pyrazin-2-yl)-methanone;

(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(4-fluoro-phenyl)-methanone; and, 4-[3-(5-Benzyl-4,5,6,7-tetrahydro-1H-imidazo[4,5-c]pyridin-2-yl)-1H-indazol-6-yl]-2-fluoro-5-(2,2,2-trifluoro-ethyl)-phenol;

or a pharmaceutically acceptable salt thereof, or a pharmaceutically acceptable solvate of said compound or salt.

12. The method of claim 1 wherein the compound is selected from the group consisting of:

{5-[(2-Dimethylamino-ethyl)-methyl-amino]-pyrazin-2-yl}-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-pyrrolidin-1-yl-ethylamino)-pyrazin-2-yl]-methanone;

[5-(2-Dimethylamino-ethylamino)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

[5-(4-Dimethylamino-piperidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-{5-[ethyl-(2-hydroxy-ethyl)-amino]-pyrazin-2-yl}-methanone;

[5-((R)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

[5-((S)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-etrahydroimidazo[4,5c]pyridin-5-yl}-[5-(2-piperidin-1-yl-ethylamino)-pyrazin-2-yl]-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-piperazin-1-yl-ethylamino)-pyrazin-2-yl]-methanone;

{2-[6-(2-Ethyl-5-fluoro-4-hydroxy-phenyl)-1H-indazol-3-yl]-1,4,6,7-tetrahydro-imidazo[4,5-]pyridin-5-yl}-(4-methyl-3,4,5,6-tetrahydro-2H-[1,2']bipyrazinyl-5'-yl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-morpholin-4-yl-pyrazin-2-yl)-methanone;

{2-[6-(2-Ethyl-5-fluoro-4-hydroxy-phenyl)-1H-indazol-3-yl]-1,4,6,7-tetrahydro-idazo[4,5c]pyridin-5-yl}-[5-(4-methyl-piperidin-1-yl)-pyrazin-2-yl]-methanone;

(5-Cyclopentylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-morpholin-4-yl-ethylamino)-pyrazin-2-yl]-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-isopropyl-3,4,5,6-tetrahydro-2H-[1,2']bipyrazinyl-5'-yl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-pyrrolidin-1-yl-pyrazin-2-yl)-methanone;

{2-[6-(2-Ethyl-5-fluoro-4-hydroxy-phenyl)-1H-indazol-3-yl]-1,4,6,7-tetrahydro-imidazo[4,5-]pyridin-5-yl}-[5-(ethyl-methyl-amino)-pyrazin-2-yl]-methanon;

(5-Cyclohexylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

(5-Dimethylamino-pyrazin-2-yl)-{2-[6-(2-ethyl-5-fluoro-4-hydroxy-phenyl)-1H-indazol-3-yl]-,4,6,7-tetrahydro-imidazo[4,5-c]pyridin-5-yl}-methanone;

(5-Azetidin-1-yl-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

2-Fluoro-4-{3-[5-(4-fluoro-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(6-phenoxy-pyridin-3-ylmethyl)-4,5,6,7-tetrahydro-1H-imidazo[4,5-c]pyridin-2-yl]-H-indazol-6-yl}-5-(2,2,2-trifluoro-ethyl)-phenol;

2-Fluoro-4-{3-[5-(4-methoxy-benzyl)-4,5,6,7-tetrahydro-1H-imidazo[4,5-c]pyridin-2-yl]-1H indazol-6-yl}-5-(2,2,2-trifluoro-ethyl)phenol;

2-Fluoro-4-{3-[5-(4-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3-methoxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-[3-(5-quinolin-6-ylmethyl-4,5,6,7-tetrahydro-1H-imidazo[4,5-c]pyridin-2-yl)-1H-indazol-6-yl]-5-(2,2,2-trifluoro-ethyl)-phenol;

2-Fluoro-4-[3-(5-quinolin-3-ylmethyl-4,5,6,7-tetrahydro-1H-imidazo[4,5-c]pyridin-2-yl)-1H-indazol-6-yl]-5-(2,2,2-trifluoro-ethyl)-phenol;

2-Fluoro-4-[3-(5-[1,8]naphthyridin-3-ylmethyl-4,5,6,7-tetrahydro-1H-imidazo[4,5-c]pyridin-2-yl)-1H-indazol-6-yl]-5-(2,2,2-trifluoro-ethyl)-phenol;

((3R,5S)-3,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-((S)-3-methyl-3,4,5,6-tetrahydro-2H-[1,2']bipyrazinyl-5'-yl)-methanone;

((2S,5R)-2,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone; and, {2-[6-(2-Ethyl-5-fluoro-4-hydroxy-phenyl)-1H-indazol-3-yl]-1,4,6,7-tetrahydro-imidazo[4,5-]pyridin-5-yl}-(3,4,5,6-tetrahydro-2H-[1,2']bipyrazinyl-5'-yl)-methanone;

or a pharmaceutically acceptable salt thereof, or a pharmaceutically acceptable solvate of said compound or salt.

13. The method of claim 1, wherein said disease or condition is chronic obstructive pulmonary disease.

14. The method of claim 13, wherein the compound is selected from the group consisting of:

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-fluoro-phenyl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-piperidin-1-yl-pyrazin-2-yl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(6-phenoxy-pyridin-3-yl)-methanone;

5-Ethyl-2-fluoro-4-{3-[5-(6-morpholin-4-yl-pyridine-3-sulfonyl)-4,5,6,7-tetrahydro-1H-imidazo[4,5-c]pyridin-2-yl]-1H-indazol-6-yl}-phenol;

5-Ethyl-2-fluoro-4-{3-[5-(6-phenoxy-pyridine-3-sulfonyl)-4,5,6,7-tetrahydro-1H-imidazo[4,5-c]pyridin-2-yl]-1H-indazol-6-yl}-phenol;

(5-Chloro-pyridin-2-yl)-{2-[6-(2-ethyl-5-fluoro-4-hydroxy-phenyl)-1H-indazol-3-yl]-4,5,7,8-tetrahydro-1H-imidazo[4,5-d]azepin-6-yl}-methanone;

2-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-isonicotinonitrile;

{2-[6-(2-Ethyl-5-fluoro-4-hydroxy-phenyl)-1H-indazol-3-yl]-4,5,7,8-tetrahydro-1H-imidazo[4,5-d]azepin-6-yl}-(4-fluoro-phenyl)methanone;
{2-[6-(2-Ethyl-5-fluoro-4-hydroxy-phenyl)-1H-indazol-3-yl]-4,5,7,8-tetrahydro-1H-imidazo[4,5-d]azepin-6-yl}-isothiazol-3-yl-methanone;
5-Ethyl-2-fluoro-4-{3-[5-(4-fluoro-benzenesulfonyl)-4,5,6,7-tetrahydro-1H-imidazo[4,5-c]pyridin-2-yl]-1H-indazol-6-yl}-phenol;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-fluoro-phenoxy)-pyrazin-2-yl]-methanone;
4-[3-(6-Benzyl-1,4,5,6,7,8-hexahydro-imidazo[4,5-d]azepin-2-yl)-1H-indazol-6-yl]-5-ethyl-2-fluoro-phenol;
(5-Chloro-pyridin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
5-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-pyridine-2-carbonitrile;
5-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-pyridine-2-carbonitrile;
5-Ethyl-2-fluoro-4-[3-(5-quinolin-6-ylmethyl-4,5,6,7-tetrahydro-1H-imidazo[4,5-c]pyridin-2-yl)-1H-indazol-6-yl]-phenol;
5-Ethyl-2-fluoro-4-{3-[5-(4-hydroxy-benzyl)-4,5,6,7-tetrahydro-1H-imidazo[4,5-c]pyridin-2-yl]-1H-indazol-6-yl}-phenol;
5-Ethyl-2-fluoro-4-{3-[5-(3-hydroxy-benzyl)-4,5,6,7-tetrahydro-1H-imidazo[4,5-c]pyridin-2-yl]-1H-indazol-6-yl}-phenol;
4-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;
5-Ethyl-2-fluoro-4-{3-[5-(3-methoxy-benzyl)-4,5,6,7-tetrahydro-1H-imidazo[4,5-c]pyridin-2-yl]-1H-indazol-6-yl}-phenol;
5-Ethyl-2-fluoro-4-[3-(5-quinolin-3-ylmethyl-4,5,6,7-tetrahydro-1H-imidazo[4,5-c]pyridin-2-yl)-1H-indazol-6-yl]-phenol;
5-Ethyl-2-fluoro-4-{3-[5-(6-phenoxy-pyridin-3-ylmethyl)-4,5,6,7-tetrahydro-1H-imidazo[4,5-c]pyridin-2-yl]-1H-indazol-6-yl}-phenol;
5-Ethyl-2-fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-phenol;
3-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;
5-Ethyl-2-fluoro-4-{3-[5-(4-fluoro-benzyl)-4,5,6,7-tetrahydro-1H-imidazo[4,5-c]pyridin-2-yl]-1H-indazol-6-yl}-phenol;
5-Ethyl-2-fluoro-4-[3-(5-[1,8]naphthyridin-2-ylmethyl-4,5,6,7-tetrahydro-1H-imidazo[4,5-c]pyridin-2-yl)-1H-indazol-6-yl]-phenol;
(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(5-piperidin-1-yl-pyrazin-2-yl)-methanone;
(2-{6-[5-Fluoro-4-hydroxy-2-(2,2,2-trifluoro-ethyl)-phenyl]-1H-indazol-3-yl}-1,4,6,7-tetrahydro-imidazo[4,5-c]pyridin-5-yl)-(4-fluoro-phenyl)-methanone; and,
4-[3-(5-Benzyl-4,5,6,7-tetrahydro-1H-imidazo[4,5-c]pyridin-2-yl)-1H-indazol-6-yl]-2-fluoro-5-(2,2,2-trifluoro-ethyl)-phenol;

or a pharmaceutically acceptable salt thereof, or a pharmaceutically acceptable solvate of said compound or salt.

15. The method of claim 13, wherein the compound is selected from the group consisting of:
{5-[(2-Dimethylamino-ethyl)-methyl-amino]-pyrazin-2-yl}-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-pyrrolidin-1-yl-ethylamino)-pyrazin-2-yl]-methanone;
[5-(2-Dimethylamino-ethylamino)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
[5-(4-Dimethylamino-piperidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-{5-[ethyl-(2-hydroxy-ethyl)-amino]-pyrazin-2-yl}-methanone;
[5-((R)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
[5-((S)-3-Dimethylamino-pyrrolidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-etrahydroimidazo[4,5c]pyridin-5-yl}-[5-(2-piperidin-1-yl-ethylamino)-pyrazin-2-yl]-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-piperazin-1-yl-ethylamino)-pyrazin-2-yl]-methanone;
{2-[6-(2-Ethyl-5-fluoro-4-hydroxy-phenyl)-1H-indazol-3-yl]-1,4,6,7-tetrahydro-imidazo[4,5-]pyridin-5-yl}-(4-methyl-3,4,5,6-tetrahydro-2H-[1,2']bipyrazinyl-5'-yl)-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(5-morpholin-4-yl-pyrazin-2-yl)-methanone;
{2-[6-(2-Ethyl-5-fluoro-4-hydroxy-phenyl)-1H-indazol-3-yl]-1,4,6,7-tetrahydro-idazo[4,5c]pyridin-5-yl}-[5-(4-methyl-piperidin-1-yl)-pyrazin-2-yl]-methanone;
(5-Cyclopentylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-morpholin-4-yl-ethylamino)-pyrazin-2-yl]-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(4-isopropyl-3,4,5,6-tetrahydro-2H-[1,2']bipyrazinyl-5'-yl)-methanone;
{2-[6-(2-Ethyl-5-fluoro-4-hydroxy-phenyl)-1H-indazol-3-yl]-1,4,6,7-tetrahydro-imidazo[4,5-c]pyridin-5-yl}-(5-pyrrolidin-1-yl-pyrazin-2-yl)-methanone;
{2-[6-(2-Ethyl-5-fluoro-4-hydroxy-phenyl)-1H-indazol-3-yl]-1,4,6,7-tetrahydro-imidazo[4,5-]pyridin-5-yl}-[5-(ethyl-methyl-amino)-pyrazin-2-yl]-methanon;

(5-Cyclohexylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

(5-Dimethylamino-pyrazin-2-yl)-{2-[6-(2-ethyl-5-fluoro-4-hydroxy-phenyl)-1H-indazol-3-yl]-,4,6,7-tetrahydro-imidazo[4,5-c]pyridin-5-yl}-methanone;

(5-Azetidin-1-yl-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

2-Fluoro-4-{3-[5-(4-fluoro-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3,4,5,6-tetrahydro-2H-[1,2']bipyridinyl-5'-ylmethyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(6-phenoxy-pyridin-3-ylmethyl)-4,5,6,7-tetrahydro-1H-imidazo[4,5-c]pyridin-2-yl]-H-indazol-6-yl}-5-(2,2,2-trifluoro-ethyl)-phenol;

2-Fluoro-4-{3-[5-(4-methoxy-benzyl)-4,5,6,7-tetrahydro-1H-imidazo[4,5-c]pyridin-2-yl]-1H indazol-6-yl}-5-(2,2,2-trifluoro-ethyl)-phenol;

2-Fluoro-4-{3-[5-(4-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3-methoxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-[3-(5-quinolin-6-ylmethyl-4,5,6,7-tetrahydro-1H-imidazo[4,5-c]pyridin-2-yl)-1H-indazol-6-yl]-5-(2,2,2-trifluoro-ethyl)-phenol;

2-Fluoro-4-[3-(5-quinolin-3-ylmethyl-4,5,6,7-tetrahydro-1H-imidazo[4,5-c]pyridin-2-yl)-1H-indazol-6-yl]-5-(2,2,2-trifluoro-ethyl)-phenol;

2-Fluoro-4-[3-(5-[1,8]naphthyridin-3-ylmethyl-4,5,6,7-tetrahydro-1H-imidazo[4,5-c]pyridin-2-yl)-1H-indazol-6-yl]-5-(2,2,2-trifluoro-ethyl)-phenol;

((3R,5S)-3,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-((S)-3-methyl-3,4,5,6-tetrahydro-2H-[1,2']bipyrazinyl-5'-yl)-methanone;

((2S,5R)-2,5-Dimethyl-3,4,5,6-tetrahydro-2H-[1,2']bipyrazinyl-5'-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone; and, {2-[6-(2-Ethyl-5-fluoro-4-hydroxy-phenyl)-1H-indazol-3-yl]-1,4,6,7-tetrahydro-imidazo[4,5-]pyridin-5-yl}-(3,4,5,6-tetrahydro-2H-[1,2']bipyrazinyl-5'-yl)-methanone;

or a pharmaceutically acceptable salt thereof, or a pharmaceutically acceptable solvate of said compound or salt.

16. The method of claim 1, wherein said disease or condition is psoriasis.

17. The method of claim 16, wherein the compound is selected from the group consisting of:

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-fluoro-phenyl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-isothiazol-3-yl-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-piperidin-1-yl-pyrazin-2-yl)methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(6-phenoxy-pyridin-3-yl)-methanone;

5-Ethyl-2-fluoro-4-{3-[5-(6-morpholin-4-yl-pyridine-3-sulfonyl)-4,5,6,7-tetrahydro-1H-imidazo[4,5-c]pyridin-2-yl]-1H-indazol-6-yl}-phenol;

5-Ethyl-2-fluoro-4-{3-[5-(6-phenoxy-pyridine-3-sulfonyl)-4,5,6,7-tetrahydro-1H-imidazo[4,5-c]pyridin-2-yl]-1H-indazol-6-yl}-phenol;

(5-Chloro-pyridin-2-yl)-{2-[6-(2-ethyl-5-fluoro-4-hydroxy-phenyl)-1H-indazol-3-yl]-4,5,7,8-tetrahydro-1H-imidazo[4,5-d]azepin-6-yl}-methanone;

2-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}isonicotinonitrile;

{2-[6-(2-Ethyl-5-fluoro-4-hydroxy-phenyl)-1H-indazol-3-yl]-4,5,7,8-tetrahydro-1H-imidazo[4,5-d]azepin-6-yl}-(4-fluoro-phenyl)-methanone;

{2-[6-(2-Ethyl-5-fluoro-4-hydroxy-phenyl)-1H-indazol-3-yl]-4,5,7,8-tetrahydro-1H-imidazo[4,5-d]azepin-6-yl}-isothiazol-3-yl-methanone;

5-Ethyl-2-fluoro-4-{3-[5-(4-fluoro-benzenesulfonyl)-4,5,6,7-tetrahydro-1H-imidazo[4,5-c]pyridin-2-yl]-1H-indazol-6-yl}-phenol;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-fluoro-phenoxy)-pyrazin-2-yl]-methanone;

4-[3-(6-Benzyl-1,4,5,6,7,8-hexahydro-imidazo[4,5-d]azepin-2-yl)-1H-indazol-6-yl]-5-ethyl-2-fluoro-phenol;

(5-Chloro-pyridin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

5-{2-[6-(2-Ethyl-5-fluoro-4-hydroxy-phenyl)-1H-indazol-3-yl]-1,4,6,7-tetrahydro-imidazo[4,5-c]pyridine-5-carbonyl}-pyridine-2-carbonitrile;

5-{2-[6-(2-Ethyl-5-fluoro-4-hydroxy-phenyl)-1H-indazol-3-yl]-4,5,7,8-tetrahydro-1H-imidazo[4,5-d]azepine-6-carbonyl}-pyridine-2-carbonitrile;

5-Ethyl-2-fluoro-4-[3-(5-quinolin-6-ylmethyl-4,5,6,7-tetrahydro-1H-imidazo[4,5-c]pyridin-2-yl)-1H-indazol-6-yl]-phenol;

5-Ethyl-2-fluoro-4-{3-[5-(4-hydroxy-benzyl)-4,5,6,7-tetrahydro-1H-imidazo[4,5-c]pyridin-2-yl]-1H-indazol-6-yl}-phenol;

5-Ethyl-2-fluoro-4-{3-[5-(3-hydroxy-benzyl)-4,5,6,7-tetrahydro-1H-imidazo[4,5-c]pyridin-2-yl]-1H-indazol-6-yl}-phenol;

4-{2-[6-(2-Ethyl-5-fluoro-4-hydroxy-phenyl)-1H-indazol-3-yl]-1,4,6,7-tetrahydro-imidazo[4,5-c]pyridin-5-ylmethyl}-pyridine-2-carbonitrile;

5-Ethyl-2-fluoro-4-{3-[5-(3-methoxy-benzyl)-4,5,6,7-tetrahydro-1H-imidazo[4,5-c]pyridin-2-yl]-1H-indazol-6-yl}-phenol;

5-Ethyl-2-fluoro-4-[3-(5-quinolin-3-ylmethyl-4,5,6,7-tetrahydro-1H-imidazo[4,5-c]pyridin-2-yl)-1H-indazol-6-yl]-phenol;

5-Ethyl-2-fluoro-4-{3-[5-(6-phenoxy-pyridin-3-ylm-ethyl)-4,5,6,7-tetrahydro-1H-imidazo[4,5-c]pyridin-2-yl]-1H-indazol-6-yl}-phenol;

5-Ethyl-2-fluoro-4-{3-[5-(3,4,5,6-tetrahydro-2H-[1,2']bi-pyridinyl-5'-ylmethyl)-4,5,6,7-tetrahydro-1H-imidazo[4,5-c]pyridin-2-yl]-1H-indazol-6-yl}-phenol;

3-{2-[6-(2-Ethyl-5-fluoro-4-hydroxy-phenyl)-1H-inda-zol-3-yl]-1,4,6,7-tetrahydro-imidazo[4,5-c]pyridin-5-ylmethyl}-pyridine-2-carbonitrile;

5-Ethyl-2-fluoro-4-{3-[5-(4-fluoro-benzyl)-4,5,6,7-tet-rahydro-1H-imidazo[4,5-c]pyridin-2-yl]-1H-indazol-6-yl}-phenol;

5-Ethyl-2-fluoro-4-[3-(5-[1,8]naphthyridin-2-ylmethyl-4,5,6,7-tetrahydro-1H-imidazo[4,5-c]pyridin-2-yl)-1H-indazol-6-yl]-phenol;

(2-{6-[5-Fluoro-4-hydroxy-2-(2,2,2-trifluoro-ethyl)-phe-nyl]-1H-indazol-3-yl}-1,4,6,7-tetrahydro-imidazo[4,5-c]pyridin-5-yl)-(5-piperidin-1-yl-pyrazin-2-yl)-metha-none;

(2-{6-[5-Fluoro-4-hydroxy-2-(2,2,2-trifluoro-ethyl)-phe-nyl]-1H-indazol-3-yl}-1,4,6,7-tetrahydro-imidazo[4,5-c]pyridin-5-yl)-(4-fluoro-phenyl)-methanone; and, 4-[3-(5-Benzyl-4,5,6,7-tetrahydro-1H-imidazo[4,5-c]py-ridin-2-yl)-1H-indazol-6-yl]-2-fluoro-5-(2,2,2-trif-luoro-ethyl)-phenol;

or a pharmaceutically acceptable salt thereof, or a pharma-ceutically acceptable solvate of said compound or salt.

18. The method of claim 16 wherein the compound is selected from the group consisting of:

{5-[(2-Dimethylamino-ethyl)-methyl-amino]-pyrazin-2-yl}-{2-[6-(2-ethyl-5-fluoro-4-hydroxy-phenyl)-1H-in-dazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-pyrrolidin-1-yl-ethylamino)-pyrazin-2-yl]-methanone;

[5-(2-Dimethylamino-ethylamino)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

[5-(4-Dimethylamino-piperidin-1-yl)-pyrazin-2-yl]-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-{5-[ethyl-(2-hydroxy-ethyl)-amino]-pyrazin-2-yl}-methanone;

[5-((R)-3-Dimethylamino-pyrrolidin-1-yl)-pyrazin-2-yl]-{2-[6-(2-ethyl-5-fluoro-4-hydroxy-phenyl)-1H-inda-zol-3-yl]-1,4,6,7-tetrahydro-imidazo[4,5-c]pyridin-5-yl}-methanone;

[5-((S)-3-Dimethylamino-pyrrolidin-1-yl)-pyrazin-2-yl]-{2-[6-(2-ethyl-5-fluoro-4-hydroxy-phenyl)-1H-inda-zol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-etrahydroimidazo[4,5c]pyridin-5-yl}-[5-(2-piperidin-1-yl-ethylamino)-pyrazin-2-yl]-metha-none;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-piperazin-1-yl-ethylamino)-pyrazin-2-yl]-metha-none;

{2-[6-(2-Ethyl-5-fluoro-4-hydroxy-phenyl)-1H-indazol-3-yl]-1,4,6,7-tetrahydro-imidazo[4,5-]pyridin-5-yl}-(4-methyl-3,4,5,6-tetrahydro-2H-[1,2']bipyrazinyl-5'-yl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-morpholin-4-yl-pyrazin-2-yl)-methanone;

{2-[6-(2-Ethyl-5-fluoro-4-hydroxy-phenyl)-1H-indazol-3-yl]-1,4,6,7-tetrahydro-idazo[4,5c]pyridin-5-yl}-[5-(4-methyl-piperidin-1-yl)-pyrazin-2-yl]-methanone;

(5-Cyclopentylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-[5-(2-morpholin-4-yl-ethylamino)-pyrazin-2-yl]-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(4-isopropyl-3,4,5,6-tetrahydro-2H-[1,2']bipyrazinyl-5'-yl)-methanone;

{2-[6-(2-Ethyl-5-fluoro-4-hydroxy-phenyl)-1H-indazol-3-yl]-1,4,6,7-tetrahydro-imidazo[4,5-c]pyridin-5-yl}-(5-pyrrolidin-1-yl-pyrazin-2-yl)-methanone;

{2-[6-(2-Ethyl-5-fluoro-4-hydroxy-phenyl)-1H-indazol-3-yl]-1,4,6,7-tetrahydro-imidazo[4,5-]pyridin-5-yl}-[5-(ethyl-methyl-amino)-pyrazin-2-yl]-methanon;

(5-Cyclohexylamino-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

(5-Dimethylamino-pyrazin-2-yl)-{2-[6-(2-ethyl-5-fluoro-4-hydroxy-phenyl)-1H-indazol-3-yl]-,4,6,7-tetrahydro-imidazo[4,5-c]pyridin-5-yl}-methanone;

(5-Azetidin-1-yl-pyrazin-2-yl)-{2-[6-(2-ethyl-5-fluoro-4-hydroxy-phenyl)-1H-indazol-3-yl]-1,4,6,7-tetrahydro-imidazo[4,5-c]pyridin-5-yl}-methanone;

2-Fluoro-4-{3-[5-(4-fluoro-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3,4,5,6-tetrahydro-2H-[1,2']bipyridi-nyl-5'-ylmethyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(6-phenoxy-pyridin-3-ylmethyl)-4,5,6,7-tetrahydro-1H-imidazo[4,5-c]pyridin-2-yl]-H-inda-zol-6-yl}-5-(2,2,2-trifluoro-ethyl)-phenol;

2-Fluoro-4-{3-[5-(4-methoxy-benzyl)-4,5,6,7-tetrahydro-1H-imidazo[4,5-c]pyridin-2-yl]-1H indazol-6-yl}-5-(2,2,2-trifluoro-ethyl)-phenol;

2-Fluoro-4-{3-[5-(4-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3-methoxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-{3-[5-(3-hydroxy-benzyl)-4,5,6,7-tetrahydro-1H-imidazo[4,5-c]pyridin-2-yl]-1H-indazol-6-yl}-5-(2,2,2-trifluoro-ethyl)-phenol;

2-Fluoro-4-[3-(5-quinolin-6-ylmethyl-4,5,6,7-tetrahydro-1H-imidazo[4,5-c]pyridin-2-yl)-1H-indazol-6-yl]-5-(2,2,2-trifluoro-ethyl)phenol;

2-Fluoro-4-[3-(5-quinolin-3-ylmethyl-4,5,6,7-tetrahydro-1H-imidazo[4,5-c]pyridin-2-yl)-1H-indazol-6-yl]-5-(2,2,2-trifluoro-ethyl)-phenol;

2-Fluoro-4-[3-(5-[1,8]naphthyridin-3-ylmethyl-4,5,6,7-tetrahydro-1H-imidazo[4,5-c]pyridin-2-yl)-1H-inda-zol-6-yl]-5-(2,2,2-trifluoro-ethyl)-phenol;

((3R,5S)-3,5-Dimethyl-3,4,5,6-tetrahydro-2H-[1,2']bi-
pyrazinyl-5'-yl)-{2-[6-(2-ethyl-5-fluoro-4-hydroxy-
phenyl)-1H-indazol-3-yl]-1,4,6,7-tetrahydro-imidazo
[4,5-c]pyridin-5-yl}-methanone;

{2-[6-(2-Ethyl-5-fluoro-4-hydroxy-phenyl)-1H-indazol-
3-yl]-1,4,6,7-tetrahydro-imidazo[4,5-c]pyridin-5-yl}-
((S)-3-methyl-3,4,5,6-tetrahydro-2H-[1,2']bipyrazinyl-
5'-yl)-methanone;

((2S,5R)-2,5-Dimethyl-3,4,5,6-tetrahydro-2H-[1,2']bi-
pyrazinyl-5'-yl)-{2-[6-(2-ethyl-5-fluoro-4-hydroxy-
phenyl)-1H-indazol-3-yl]-1,4,6,7-tetrahydro-imidazo
[4,5-c]pyridin-5-yl}-methanone; and, {2-[6-(2-Ethyl-5-fluoro-4-hydroxy-phenyl)-1H-indazol-
3-yl]-1,4,6,7-tetrahydro-imidazo[4,5-]pyridin-5-yl}-(3,
4,5,6-tetrahydro-2H-[1,2']bipyrazinyl-5'-yl)-metha-
none;

or a pharmaceutically acceptable salt thereof, or a pharmaceutically acceptable solvate of said compound or salt.

* * * * *